(12) United States Patent
Buyse et al.

(10) Patent No.: US 10,875,918 B2
(45) Date of Patent: Dec. 29, 2020

(54) P2X7 RECEPTOR BINDERS AND POLYPEPTIDES COMPRISING THE SAME

(71) Applicant: Ablynx N.V., Ghent-Zwijnaarde (BE)

(72) Inventors: Marie-Ange Buyse, Merelbeke (BE); Catelijne Stortelers, Ghent (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 0 days.

(21) Appl. No.: 15/775,266

(22) PCT Filed: Nov. 11, 2016

(86) PCT No.: PCT/EP2016/077452
§ 371 (c)(1),
(2) Date: May 10, 2018

(87) PCT Pub. No.: WO2017/081265
PCT Pub. Date: May 18, 2017

(65) Prior Publication Data
US 2018/0327491 A1    Nov. 15, 2018

Related U.S. Application Data

(60) Provisional application No. 62/254,298, filed on Nov. 12, 2015.

(51) Int. Cl.
*C07K 16/28* (2006.01)
*A61K 39/00* (2006.01)

(52) U.S. Cl.
CPC ......... *C07K 16/28* (2013.01); *C07K 2317/22* (2013.01); *C07K 2317/24* (2013.01); *C07K 2317/567* (2013.01); *C07K 2317/569* (2013.01); *C07K 2317/76* (2013.01); *C07K 2317/94* (2013.01)

(58) Field of Classification Search
None
See application file for complete search history.

(56) References Cited

FOREIGN PATENT DOCUMENTS

| WO | WO 2012/175741 A2 | 12/2012 |
| WO | WO 2013/024059 A2 | 2/2013 |
| WO | WO 2013/178783 A1 | 12/2013 |
| WO | WO 2015/173325 A2 | 11/2015 |

OTHER PUBLICATIONS

MacCallunn et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Holland et al., Autoantibodies to variable heavy (VH) chain Ig sequences in humans impact the safety and clinical pharmacology of a VH domain antibody antagonist of TNF-α receptor 1. J Clin Immunol. Oct. 2013;33(7):1192-203. doi:10.1007/s10875-013-9915-0. Epub Jul. 6, 2013.
MacCallum et al., Antibody-antigen interactions: contact analysis and binding site topography. J Mol Biol. Oct. 11, 1996;262(5):732-45.

* cited by examiner

*Primary Examiner* — Joanne Hama
*Assistant Examiner* — Jon M Lockard
(74) *Attorney, Agent, or Firm* — Wolf, Greenfield & Sacks, P.C.

(57) ABSTRACT

The present invention relates to amino acid sequences and polypeptides binding to the P2X7 receptor. In particular, the present invention relates to improved heavy-chain immunoglobulin single variable domains (also referred to herein as "ISV's" or "ISVD's") binding to the P2X7 receptor, as well as to proteins, polypeptides and other constructs, compounds, molecules or 5 chemical entities that comprise such ISVD's.

8 Claims, 31 Drawing Sheets

Specification includes a Sequence Listing.

Figure 1

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | -- |
| 110 | 110 | 146 | -- |
| 112 | 112 | 148 | -- |

Source: http://www.bioc.uzh.ch/plueckthun/antibody/Numbering/NumFrame.html

Figure 2

| SEQ ID NO | Description | Sequence |
|---|---|---|
| 1 | reference A: 7P2X3c23 (A14P, Q108L) | EVQLVESGGGLVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVSS |
| 2 | CDR1 (Kabat) | HYAMG |
| 3 | CDR2 (Kabat) | AISSYGSTDYGDSVKG |
| 4 | CDR3 (Kabat/Abm) | ADETLGAVPNFRLHEKYEYEY |
| 5 | CDR1 (Abm) | GRTFRHYAMG |
| 6 | CDR2 (Abm) | AISSYGSTD |
| 7 | CDR3 (Kabat/Abm) | ADETLGAVPNFRLHEKYEYEY |
| 8 | reference B 7P2X1c81 (A14P, Q108L) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVSS |
| 9 | CDR1 (Kabat) | FSTSTMG |
| 10 | CDR2 (Kabat) | AIDWSDFNTYYADSVKG |
| 11 | CDR3 (Kabat/Abm) | HSETRGGTRYFDRPSLYNY |
| 12 | CDR1 (Abm) | GRTFSFSTSTMG |
| 13 | CDR2 (Abm) | AIDWSDFNTY |
| 14 | CDR3 (Kabat/Abm) | HSETRGGTRYFDRPSLYNY |
| 15 | Reference A (89T) | EVQLVESGGGLVQPGGSLRLSCAASGRTFRHYAMGWFRQAPGKEREFVAAISSYGSTDYGDSVKGRFTISRDDAKNTVPLQMNSLKPEDTATYYCAAADETLGAVPNFRLHEKYEYEYWGQGTLVTVSS |
| 16 | Reference A (11V + 110K) | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVKVSS |
| 17 | Reference A (11V + 110Q) | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVQVSS |
| 18 | Reference A (11V + 112K) | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVKS |
| 19 | Reference A (11V + 112Q) | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVQS |
| 20 | Reference A (89L + 110K) | EVQLVESGGGLVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSS |

Figure 2 (continued)

| SEQ ID NO | Description | Sequence |
|---|---|---|
| 21 | Reference A (89L + 110Q) | EVQLVESGGGLVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVQVSS |
| 22 | Reference A (89L + 112K) | EVQLVESGGGLVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVKS |
| 23 | Reference A (89L + 112Q) | EVQLVESGGGLVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVQS |
| 24 | Reference A (11V + 89L) | EVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSS |
| 25 | Reference A (11V + 89L + 110K) | EVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSS |
| 26 | Reference A (11V + 89L + 110Q) | EVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVQVSS |
| 27 | Reference A (11V + 89L + 112K) | EVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVKS |
| 28 | Reference A (11V + 89L + 112Q) | EVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVQS |
| 29 | Reference A (89T)+ A | EVQLVESGGGLVQPGGSLRLSCAASGRTFRHYAMGWFRQAPGKEREFVAAISSYGSTDYGDSVKGRFTISRDDAKNTVPLQMNSLKPEDTATYYCAAADETLGAVPNFRLHEKYEYEYWGQGTLVTVSSA |
| 30 | Reference A (11V + 110K)+ A | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVKVSSA |
| 31 | Reference A (11V + 110Q)+ A | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVQVSSA |
| 32 | Reference A (11V + 112K)+ A | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVKSA |
| 33 | Reference A (11V + 112Q)+ A | EVQLVESGGGVVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVQSA |
| 34 | Reference A (89L + 110K)+ A | EVQLVESGGGLVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSA |

Figure 2 (continued)

| SEQ ID NO | Description | Sequence |
|---|---|---|
| 35 | Reference A (89L + 110Q)+ A | EVQLVESGGGLVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVQVSSA |
| 36 | Reference A (89L + 112K)+A | EVQLVESGGGLVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVTVKSA |
| 37 | Reference A (89L + 112Q)+A | EVQLVESGGGLVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVTVQSA |
| 38 | Reference A (11V + 89L)+ A | EVQLVESGGGVVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVTVSSA |
| 39 | Reference A (11V + 89L + 110K)+ A | EVQLVESGGGVVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVKVSSA |
| 40 | Reference A (11V + 89L + 110Q)+ A | EVQLVESGGGVVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVQVSSA |
| 41 | Reference A (11V + 89L + 112K)+A | EVQLVESGGGVVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVTVKSA |
| 42 | Reference A (11V + 89L + 112Q)+A | EVQLVESGGGVVQPGGSLRLSCAASGRTFRHYAMGWFRQAPGKER EFVAAISSYGSTDYGDSVKGRFTISRDDAKNTVPLQMNSLKPEDTAL YYCAAADETLGAVPNFRLHEKYEYEYWGQGTLVTVQSA |
| 43 | Reference B (89T) | EVQLVESGGKLVQPGGSLRLSCSASGRTFSFSTSTMGWFRQAPGKE LEFVAAIDWSDFNTYYADSVKGRFTISRHNPRNSVYLQLNSLKPEDT ATYYCAAHSETRGGTRYFDRPSLYNYWGQGTLVTVSS |
| 44 | Reference B (11V + 110K) | EVQLVESGGKVVQPGGSLRLSCSASGRTFSFSTSTMGWFRQAPGKE LEFVAAIDWSDFNTYYADSVKGRFTISRHNPRNSVYLQLNSLKPEDT AVYYCAAHSETRGGTRYFDRPSLYNYWGQGTLVKVSS |
| 45 | Reference B (11V + 110Q) | EVQLVESGGKVVQPGGSLRLSCSASGRTFSFSTSTMGWFRQAPGKE LEFVAAIDWSDFNTYYADSVKGRFTISRHNPRNSVYLQLNSLKPEDT AVYYCAAHSETRGGTRYFDRPSLYNYWGQGTLVQVSS |
| 46 | Reference B (11V + 112K) | EVQLVESGGKVVQPGGSLRLSCSASGRTFSFSTSTMGWFRQAPGKE LEFVAAIDWSDFNTYYADSVKGRFTISRHNPRNSVYLQLNSLKPEDT AVYYCAAHSETRGGTRYFDRPSLYNYWGQGTLVTVKS |

Figure 2 (continued)

| SEQ ID NO | Description | Sequence |
|---|---|---|
| 47 | Reference B (11V + 112Q) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVQS |
| 48 | Reference B (89L + 110K) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSS |
| 49 | Reference B (89L + 110Q) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVQVSS |
| 50 | Reference B (89L + 112K) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVKS |
| 51 | Reference B (89L + 112Q) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVQS |
| 52 | Reference B (11V + 89L) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSS |
| 53 | Reference B (11V + 89L + 110K) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSS |
| 54 | Reference B (11V + 89L + 110Q) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVQVSS |
| 55 | Reference B (11V + 89L + 112K) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVKS |
| 56 | Reference B (11V + 89L + 112Q) | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVQS |
| 57 | Reference B (89T)+ A | EVQLVESGGKLVQPGGSLRLSCSASGRTFSFSTSTMGWFRQAPGKELEFVAAIDWSDFNTYYADSVKGRFTISRHNPRNSVYLQLNSLKPEDTATYYCAAHSETRGGTRYFDRPSLYNYWGQGTLVTVSSA |
| 58 | Reference B (11V + 110K)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVKVSSA |
| 59 | Reference B (11V + 110Q)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVQVSSA |
| 60 | Reference B (11V + 112K)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVKSA |
| 61 | Reference B (11V + 112Q)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVQSA |

Figure 2 (continued)

| SEQ ID NO | Description | Sequence |
|---|---|---|
| 62 | Reference B (89L + 110K)+ A | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSA |
| 63 | Reference B (89L + 110Q)+ A | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVQVSSA |
| 64 | Reference B (89L + 112K)+A | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVKSA |
| 65 | Reference B (89L + 112Q)+A | EVQLVESGGKLVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVQSA |
| 66 | Reference B (11V + 89L)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSA |
| 67 | Reference B (11V + 89L + 110K)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSA |
| 68 | Reference B (11V + 89L + 110Q)+ A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVQVSSA |
| 69 | Reference B (11V + 89L + 112K)+A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVKSA |
| 70 | Reference B (11V + 89L + 112Q)+A | EVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVQSA |
| 71 | HIS6-FLAG3 tag | HHHHHHGAADYKDHDGDYKDHDIDYKDDDDKGAA |
| 72 | C-terminal end | VTVKS |
| 73 | C-terminal end | VTVQS |
| 74 | C-terminal end | VKVSS |
| 75 | C-terminal end | VQVSS |
| 76 | C-terminal end | VTVKSX(n) |
| 77 | C-terminal end | VTVQSX(n) |

Figure 2 (continued)

| SEQ ID NO | Description | Sequence |
|---|---|---|
| 78 | C-terminal end | VKVSSX(n) |
| 79 | C-terminal end | VQVSSX(n) |
| 80 | C-terminal end | VTVKSA |
| 81 | C-terminal end | VTVQSA |
| 82 | C-terminal end | VKVSSA |
| 83 | C-terminal end | VQVSSA |
| 84 | C-terminal end | VTVSS |
| 85 | C-terminal end | VTVSSX(n) |
| 86 | C-terminal end | TVTSSA |
| 87 | WO 13/178783; SEQ ID NO:12 (7P2X3c23) | EVQLVESGGGLVQAGGSLRLSCAASGRTFRHYAMGWFRQAPGKER EFVAAISSYGSTDYGDSVKGRFTISRDDAKNTVPLQMNSLKPEDTA VYYCAAADETLGAVPNFRLHEKYEYEYWGQGTQVTVSS |
| 88 | WO 13/178783; SEQ ID NO:6 (7P2X1c81) | EVQLVESGGKLVQAGGSLRLSCSASGRTFSFSTSTMGWFRQAPGKE LEFVAAIDWSDFNTYYADSVKGRFTISRHNPRNSVYLQLNSLKPEDT AVYYCAAHSETRGGTRYFDRPSLYNYWGQGTQVTVSS |
| 89 | Serum albumin binding Nanobody | EVQLVESGGGLVQPGNSLRLSCAASGFTFSSFGMSWVRQAPGKGLE WVSSISGSGSDTLYADSVKGRFTISRDNAKTTLYLQMNSLRPEDTAV YYCTIGGSLSRSSQGTLVTVSS |
| 90 | Serum albumin binding Nanobody | EVQLVESGGGVVQPGNSLRLSCAASGFTFSSFGMSWVRQAPGKGLE WVSSISGSGSDTLYADSVKGRFTISRDNAKTTLYLQMNSLRPEDTAL YYCTIGGSLSRSSQGTLVTVSS |
| 91 | Serum albumin binding Nanobody | EVQLVESGGGVVQPGNSLRLSCAASGFTFSSFGMSWVRQAPGKGLE WVSSISGSGSDTLYADSVKGRFTISRDNAKTTLYLQMNSLRPEDTAL YYCTIGGSLSRSSQGTLVKVSS |
| 92 | Serum albumin binding Nanobody | EVQLLESGGGVVQPGGSLRLSCAASGFTFRSFGMSWVRQAPGKGPE WVSSISGSGSDTLYADSVKGRFTISRDNSKNTLYLQMNSLRPEDTAL YYCTIGGSLSRSSQGTLVTVSS |

Figure 2 (continued)

| SEQ ID NO | Description | Sequence |
|---|---|---|
| 129 | F024500045 K10G A14P L82M K83R | EVQLVESGGGLVQPGGSLRLSCSASGRTFSFSTSTMGWFRQAPGKELEFVAAID WSDFNTYYADSVKGRFTISRHNPRNSVYLQMNSLRPEDTAVYYCAAHSETRGGT RYFDRPSLYNYWGQGTQVTVSS |
| 130 | F024500046 K10G A14P L45R L82M K83R | EVQLVESGGGLVQPGGSLRLSCSASGRTFSFSTSTMGWFRQAPGKEREFVAAID WSDFNTYYADSVKGRFTISRHNPRNSVYLQMNSLRPEDTAVYYCAAHSETRGGT RYFDRPSLYNYWGQGTQVTVSS |
| 131 | F024500047 K10G A14P H72D L82M K83R | EVQLVESGGGLVQPGGSLRLSCSASGRTFSFSTSTMGWFRQAPGKELEFVAAID WSDFNTYYADSVKGRFTISRDNPRNSVYLQMNSLRPEDTAVYYCAAHSETRGGT RYFDRPSLYNYWGQGTQVTVSS |
| 132 | F024500048 K10G A14P P74S L82M K83R | EVQLVESGGGLVQPGGSLRLSCSASGRTFSFSTSTMGWFRQAPGKELEFVAAID WSDFNTYYADSVKGRFTISRHNSRNSVYLQMNSLRPEDTAVYYCAAHSETRGGT RYFDRPSLYNYWGQGTQVTVSS |
| 133 | F024500049 K10G A14P R75K L82M K83R | EVQLVESGGGLVQPGGSLRLSCSASGRTFSFSTSTMGWFRQAPGKELEFVAAID WSDFNTYYADSVKGRFTISRHNPKNSVYLQMNSLRPEDTAVYYCAAHSETRGGT RYFDRPSLYNYWGQGTQVTVSS |
| 134 | F024500050 K10G A14P S77T L82M K83R | EVQLVESGGGLVQPGGSLRLSCSASGRTFSFSTSTMGWFRQAPGKELEFVAAID WSDFNTYYADSVKGRFTISRHNPRNTVYLQMNSLRPEDTAVYYCAAHSETRGGT RYFDRPSLYNYWGQGTQVTVSS |
| 135 | F024500051 K10G A14P L45R H72D P74S R75K S77T L82M K83R | EVQLVESGGGLVQPGGSLRLSCSASGRTFSFSTSTMGWFRQAPGKEREFVAAID WSDFNTYYADSVKGRFTISRDNSKNTVYLQMNSLRPEDTAVYYCAAHSETRGGT RYFDRPSLYNYWGQGTQVTVSS |
| 136 | F024500016.1 A14P A74S K83R | EVQLVESGGGLVQPGGSLRLSCAASGRTFRHYAMGWFRQAPGKEREFVAAISSY GSTDYGDSVKGRFTISRDDSKNTVPLQMNSLRPEDTAVYYCAAADETLGAVPNF RLHEKYEYEYWGQGTLVTVSS |
| 137 | F024500016.2 A14P G60A A74S K83R | EVQLVESGGGLVQPGGSLRLSCAASGRTFRHYAMGWFRQAPGKEREFVAAISSY GSTDYADSVKGRFTISRDDSKNTVPLQMNSLRPEDTAVYYCAAADETLGAVPNF RLHEKYEYEYWGQGTLVTVSS |
| 138 | F024500016.3 A14P D73N A74S K83R | EVQLVESGGGLVQPGGSLRLSCAASGRTFRHYAMGWFRQAPGKEREFVAAISSY GSTDYGDSVKGRFTISRDNSKNTVPLQMNSLRPEDTAVYYCAAADETLGAVPNF RLHEKYEYEYWGQGTLVTVSS |
| 139 | F024500016.4 A14P A74S P79Y K83R | EVQLVESGGGLVQPGGSLRLSCAASGRTFRHYAMGWFRQAPGKEREFVAAISSY GSTDYGDSVKGRFTISRDDSKNTVYLQMNSLRPEDTAVYYCAAADETLGAVPNF RLHEKYEYEYWGQGTLVTVSS |
| 140 | F024500016.5 A14P G60A A74S P79Y K83R | EVQLVESGGGLVQPGGSLRLSCAASGRTFRHYAMGWFRQAPGKEREFVAAISSY GSTDYADSVKGRFTISRDDSKNTVYLQMNSLRPEDTAVYYCAAADETLGAVPNF RLHEKYEYEYWGQGTLVTVSS |
| 141 | F024500016.6 A14P G60A D73N A74S K83R | EVQLVESGGGLVQPGGSLRLSCAASGRTFRHYAMGWFRQAPGKEREFVAAISSY GSTDYADSVKGRFTISRDNSKNTVPLQMNSLRPEDTAVYYCAAADETLGAVPNF RLHEKYEYEYWGQGTLVTVSS |
| 142 | F024500016.7 A14P D73N A74S P79Y K83R | EVQLVESGGGLVQPGGSLRLSCAASGRTFRHYAMGWFRQAPGKEREFVAAISSY GSTDYGDSVKGRFTISRDNSKNTVYLQMNSLRPEDTAVYYCAAADETLGAVPNF RLHEKYEYEYWGQGTLVTVSS |
| 143 | F024500016.8 A14P G60A D73N A74S P79Y K83R | EVQLVESGGGLVQPGGSLRLSCAASGRTFRHYAMGWFRQAPGKEREFVAAISSY GSTDYADSVKGRFTISRDNSKNTVYLQMNSLRPEDTAVYYCAAADETLGAVPNF RLHEKYEYEYWGQGTLVTVSS |

Figure 2 (continued)

| SEQ ID NO | Description | Sequence |
|---|---|---|
| 147 | F024500045.1 E1D K10G A14P L82M K83R | DVQLVESGGGLVQPGGSLRLSCSASGRTFSFSTSTMGWFRQAPGKELEFVAAIDWSDFNTYYADSVKGRFTISRHNPRNSVYLQMNSLRPEDTAVYYCAAHSETRGGTRYFDRPSLYNYWGQGTQVTVSS |
| 148 | F024500046.1 E1D K10G A14P L45R L82M K83R | DVQLVESGGGLVQPGGSLRLSCSASGRTFSFSTSTMGWFRQAPGKEREFVAAIDWSDFNTYYADSVKGRFTISRHNPRNSVYLQMNSLRPEDTAVYYCAAHSETRGGTRYFDRPSLYNYWGQGTQVTVSS |
| 149 | F024500047.1 E1D K10G A14P H72D L82M K83R | DVQLVESGGGLVQPGGSLRLSCSASGRTFSFSTSTMGWFRQAPGKELEFVAAIDWSDFNTYYADSVKGRFTISRDNPRNSVYLQMNSLRPEDTAVYYCAAHSETRGGTRYFDRPSLYNYWGQGTQVTVSS |
| 150 | F024500048.1 E1D K10G A14P P74S L82M K83R | DVQLVESGGGLVQPGGSLRLSCSASGRTFSFSTSTMGWFRQAPGKELEFVAAIDWSDFNTYYADSVKGRFTISRHNSRNSVYLQMNSLRPEDTAVYYCAAHSETRGGTRYFDRPSLYNYWGQGTQVTVSS |
| 151 | F024500049.1 E1D K10G A14P R75K L82M K83R | DVQLVESGGGLVQPGGSLRLSCSASGRTFSFSTSTMGWFRQAPGKELEFVAAIDWSDFNTYYADSVKGRFTISRHNPKNSVYLQMNSLRPEDTAVYYCAAHSETRGGTRYFDRPSLYNYWGQGTQVTVSS |
| 152 | F024500050.1 E1D K10G A14P S77T L82M K83R | DVQLVESGGGLVQPGGSLRLSCSASGRTFSFSTSTMGWFRQAPGKELEFVAAIDWSDFNTYYADSVKGRFTISRHNPRNTVYLQMNSLRPEDTAVYYCAAHSETRGGTRYFDRPSLYNYWGQGTQVTVSS |
| 153 | F024500051.1 K10G A14P L45R H72D P74S R75K S77T L82M K83R | DVQLVESGGGLVQPGGSLRLSCSASGRTFSFSTSTMGWFRQAPGKEREFVAAIDWSDFNTYYADSVKGRFTISRDNSKNTVYLQMNSLRPEDTAVYYCAAHSETRGGTRYFDRPSLYNYWGQGTQVTVSS |
| 154 | F024500016.11 E1D A14P A74S K83R | DVQLVESGGGLVQPGGSLRLSCAASGRTFRHYAMGWFRQAPGKEREFVAAISSYGSTDYGDSVKGRFTISRDDSKNTVPLQMNSLRPEDTAVYYCAAADETLGAVPNFRLHEKYEYEYWGQGTLVTVSS |
| 155 | F024500016.21 E1D A14P G60A A74S K83R | DVQLVESGGGLVQPGGSLRLSCAASGRTFRHYAMGWFRQAPGKEREFVAAISSYGSTDYADSVKGRFTISRDDSKNTVPLQMNSLRPEDTAVYYCAAADETLGAVPNFRLHEKYEYEYWGQGTLVTVSS |
| 156 | F024500016.31 E1D A14P D73N A74S K83R | DVQLVESGGGLVQPGGSLRLSCAASGRTFRHYAMGWFRQAPGKEREFVAAISSYGSTDYGDSVKGRFTISRDNSKNTVPLQMNSLRPEDTAVYYCAAADETLGAVPNFRLHEKYEYEYWGQGTLVTVSS |
| 157 | F024500016.41 E1D A14P A74S P79Y K83R | DVQLVESGGGLVQPGGSLRLSCAASGRTFRHYAMGWFRQAPGKEREFVAAISSYGSTDYGDSVKGRFTISRDDSKNTVYLQMNSLRPEDTAVYYCAAADETLGAVPNFRLHEKYEYEYWGQGTLVTVSS |
| 158 | F024500016.51 E1D A14P G60A A74S P79Y K83R | DVQLVESGGGLVQPGGSLRLSCAASGRTFRHYAMGWFRQAPGKEREFVAAISSYGSTDYADSVKGRFTISRDDSKNTVYLQMNSLRPEDTAVYYCAAADETLGAVPNFRLHEKYEYEYWGQGTLVTVSS |
| 159 | F024500016.61 E1D A14P G60A D73N A74S K83R | DVQLVESGGGLVQPGGSLRLSCAASGRTFRHYAMGWFRQAPGKEREFVAAISSYGSTDYADSVKGRFTISRDNSKNTVPLQMNSLRPEDTAVYYCAAADETLGAVPNFRLHEKYEYEYWGQGTLVTVSS |
| 160 | F024500016.71 E1D A14P D73N A74S P79Y K83R | DVQLVESGGGLVQPGGSLRLSCAASGRTFRHYAMGWFRQAPGKEREFVAAISSYGSTDYGDSVKGRFTISRDNSKNTVYLQMNSLRPEDTAVYYCAAADETLGAVPNFRLHEKYEYEYWGQGTLVTVSS |
| 161 | F024500016.81 E1D A14P G60A D73N A74S P79Y K83R | DVQLVESGGGLVQPGGSLRLSCAASGRTFRHYAMGWFRQAPGKEREFVAAISSYGSTDYADSVKGRFTISRDNSKNTVYLQMNSLRPEDTAVYYCAAADETLGAVPNFRLHEKYEYEYWGQGTLVTVSS |

Figure 2 (continued)

| SEQ ID NO | Description | Sequence |
|---|---|---|
| 162 | F024500045.2 E1D K10G A14P L82M K83R +A | DVQLVESGGGLVQPGGSLRLSCSASGRTFSFSTSTMGWFRQAPGKELEFVAAID WSDFNTYYADSVKGRFTISRHNPRNSVYLQMNSLRPEDTAVYYCAAHSETRGGT RYFDRPSLYNYWGQGTQVTVSSA |
| 163 | F024500046.2 E1D K10G A14P L45R L82M K83R +A | DVQLVESGGGLVQPGGSLRLSCSASGRTFSFSTSTMGWFRQAPGKEREFVAAID WSDFNTYYADSVKGRFTISRHNPRNSVYLQMNSLRPEDTAVYYCAAHSETRGGT RYFDRPSLYNYWGQGTQVTVSSA |
| 164 | F024500047.2 E1D K10G A14P H72D L82M K83R +A | DVQLVESGGGLVQPGGSLRLSCSASGRTFSFSTSTMGWFRQAPGKELEFVAAID WSDFNTYYADSVKGRFTISRDNPRNSVYLQMNSLRPEDTAVYYCAAHSETRGGT RYFDRPSLYNYWGQGTQVTVSSA |
| 165 | F024500048.2 E1D K10G A14P P74S L82M K83R +A | DVQLVESGGGLVQPGGSLRLSCSASGRTFSFSTSTMGWFRQAPGKELEFVAAID WSDFNTYYADSVKGRFTISRHNSRNSVYLQMNSLRPEDTAVYYCAAHSETRGGT RYFDRPSLYNYWGQGTQVTVSSA |
| 166 | F024500049.2 E1D K10G A14P R75K L82M K83R +A | DVQLVESGGGLVQPGGSLRLSCSASGRTFSFSTSTMGWFRQAPGKELEFVAAID WSDFNTYYADSVKGRFTISRHNPKNSVYLQMNSLRPEDTAVYYCAAHSETRGGT RYFDRPSLYNYWGQGTQVTVSSA |
| 167 | F024500050.2 E1D K10G A14P S77T L82M K83R +A | DVQLVESGGGLVQPGGSLRLSCSASGRTFSFSTSTMGWFRQAPGKELEFVAAID WSDFNTYYADSVKGRFTISRHNPRNTVYLQMNSLRPEDTAVYYCAAHSETRGGT RYFDRPSLYNYWGQGTQVTVSSA |
| 168 | F024500051.2 K10G A14P L45R H72D P74S R75K S77T L82M K83R +A | DVQLVESGGGLVQPGGSLRLSCSASGRTFSFSTSTMGWFRQAPGKEREFVAAID WSDFNTYYADSVKGRFTISRDNSKNTVYLQMNSLRPEDTAVYYCAAHSETRGGT RYFDRPSLYNYWGQGTQVTVSSA |
| 169 | F024500016.12 E1D A14P A74S K83R +A | DVQLVESGGGLVQPGGSLRLSCAASGRTFRHYAMGWFRQAPGKEREFVAAISSY GSTDYGDSVKGRFTISRDDSKNTVPLQMNSLRPEDTAVYYCAAADETLGAVPNF RLHEKYEYEYWGQGTLVTVSSA |
| 170 | F024500016.22 E1D A14P G60A A74S K83R +A | DVQLVESGGGLVQPGGSLRLSCAASGRTFRHYAMGWFRQAPGKEREFVAAISSY GSTDYADSVKGRFTISRDDSKNTVPLQMNSLRPEDTAVYYCAAADETLGAVPNF RLHEKYEYEYWGQGTLVTVSSA |
| 171 | F024500016.32 E1D A14P D73N A74S K83R +A | DVQLVESGGGLVQPGGSLRLSCAASGRTFRHYAMGWFRQAPGKEREFVAAISSY GSTDYGDSVKGRFTISRDNSKNTVPLQMNSLRPEDTAVYYCAAADETLGAVPNF RLHEKYEYEYWGQGTLVTVSSA |
| 172 | F024500016.42 E1D A14P A74S P79Y K83R +A | DVQLVESGGGLVQPGGSLRLSCAASGRTFRHYAMGWFRQAPGKEREFVAAISSY GSTDYGDSVKGRFTISRDDSKNTVYLQMNSLRPEDTAVYYCAAADETLGAVPNF RLHEKYEYEYWGQGTLVTVSSA |
| 173 | F024500016.52 E1D A14P G60A A74S P79Y K83R +A | DVQLVESGGGLVQPGGSLRLSCAASGRTFRHYAMGWFRQAPGKEREFVAAISSY GSTDYADSVKGRFTISRDDSKNTVYLQMNSLRPEDTAVYYCAAADETLGAVPNF RLHEKYEYEYWGQGTLVTVSSA |
| 174 | F024500016.62 E1D A14P G60A D73N A74S K83R +A | DVQLVESGGGLVQPGGSLRLSCAASGRTFRHYAMGWFRQAPGKEREFVAAISSY GSTDYADSVKGRFTISRDNSKNTVPLQMNSLRPEDTAVYYCAAADETLGAVPNF RLHEKYEYEYWGQGTLVTVSSA |
| 175 | F024500016.72 E1D A14P D73N A74S P79Y K83R +A | DVQLVESGGGLVQPGGSLRLSCAASGRTFRHYAMGWFRQAPGKEREFVAAISSY GSTDYGDSVKGRFTISRDNSKNTVYLQMNSLRPEDTAVYYCAAADETLGAVPNF RLHEKYEYEYWGQGTLVTVSSA |
| 176 | F024500016.82 E1D A14P G60A D73N A74S P79Y K83R +A | DVQLVESGGGLVQPGGSLRLSCAASGRTFRHYAMGWFRQAPGKEREFVAAISSY GSTDYADSVKGRFTISRDNSKNTVYLQMNSLRPEDTAVYYCAAADETLGAVPNF RLHEKYEYEYWGQGTLVTVSSA |

Figure 3A

```
                         20                        40                        60
                         |                         |                         |
SEQIDNO:1   EVQLVESGGG LVQPGGSLRL SCAASGRTFR HYAMGWFRQA PGKEREFVAA ISSYGSTDYG  60
SEQIDNO:15  .......... .......... .......... .......... .......... ..........  60
SEQIDNO:16  .......... V......... .......... .......... .......... ..........  60
SEQIDNO:17  .......... V......... .......... .......... .......... ..........  60
SEQIDNO:18  .......... V......... .......... .......... .......... ..........  60
SEQIDNO:19  .......... V......... .......... .......... .......... ..........  60
SEQIDNO:20  .......... .......... .......... .......... .......... ..........  60
SEQIDNO:21  .......... .......... .......... .......... .......... ..........  60
SEQIDNO:22  .......... .......... .......... .......... .......... ..........  60
SEQIDNO:23  .......... .......... .......... .......... .......... ..........  60
SEQIDNO:24  .......... V......... .......... .......... .......... ..........  60
SEQIDNO:25  .......... V......... .......... .......... .......... ..........  60
SEQIDNO:26  .......... V......... .......... .......... .......... ..........  60
SEQIDNO:27  .......... V......... .......... .......... .......... ..........  60
SEQIDNO:28  .......... V......... .......... .......... .......... ..........  60
SEQIDNO:29  .......... .......... .......... .......... .......... ..........  60
SEQIDNO:30  .......... V......... .......... .......... .......... ..........  60
SEQIDNO:31  .......... V......... .......... .......... .......... ..........  60
SEQIDNO:32  .......... V......... .......... .......... .......... ..........  60
SEQIDNO:33  .......... V......... .......... .......... .......... ..........  60
SEQIDNO:34  .......... .......... .......... .......... .......... ..........  60
SEQIDNO:35  .......... .......... .......... .......... .......... ..........  60
SEQIDNO:36  .......... .......... .......... .......... .......... ..........  60
SEQIDNO:37  .......... .......... .......... .......... .......... ..........  60
SEQIDNO:38  .......... V......... .......... .......... .......... ..........  60
SEQIDNO:39  .......... V......... .......... .......... .......... ..........  60
SEQIDNO:40  .......... V......... .......... .......... .......... ..........  60
SEQIDNO:41  .......... V......... .......... .......... .......... ..........  60
SEQIDNO:42  .......... V......... .......... .......... .......... ..........  60
SEQIDNO:87  .......... ...A...... .......... .......... .......... ..........  60

80                        100                       120
                         |                         |                         |
SEQIDNO:1   DSVKGRFTIS RDDAKNTVPL QMNSLKPEDT AVYYCAAADE TLGAVPNFRL HEKYEYEYWG 120
SEQIDNO:15  .......... .......... .......... .T........ .......... .......... 120
SEQIDNO:16  .......... .......... .......... .......... .......... .......... 120
SEQIDNO:17  .......... .......... .......... .......... .......... .......... 120
SEQIDNO:18  .......... .......... .......... .......... .......... .......... 120
SEQIDNO:19  .......... .......... .......... .......... .......... .......... 120
SEQIDNO:20  .......... .......... .......... .L........ .......... .......... 120
SEQIDNO:21  .......... .......... .......... .L........ .......... .......... 120
SEQIDNO:22  .......... .......... .......... .L........ .......... .......... 120
SEQIDNO:23  .......... .......... .......... .L........ .......... .......... 120
SEQIDNO:24  .......... .......... .......... .L........ .......... .......... 120
SEQIDNO:25  .......... .......... .......... .L........ .......... .......... 120
SEQIDNO:26  .......... .......... .......... .L........ .......... .......... 120
SEQIDNO:27  .......... .......... .......... .L........ .......... .......... 120
SEQIDNO:28  .......... .......... .......... .L........ .......... .......... 120
SEQIDNO:29  .......... .......... .......... .T........ .......... .......... 120
SEQIDNO:30  .......... .......... .......... .......... .......... .......... 120
SEQIDNO:31  .......... .......... .......... .......... .......... .......... 120
SEQIDNO:32  .......... .......... .......... .......... .......... .......... 120
SEQIDNO:33  .......... .......... .......... .......... .......... .......... 120
SEQIDNO:34  .......... .......... .......... .L........ .......... .......... 120
SEQIDNO:35  .......... .......... .......... .L........ .......... .......... 120
SEQIDNO:36  .......... .......... .......... .L........ .......... .......... 120
SEQIDNO:37  .......... .......... .......... .L........ .......... .......... 120
SEQIDNO:38  .......... .......... .......... .L........ .......... .......... 120
SEQIDNO:39  .......... .......... .......... .L........ .......... .......... 120
SEQIDNO:40  .......... .......... .......... .L........ .......... .......... 120
SEQIDNO:41  .......... .......... .......... .L........ .......... .......... 120
SEQIDNO:42  .......... .......... .......... .L........ .......... .......... 120
SEQIDNO:87  .......... .......... .......... .......... .......... .......... 120
```

Figure 3A (continued)

```
SEQIDNO:1   QGTLVTVSS- 129
SEQIDNO:15  .........- 129
SEQIDNO:16  .....K...- 129
SEQIDNO:17  .....Q...- 129
SEQIDNO:18  .......K.- 129
SEQIDNO:19  .......Q.- 129
SEQIDNO:20  .....K...- 129
SEQIDNO:21  .....Q...- 129
SEQIDNO:22  .......K.- 129
SEQIDNO:23  .......Q.- 129
SEQIDNO:24  .........- 129
SEQIDNO:25  .....K...- 129
SEQIDNO:26  .....Q...- 129
SEQIDNO:27  .......K.- 129
SEQIDNO:28  .......Q.- 129
SEQIDNO:29  .........A 130
SEQIDNO:30  .....K...A 130
SEQIDNO:31  .....Q...A 130
SEQIDNO:32  .......K.A 130
SEQIDNO:33  .......Q.A 130
SEQIDNO:34  .....K...A 130
SEQIDNO:35  .....Q...A 130
SEQIDNO:36  .......K.A 130
SEQIDNO:37  .......Q.A 130
SEQIDNO:38  .........A 130
SEQIDNO:39  .....K...A 130
SEQIDNO:40  .....Q...A 130
SEQIDNO:41  .......K.A 130
SEQIDNO:42  .......Q.A 130
SEQIDNO:67  ...Q.....- 129
```

Figure 3B

```
                         20                   40                   60
                          |                    |                    |
SEQIDNO:8   EVQLVESGGK LVQPGGSLRL SCSASGRTFS FSTSTMGWFR QAPGKELEFV AAIDWSDFNT 60
SEQIDNO:43  .......... .......... .......... .......... .......... .......... 60
SEQIDNO:44  .......... V......... .......... .......... .......... .......... 60
SEQIDNO:45  .......... V......... .......... .......... .......... .......... 60
SEQIDNO:46  .......... V......... .......... .......... .......... .......... 60
SEQIDNO:47  .......... V......... .......... .......... .......... .......... 60
SEQIDNO:48  .......... .......... .......... .......... .......... .......... 60
SEQIDNO:49  .......... .......... .......... .......... .......... .......... 60
SEQIDNO:50  .......... .......... .......... .......... .......... .......... 60
SEQIDNO:51  .......... .......... .......... .......... .......... .......... 60
SEQIDNO:52  .......... V......... .......... .......... .......... .......... 60
SEQIDNO:53  .......... V......... .......... .......... .......... .......... 60
SEQIDNO:54  .......... V......... .......... .......... .......... .......... 60
SEQIDNO:55  .......... V......... .......... .......... .......... .......... 60
SEQIDNO:56  .......... V......... .......... .......... .......... .......... 60
SEQIDNO:57  .......... .......... .......... .......... .......... .......... 60
SEQIDNO:58  .......... V......... .......... .......... .......... .......... 60
SEQIDNO:59  .......... V......... .......... .......... .......... .......... 60
SEQIDNO:60  .......... V......... .......... .......... .......... .......... 60
SEQIDNO:61  .......... V......... .......... .......... .......... .......... 60
SEQIDNO:62  .......... .......... .......... .......... .......... .......... 60
SEQIDNO:63  .......... .......... .......... .......... .......... .......... 60
SEQIDNO:64  .......... .......... .......... .......... .......... .......... 60
SEQIDNO:65  .......... .......... .......... .......... .......... .......... 60
SEQIDNO:66  .......... V......... .......... .......... .......... .......... 60
SEQIDNO:67  .......... V......... .......... .......... .......... .......... 60
SEQIDNO:68  .......... V......... .......... .......... .......... .......... 60
SEQIDNO:69  .......... V......... .......... .......... .......... .......... 60
SEQIDNO:70  .......... V......... .......... .......... .......... .......... 60
SEQIDNO:88  .......... ..A....... .......... .......... .......... .......... 60

80                   100                  120
                          |                    |                    |
SEQIDNO:8   YYADSVKGRF TISRHNPRNS VYLQLNSLKP EDTAVYYCAA HSETRGGTRY FDRPSLYNYW 120
SEQIDNO:43  .......... .......... .......... ...T...... .......... .......... 120
SEQIDNO:44  .......... .......... .......... .......... .......... .......... 120
SEQIDNO:45  .......... .......... .......... .......... .......... .......... 120
SEQIDNO:46  .......... .......... .......... .......... .......... .......... 120
SEQIDNO:47  .......... .......... .......... .......... .......... .......... 120
SEQIDNO:48  .......... .......... .......... ....L..... .......... .......... 120
SEQIDNO:49  .......... .......... .......... ....L..... .......... .......... 120
SEQIDNO:50  .......... .......... .......... ....L..... .......... .......... 120
SEQIDNO:51  .......... .......... .......... ....L..... .......... .......... 120
SEQIDNO:52  .......... .......... .......... ....L..... .......... .......... 120
SEQIDNO:53  .......... .......... .......... ....L..... .......... .......... 120
SEQIDNO:54  .......... .......... .......... ....L..... .......... .......... 120
SEQIDNO:55  .......... .......... .......... ....L..... .......... .......... 120
SEQIDNO:56  .......... .......... .......... ....L..... .......... .......... 120
SEQIDNO:57  .......... .......... .......... ....T..... .......... .......... 120
SEQIDNO:58  .......... .......... .......... .......... .......... .......... 120
SEQIDNO:59  .......... .......... .......... .......... .......... .......... 120
SEQIDNO:60  .......... .......... .......... .......... .......... .......... 120
SEQIDNO:61  .......... .......... .......... .......... .......... .......... 120
SEQIDNO:62  .......... .......... .......... ....L..... .......... .......... 120
SEQIDNO:63  .......... .......... .......... ....L..... .......... .......... 120
SEQIDNO:64  .......... .......... .......... ....L..... .......... .......... 120
SEQIDNO:65  .......... .......... .......... ....L..... .......... .......... 120
SEQIDNO:66  .......... .......... .......... ....L..... .......... .......... 120
SEQIDNO:67  .......... .......... .......... ....L..... .......... .......... 120
SEQIDNO:68  .......... .......... .......... ....L..... .......... .......... 120
SEQIDNO:69  .......... .......... .......... ....L..... .......... .......... 120
SEQIDNO:70  .......... .......... .......... ....L..... .......... .......... 120
SEQIDNO:88  .......... .......... .......... .......... .......... .......... 120
```

Figure 3B (continued)

```
SEQIDNO:8   GQGTLVTVSS  - 130
SEQIDNO:43  ..........  - 130
SEQIDNO:44  ......K...  - 130
SEQIDNO:45  ......Q...  - 130
SEQIDNO:46  ........K.  - 130
SEQIDNO:47  ........Q.  - 130
SEQIDNO:48  ......K...  - 130
SEQIDNO:49  ......Q...  - 130
SEQIDNO:50  ........K.  - 130
SEQIDNO:51  ........Q.  - 130
SEQIDNO:52  ..........  - 130
SEQIDNO:53  ......K...  - 130
SEQIDNO:54  ......Q...  - 130
SEQIDNO:55  ........K.  - 130
SEQIDNO:56  ........Q.  - 130
SEQIDNO:57  ..........  A 131
SEQIDNO:58  ......K...  A 131
SEQIDNO:59  ......Q...  A 131
SEQIDNO:60  ........K.  A 131
SEQIDNO:61  ........Q.  A 131
SEQIDNO:62  ......K...  A 131
SEQIDNO:63  ......Q...  A 131
SEQIDNO:64  ........K.  A 131
SEQIDNO:65  ........Q.  A 131
SEQIDNO:66  ..........  A 131
SEQIDNO:67  ......K...  A 131
SEQIDNO:68  ......Q...  A 131
SEQIDNO:69  ........K.  A 131
SEQIDNO:70  ........Q.  A 131
SEQIDNO:86  ....Q.....  - 130
```

Figure 4A

| SEQ ID NO | Sequence |
|---|---|
| 93 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 94 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 95 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 96 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 97 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 98 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 144 | DVQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVSSGGGGSGGGGSGGGGSGGGGSGGGGSGGGGSEVQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |

Figure 4B

| SEQ ID NO | Sequence |
|---|---|
| 99 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 100 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 101 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 102 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 103 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 104 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 145 | DVQLVESGGKLVQAGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVSSGGGGSGGGGSGGGGSGGGGSGGGGSGGGGSEVQLVESGGKLVQAGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |

Figure 4C

| SEQ ID NO | Sequence |
|---|---|
| 105 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVTVSSGGGGSGGG SEVQLVESGGGLVQPGNSLRLSCAASGFTFSSFGMSWVRQAPGKGLEWVSSISGSGSDTLY ADSVKGRFTISRDNAKTTLYLQMNSLRPEDTAVYYCTIGGSLSRSSQGTLVTVSSA |
| 106 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVTVSSGGGGSGGG SEVQLVESGGGVVQPGNSLRLSCAASGFTFSSFGMSWVRQAPGKGLEWVSSISGSGSDTLY ADSVKGRFTISRDNAKTTLYLQMNSLRPEDTALYYCTIGGSLSRSSQGTLVTVSSA |
| 107 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVTVSSGGGGSGGG SEVQLVESGGGVVQPGNSLRLSCAASGFTFSSFGMSWVRQAPGKGLEWVSSISGSGSDTLY ADSVKGRFTISRDNAKTTLYLQMNSLRPEDTALYYCTIGGSLSRSSQGTLVKVSSA |
| 108 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVKVSSGGGGSGG GSEVQLVESGGGLVQPGNSLRLSCAASGFTFSSFGMSWVRQAPGKGLEWVSSISGSGSDTL YADSVKGRFTISRDNAKTTLYLQMNSLRPEDTAVYYCTIGGSLSRSSQGTLVTVSSA |
| 109 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVKVSSGGGGSGG GSEVQLVESGGGVVQPGNSLRLSCAASGFTFSSFGMSWVRQAPGKGLEWVSSISGSGSDTL YADSVKGRFTISRDNAKTTLYLQMNSLRPEDTALYYCTIGGSLSRSSQGTLVTVSSA |
| 110 | DVQLVESGGGVVQPGGSLRLSCAASGRTFRHYAMGWFRQAPGKEREFVAAISSYGSTDYG DSVKGRFTISRDDAKNTVPLQMNSLKPEDTALYYCAAADETLGAVPNFRLHEKYEYEYWG QGTLVTVSSGGGGSGGGGSGGGGSGGGGSGGGGSGGGGEVQLVESGGKVVQPGG SLRLSCSASGRTFSFSTSTMGWFRQAPGKELEFVAAIDWSDFNTYYADSVKGRFTISRHNPR NSVYLQLNSLKPEDTALYYCAAHSETRGGTRYFDRPSLYNYWGQGTLVKVSSGGGGSGG GSEVQLVESGGGVVQPGNSLRLSCAASGFTFSSFGMSWVRQAPGKGLEWVSSISGSGSDTL YADSVKGRFTISRDNAKTTLYLQMNSLRPEDTALYYCTIGGSLSRSSQGTLVKVSSA |

Figure 4C (continued)

| SEQ ID NO | Sequence |
|---|---|
| 111 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 112 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 113 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 114 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 115 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 116 | DVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGGSGGGGSGGGGSGGGGSGGGGEVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |

Figure 4C (continued)

| SEQ ID NO | Sequence |
|---|---|
| 117 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 118 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 119 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 120 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 121 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 122 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVTVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |

Figure 4C (continued)

| SEQ ID NO | Sequence |
|---|---|
| 123 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 124 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| 125 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVTVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 126 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 127 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| 128 | DVQLVESGGKVVQPGGSLRLSCSASGRTFSFSTSTMGWFRQAPGKELEFVAAIDWSDFNTYYADSVKGRFTISRHNPRNSVYLQLNSLKPEDTALYYCAAHSETRGGTRYFDRPSLYNYWGQGTLVKVSSGGGGSGGGGSGGGGSGGGGSGGGGSGGGGSGGGGEVQLVESGGGVVQPGGSLRLSCAASGRTFRHYAMGWFRQAPGKEREFVAAISSYGSTDYGDSVKGRFTISRDDAKNTVPLQMNSLKPEDTALYYCAAADETLGAVPNFRLHEKYEYEYWGQGTLVKVSSGGGGSGGGSEVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVKVSSA |
| 146 | DVQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVSSGGGGSGGGGSGGGGSGGGGSGGGGSGGGGSGGGGSEVQLVESGGKLVQAGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |

Figure 6

| Sample | REFERENCE A | REFERENCE A(L11V,V89L)-A | REFERENCE A(L11V,V89L,T110K)-A | REFERENCE A(L11V,V89L)-A | REFERENCE A(L11V,V89L,T110K)-A |
|---|---|---|---|---|---|
| IHuS#ABL-0042-02 | -13 | -16 | -19 | | |
| IHuS#ABL-0088-03 | 163 | 3 | -7 | 98 | 100 |
| IHuS#ABL-0137-01 | -2 | -5 | -3 | | |
| IHuS#ABL-0138-01 | 1 | -6 | -9 | | |
| IHuS#ABL-0139-01 | 44 | 17 | -8 | 61 | 100 |
| IHuS#ABL-0141-01 | 22 | 7 | -4 | 70 | 100 |
| IHuS#ABL-0149-01 | 41 | -18 | -22 | 100 | 100 |
| IHuS#ABL-0150-01 | 49 | 2 | 1 | 95 | 98 |
| IHuS#ABL-0151-01 | 123 | 2 | 0 | 99 | 100 |
| IHuS#ABL-0152-01 | 33 | -3 | -6 | 100 | 100 |
| IHuS#ABL-0153-01 | 118 | 11 | -12 | 90 | 100 |
| IHuS#ABL-0154-01 | 10 | -1 | -9 | | |
| IHuS#ABL-0159-01 | -3 | -19 | -24 | | |
| IHuS#ABL-0160-01 | 9 | -8 | -5 | | |
| IHuS#ABL-0161-01 | -2 | -3 | -3 | | |
| IHuS#ABL-0162-01 | -15 | -7 | -9 | | |
| IHuS#ABL-0148-01 | 303 | 17 | -6 | 94 | 100 |
| IHuS#ABL-0163-01 | 278 | 19 | -12 | 93 | 100 |
| IHuS#ABL-0171-01 | 9 | 19 | 5 | | |
| IHuS#ABL-0172-01 | 60 | -6 | -5 | 100 | 100 |
| IHuS#ABL-0218-01 | 60 | -2 | 4 | 100 | 94 |
| IHuS#ABL-0040-03 | 261 | 1 | -11 | 100 | 100 |
| IHuS#ABL-0090-02 | 360 | 26 | -17 | 93 | 100 |
| IHuS#ABL-0173-01 | 171 | 6 | -3 | 96 | 100 |
| IHuS#ABL-0188-01 | 0 | -16 | -18 | | |
| IHuS#ABL-0006-02 | 414 | 53 | 27 | 87 | 93 |
| IHuS#ABL-0189-01 | 6 | 2 | 1 | | |
| IHuS#ABL-0190-01 | -9 | -6 | -11 | | |
| IHuS#ABL-0191-01 | -1 | 11 | -6 | | |
| IHuS#ABL-0192-01 | 31 | 5 | -9 | 84 | 100 |
| IHuS#ABL-0198-01 | 14 | -9 | -17 | | |
| IHuS#ABL-0165-01 | 260 | -1 | -1 | 100 | 100 |
| IHuS#ABL-0199-01 | 248 | 39 | 4 | 84 | 99 |
| IHuS#ABL-0200-01 | 11 | -3 | -9 | | |
| IHuS#ABL-0201-01 | 54 | 25 | -8 | 53 | 100 |
| IHuS#ABL-0202-01 | 86 | 9 | -8 | 89 | 100 |
| IHuS#ABL-0044-02 | -12 | -16 | -20 | | |
| IHuS#ABL-0209-01 | 31 | 0 | -1 | 99 | 100 |

Figure 6 (continued)

| Sample | REFERENCE A | REFERENCE A(L11V,V89L)-A | REFERENCE A(L11V,V89L,T110K)-A | REFERENCE A(L11V,V89L)-A | REFERENCE A(L11V,V89L,T110K)-A |
|---|---|---|---|---|---|
| IHuS#ABL-0210-01 | 26 | 1 | 4 | 97 | 83 |
| IHuS#ABL-0211-01 | 37 | -3 | -8 | 100 | 100 |
| IHuS#ABL-0212-01 | 133 | 26 | 8 | 80 | 94 |
| IHuS#ABL-0213-01 | 26 | 58 | 55 | -125 | -113 |
| IHuS#ABL-0183-01 | 274 | -8 | -16 | 100 | 100 |
| IHuS#ABL-0005-06 | 10 | -6 | -7 | | |
| IHuS#ABL-0219-01 | 16 | -2 | -3 | | |
| IHuS#ABL-0221-01 | 12 | -12 | -15 | | |
| IHuS#ABL-0222-01 | 147 | 19 | 4 | 87 | 97 |
| IHuS#ABL-0223-01 | 258 | -3 | -15 | 100 | 100 |
| IHuS#ABL-0142-01 | 21 | -14 | -15 | 100 | 100 |
| IHuS#ABL-0143-01 | 30 | 1 | 11 | 98 | 63 |
| IHuS#ABL-0144-01 | 39 | -4 | -5 | 100 | 100 |
| IHuS#ABL-0145-01 | 55 | -6 | -5 | 100 | 100 |
| IHuS#ABL-0146-01 | 55 | 3 | -10 | 94 | 100 |
| IHuS#ABL-0147-01 | 111 | -7 | -12 | 100 | 100 |
| IHuS#ABL-0031-04 | 46 | -3 | -6 | 100 | 100 |
| IHuS#ABL-0047-02 | 26 | -11 | -9 | 100 | 100 |
| IHuS#ABL-0155-01 | 30 | -2 | -2 | 100 | 100 |
| IHuS#ABL-0156-01 | 43 | -5 | -5 | 100 | 100 |
| IHuS#ABL-0157-01 | 243 | 7 | -6 | 97 | 100 |
| IHuS#ABL-0158-01 | 214 | 4 | -4 | 98 | 100 |
| IHuS#ABL-0164-01 | -13 | -15 | -17 | | |
| IHuS#ABL-0166-01 | -2 | -8 | -6 | | |
| IHuS#ABL-0167-01 | 184 | 62 | 27 | 67 | 85 |
| IHuS#ABL-0168-01 | -19 | -12 | -8 | | |
| IHuS#ABL-0169-01 | 19 | 4 | -10 | | |
| IHuS#ABL-0170-01 | 214 | 3 | -4 | 98 | 100 |
| IHuS#ABL-0174-01 | -5 | -17 | -21 | | |
| IHuS#ABL-0175-01 | 66 | 26 | 5 | 60 | 93 |
| IHuS#ABL-0176-01 | 12 | -1 | -1 | | |
| IHuS#ABL-0177-01 | 4 | -6 | -7 | | |
| IHuS#ABL-0178-01 | 4 | 8 | -10 | | |
| IHuS#ABL-0179-01 | 31 | 2 | -4 | 95 | 100 |
| IHuS#ABL-0193-01 | 166 | -15 | -15 | 100 | 100 |
| IHuS#ABL-0194-01 | 64 | -13 | -11 | 100 | 100 |
| IHuS#ABL-0195-01 | 280 | 5 | 2 | 98 | 99 |
| IHuS#ABL-0196-01 | -16 | -14 | -12 | | |

Figure 6 (continued)

| Sample | REFERENCE A | REFERENCE A(L11V,V89L)-A | REFERENCE A(L11V,V89L,T110K)-A | REFERENCE A(L11V,V89L)-A | REFERENCE A(L11V,V89L,T110K)-A |
|---|---|---|---|---|---|
| IHuS#ABL-0180-01 | 9 | 7 | -6 | | |
| IHuS#ABL-0197-01 | 14 | -4 | -5 | | |
| IHuS#ABL-0204-01 | -10 | -14 | -16 | | |
| IHuS#ABL-0206-01 | 194 | 14 | -5 | 93 | 100 |
| IHuS#ABL-0207-01 | 62 | 7 | 5 | 89 | 92 |
| IHuS#ABL-0012-03 | -8 | -6 | -9 | | |
| IHuS#ABL-0208-01 | 335 | 59 | -13 | 83 | 100 |
| IHuS#ABL-0220-01 | 41 | 3 | 5 | 92 | 88 |
| IHuS#ABL-0214-01 | -3 | -15 | -23 | | |
| IHuS#ABL-0215-01 | -3 | -11 | -10 | | |
| IHuS#ABL-0181-01 | -2 | 18 | -3 | | |
| IHuS#ABL-0216-01 | -5 | -7 | -10 | | |
| IHuS#ABL-0217-01 | 45 | 2 | -11 | 95 | 100 |
| IHuS#ABL-0140-01 | 54 | 1 | -3 | 98 | 100 |
| IHuS#ABL-0224-01 | -10 | -9 | -16 | | |
| IHuS#ABL-0182-01 | 11 | -15 | -17 | | |
| IHuS#ABL-0226-01 | 4 | 6 | 3 | | |
| IHuS#ABL-0227-01 | 41 | -3 | -6 | 100 | 100 |
| IHuS#ABL-0205-01 | 33 | 10 | -8 | 71 | 100 |
| IHuS#ABL-0060-03 | 46 | 3 | -5 | 94 | 100 |

Figure 8

| Sample | REFERENCE B | REFERENCE B(L11V,V89L)-A | REFERENCE B(L11V,V89L,T110K)-A | REFERENCE B(L11V,V89L)-A | REFERENCE B(L11V,V89L,T110K)-A |
|---|---|---|---|---|---|
| IHuS#ABL-0042-02 | -8 | -11 | -11 | | |
| IHuS#ABL-0088-03 | 119 | -3 | -16 | 100 | 100 |
| IHuS#ABL-0137-01 | -7 | -12 | -14 | | |
| IHuS#ABL-0138-01 | 11 | -9 | -12 | | |
| IHuS#ABL-0139-01 | 28 | -2 | 14 | 100 | 48 |
| IHuS#ABL-0141-01 | -4 | -14 | -11 | | |
| IHuS#ABL-0149-01 | 53 | -14 | -17 | 100 | 100 |
| IHuS#ABL-0150-01 | 37 | -5 | -13 | 100 | 100 |
| IHuS#ABL-0151-01 | 103 | -10 | -14 | 100 | 100 |
| IHuS#ABL-0152-01 | 29 | -7 | -10 | 100 | 100 |
| IHuS#ABL-0153-01 | 111 | -6 | -2 | 100 | 100 |
| IHuS#ABL-0154-01 | -16 | -18 | -16 | | |
| IHuS#ABL-0159-01 | 0 | -19 | -9 | | |
| IHuS#ABL-0160-01 | 0 | -6 | -14 | | |
| IHuS#ABL-0161-01 | 86 | 67 | 52 | 22 | 39 |
| IHuS#ABL-0162-01 | -8 | -10 | -13 | | |
| IHuS#ABL-0148-01 | 296 | -6 | -8 | 100 | 100 |
| IHuS#ABL-0163-01 | 276 | 20 | -12 | 93 | 100 |
| IHuS#ABL-0171-01 | -9 | -13 | -15 | | |
| IHuS#ABL-0172-01 | 53 | -7 | -14 | 100 | 100 |
| IHuS#ABL-0218-01 | 51 | -14 | -15 | 100 | 100 |
| IHuS#ABL-0040-03 | 239 | 4 | -9 | 98 | 100 |
| IHuS#ABL-0090-02 | 376 | 9 | -18 | 98 | 100 |
| IHuS#ABL-0173-01 | 141 | -10 | -10 | 100 | 100 |
| IHuS#ABL-0188-01 | -2 | -12 | -11 | | |
| IHuS#ABL-0006-02 | 405 | 138 | -12 | 66 | 100 |
| IHuS#ABL-0189-01 | -1 | -14 | -19 | | |
| IHuS#ABL-0190-01 | -7 | -9 | -11 | | |
| IHuS#ABL-0191-01 | -5 | -6 | -8 | | |
| IHuS#ABL-0192-01 | -1 | -14 | -12 | | |
| IHuS#ABL-0198-01 | 11 | -6 | -12 | | |
| IHuS#ABL-0165-01 | 235 | -3 | -15 | 100 | 100 |
| IHuS#ABL-0199-01 | 262 | 32 | -8 | 88 | 100 |
| IHuS#ABL-0200-01 | 14 | -8 | 22 | | |
| IHuS#ABL-0201-01 | 56 | 4 | -12 | 92 | 100 |
| IHuS#ABL-0202-01 | 40 | -16 | -17 | 100 | 100 |
| IHuS#ABL-0044-02 | -19 | -19 | -20 | | |

Figure 8 (continued)

| Sample | REFERENCE B | REFERENCE B(L11V,V89L)-A | REFERENCE B(L11V,V89L,T110K)-A | REFERENCE B(L11V,V89L)-A | REFERENCE B(L11V,V89L,T110K)-A |
|---|---|---|---|---|---|
| IHuS#ABL-0209-01 | 29 | 1 | -11 | 98 | 100 |
| IHuS#ABL-0210-01 | -2 | -13 | -14 | | |
| IHuS#ABL-0211-01 | 46 | -7 | -11 | 100 | 100 |
| IHuS#ABL-0212-01 | 139 | 16 | 10 | 88 | 93 |
| IHuS#ABL-0213-01 | -5 | -11 | -13 | | |
| IHuS#ABL-0183-01 | 305 | 5 | -9 | 98 | 100 |
| IHuS#ABL-0005-06 | 9 | -1 | -15 | | |
| IHuS#ABL-0219-01 | 9 | -8 | -17 | | |
| IHuS#ABL-0221-01 | 40 | -4 | -12 | 100 | 100 |
| IHuS#ABL-0222-01 | 146 | -6 | -9 | 100 | 100 |
| IHuS#ABL-0223-01 | 276 | -13 | -16 | 100 | 100 |
| IHuS#ABL-0142-01 | 26 | 1 | -5 | 98 | 100 |
| IHuS#ABL-0143-01 | 27 | -6 | -15 | 100 | 100 |
| IHuS#ABL-0144-01 | 75 | -8 | -14 | 100 | 100 |
| IHuS#ABL-0145-01 | 64 | -6 | -8 | 100 | 100 |
| IHuS#ABL-0146-01 | 57 | -7 | -10 | 100 | 100 |
| IHuS#ABL-0147-01 | 83 | -15 | -16 | 100 | 100 |
| IHuS#ABL-0031-04 | 69 | 96 | 82 | -39 | -19 |
| IHuS#ABL-0047-02 | 20 | -12 | -17 | | |
| IHuS#ABL-0155-01 | 28 | -11 | -13 | 100 | 100 |
| IHuS#ABL-0156-01 | 62 | -5 | -12 | 100 | 100 |
| IHuS#ABL-0157-01 | 248 | -5 | -8 | 100 | 100 |
| IHuS#ABL-0158-01 | 213 | -10 | -9 | 100 | 100 |
| IHuS#ABL-0164-01 | -13 | -11 | -11 | | |
| IHuS#ABL-0166-01 | -11 | -10 | -12 | | |
| IHuS#ABL-0167-01 | 110 | 7 | -19 | 94 | 100 |
| IHuS#ABL-0168-01 | -11 | -11 | 45 | | |
| IHuS#ABL-0169-01 | 14 | -6 | -11 | | |
| IHuS#ABL-0170-01 | 201 | -10 | -10 | 100 | 100 |
| IHuS#ABL-0174-01 | -4 | -12 | -13 | | |
| IHuS#ABL-0175-01 | 38 | 4 | -14 | 90 | 100 |
| IHuS#ABL-0176-01 | -1 | -13 | -18 | | |
| IHuS#ABL-0177-01 | 4 | -10 | -10 | | |
| IHuS#ABL-0178-01 | 2 | 2 | -7 | | |
| IHuS#ABL-0179-01 | 23 | -13 | -14 | 100 | 100 |
| IHuS#ABL-0193-01 | 167 | -7 | -11 | 100 | 100 |
| IHuS#ABL-0194-01 | 29 | -11 | -16 | 100 | 100 |
| IHuS#ABL-0195-01 | 285 | -8 | -14 | 100 | 100 |

Figure 8 (continued)

| Sample | REFERENCE B | REFERENCE B(L11V,V89L)-A | REFERENCE B(L11V,V89L,T110K)-A | REFERENCE B(L11V,V89L)-A | REFERENCE B(L11V,V89L,T110K)-A |
|---|---|---|---|---|---|
| IHuS#ABL-0196-01 | -6 | -2 | -12 | | |
| IHuS#ABL-0180-01 | 7 | -4 | -12 | | |
| IHuS#ABL-0197-01 | -9 | -15 | -14 | | |
| IHuS#ABL-0204-01 | -1 | -1 | -6 | | |
| IHuS#ABL-0206-01 | 196 | 12 | -12 | 94 | 100 |
| IHuS#ABL-0207-01 | 58 | -6 | -10 | 100 | 100 |
| IHuS#ABL-0012-03 | -3 | -8 | -11 | | |
| IHuS#ABL-0208-01 | 334 | 8 | -11 | 98 | 100 |
| IHuS#ABL-0220-01 | 26 | -14 | -12 | 100 | 100 |
| IHuS#ABL-0214-01 | -4 | -10 | -14 | | |
| IHuS#ABL-0215-01 | -12 | -14 | -21 | | |
| IHuS#ABL-0181-01 | -9 | -11 | -16 | | |
| IHuS#ABL-0216-01 | 0 | -11 | -14 | | |
| IHuS#ABL-0217-01 | 51 | -9 | -12 | 100 | 100 |
| IHuS#ABL-0140-01 | 40 | -13 | -9 | 100 | 100 |
| IHuS#ABL-0224-01 | -18 | -20 | -26 | | |
| IHuS#ABL-0182-01 | -11 | -84 | -42 | | |
| IHuS#ABL-0226-01 | 44 | 49 | 53 | -13 | -22 |
| IHuS#ABL-0227-01 | 51 | 18 | 60 | 65 | -19 |
| IHuS#ABL-0205-01 | 12 | -3 | 12 | | |
| IHuS#ABL-0060-03 | 43 | -15 | -27 | 100 | 100 |

Figure 9
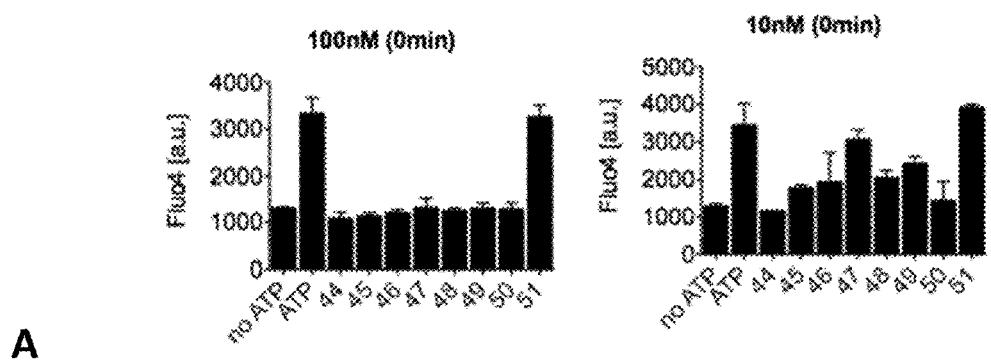
A
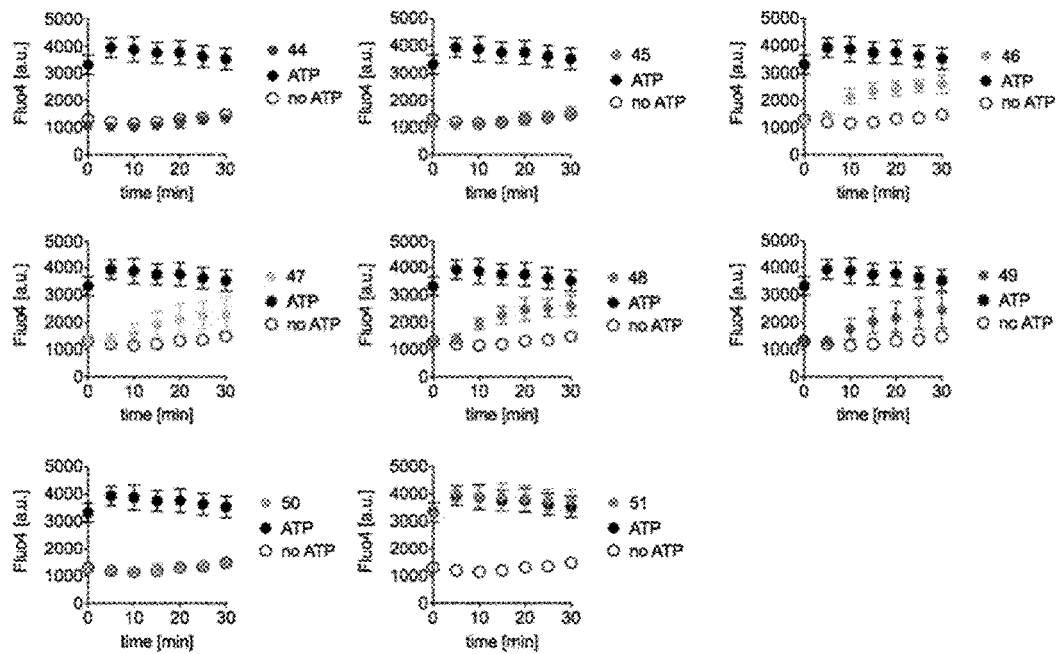
B

Figure 11
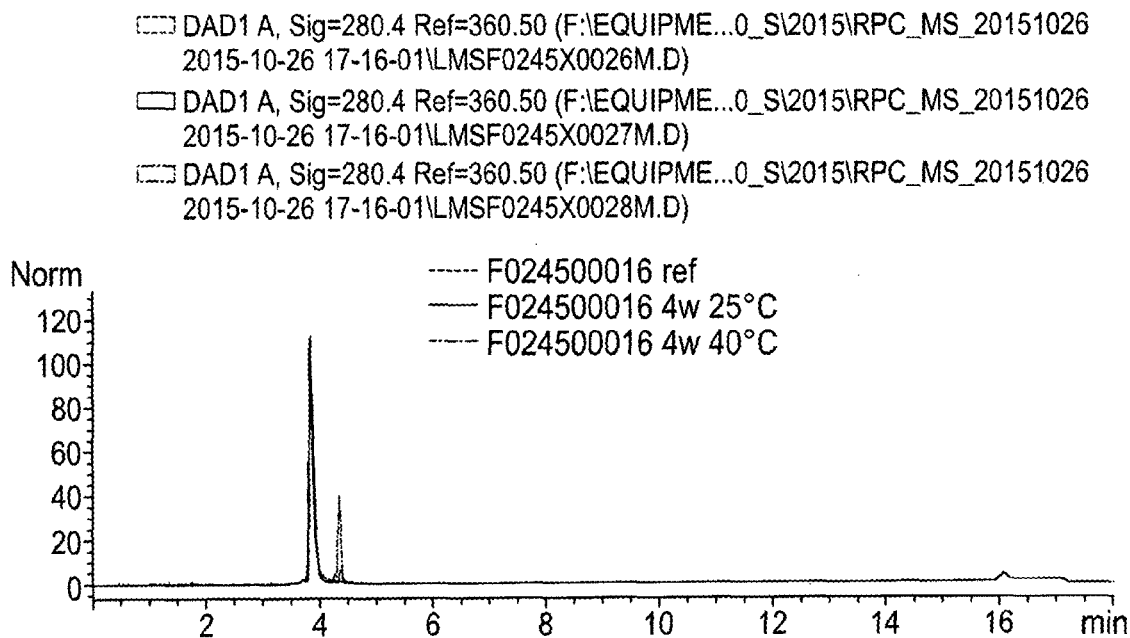
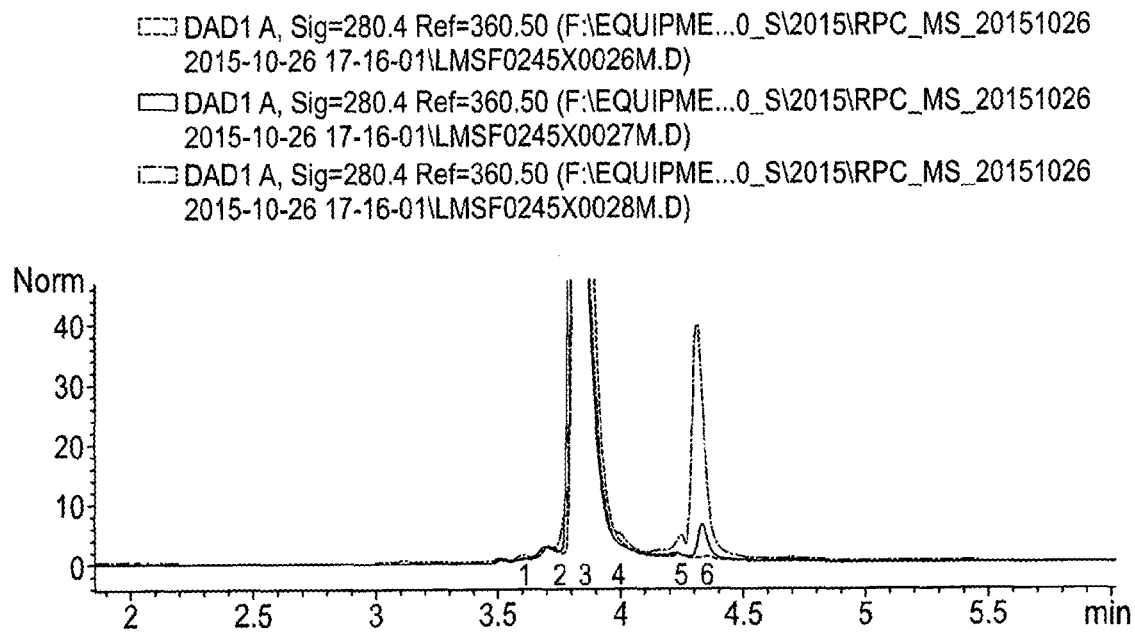

P2X7 RECEPTOR BINDERS AND POLYPEPTIDES COMPRISING THE SAME

RELATED APPLICATIONS

This application is a national stage filing under 35 U.S.C. § 371 of International Patent Application Serial No. PCT/EP2016/077452, filed Nov. 11, 2016, which claims the benefit under 35 U.S.C. § 119(e) of U.S. Provisional Application Ser. No. 62/254,298, filed Nov. 12, 2015, the contents of each of which is incorporated herein by reference in its entirety.

The present invention relates to amino acid sequences and polypeptides binding to the P2X7 receptor.

In particular, the present invention relates to improved heavy-chain immunoglobulin single variable domains (also referred to herein as "ISV's" or "ISVD's") binding to the P2X7 receptor, as well as to proteins, polypeptides and other constructs, compounds, molecules or chemical entities that comprise such ISVD's.

The anti-P2X7 receptor ISVDs provided by the invention are also referred to herein as the "P2X7 binders of the invention" or the "P2X7 binders". The anti-P2X7 receptor polypeptides, constructs, compounds, molecules or chemical entities described herein are also referred to herein as the "polypeptides of the invention" or "compounds of the invention".

As will become clear from the further description below, the invention provides two different groups of P2X7 binders, generally referred to herein as the "3c23-based P2X7 binders", "3c23-based binders" or "3c23-based building blocks" and the "1c81-based P2X7 binders", "1c81-based binders" or "1c81-based building blocks", respectively. In this respect, the invention not only provides these P2X7 binders and compounds and polypeptides comprising the same, but also biparatopic (as defined herein) polypeptides that comprise at least one (such as one or two) such 3c23-based binders and at least one (such as one or two) such 1c81-based binders.

The polypeptides and compounds provided by the invention are preferably fusion proteins. Also, as further described herein, the polypeptides of the invention may also have been provided with an extended half-life (as defined herein) and for this purpose may for example also comprise at least one ISVD binding to a serum protein such as human serum albumin. The polypeptides of the invention preferably also comprise a C-terminal extension X(n) (as further described herein).

Other aspects, embodiments, features, uses and advantages of the invention will be clear to the skilled person based on the disclosure herein.

Purine nucleotides are well established as extracellular signaling molecules. P2X receptors are ATP-gated cation channels that mediate fast excitatory transmission, e.g., in diverse regions of the brain and spinal cord. The P2X7 subtype has the unusual property of changing its ion selectivity during prolonged exposure to ATP, which results in progressive dilation of the channel pore and the development of permeability to molecules as large as 900 Da. The P2X7 receptor was originally described in cells of hematopoietic origin, including macrophages, microglia, and certain lymphocytes, and mediates the influx of Ca2+ and Na+ ions, as well as the release of proinflammatory cytokines. P2X7 receptors may affect neuronal cell death through their ability to regulate the processing and release of interleukin-1β, a key mediator in neurodegeneration, chronic inflammation, and chronic pain. Activation of P2X7 receptors provides an inflammatory stimulus, and P2X7 receptor-deficient mice have substantially attenuated inflammatory responses, including models of neuropathic and chronic inflammatory pain. Moreover, P2X7 receptor activity, by regulating the release of proinflammatory cytokines, may be involved in the pathophysiology of depression. The P2X7 receptor may thus represent a critical communication link between the nervous and immune systems (Skaper et al. 2010 FASEB J. 24:337-345). The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders, while providing a target for therapeutic exploitation.

In cancer where apoptotic cell death is an important mechanism of disease, P2X7 with its direct effect in apoptosis plays a significant role as it was shown in skin cancers and uterine epithelial cancers compared to normal tissues. Early apoptotic cell death to the retina in diabetes in rodent models has been linked to P2X7 activation in that part of the eye, suggesting a possible connection to diabetic microvascular injury. It has been reported that P2X7 receptor polymorphisms may be linked to hypertension in a family based quantitative genetic association study, with a strong association of single nucleotide polymorphism rs591874 in the first intron of P2X7 and nocturnal diastolic blood pressure. P2X7 receptors are expressed in cells of the cardiovascular system and drugs affecting this signaling system may provide new therapies in hypertension and prevention of thrombotic events. Expression of P2X7 receptors in healthy kidney is very little if any. In contrast, expression of P2X7 is increased in diseased renal tissue and immunohistochemistry of the glomeruli of two rodent models of kidney disease has shown that the predominant expression is in podocytes, endothelial and mesangial cells. A potential role for P2X7 receptors has been described for polycystic kidney disease and renal fibrosis.

Since ATP plays key roles in neurotransmission and neuromodulation, purine receptor subfamilies, including P2X7, have been involved in various pathological conditions. This pathophysiology of central nervous system (CNS) disorders includes brain trauma, ischemia, neurodegenerative and neuropsychiatric diseases. When injury happens, large amounts of ATP are released in the extracellular environment, which are important for triggering cellular responses to trauma. In this situation, expression levels of P2X4 and P2X7 changes which might stimulate the migration and chemotaxis of resting microglia to the site of damage. P2X7 plays an important role in controlling microglia proliferation and death. Cerebral ischemia can produce and exacerbate problems to the CNS which include stroke and it is possible that the P2X7 receptor (P2X7R) which is expressed on microglia, is involved in cortical damage as a consequence of glucose/oxygen deprivation. Neuroinflammation plays a major role in the pathogenesis of a number of neurodegenerative diseases such as Alzheimer's disease and Parkinson's disease. Although the precise mechanism is obscure, dysregulation of the signaling transduction pathway in microglia may enhance inflammation, leading to synaptic dysfunction and ultimately to neuronal cell death. The expression and function of the P2X7 receptor is significantly up-regulated in the post-mortem brain of Alzheimer's disease patients and various neurodegenerative disease animal models. This supports the role of the P2X7R pathway in the progression of neurodegeneration. Blocking P2X7R has been shown to result in the amelioration of neuropathology in various animal models.

Taken together, these results indicate that the P2X7R signaling pathway constitutes a therapeutic target for treating various neurodegenerative diseases including Alzheimer's disease and Huntington's disease.

ISVD's (and in particular Nanobodies) that can bind to the P2X7 receptor and their uses are known in the art, in particular from WO 2010/070145 and WO 2013/178783.

WO 2013/178783 discloses as SEQ ID NO: 12 an anti-P2X7 receptor Nanobody referred to as 3c23 (see SEQ ID NO:87 herein). In this application, a reference Nanobody (referred to herein as "Reference A") is used that has the same sequence as 3c23, but with humanizing A14P and Q108L substitutions compared to 3c23. The amino acid sequence of 3c23 and the amino acid sequence of Reference A (together with its CDR's according to the Kabat and Abm conventions; note that SEQ ID NOs: 4 and 7 are identical), is given in Table A below as SEQ ID NO: 1 and SEQ ID NOs: 2 to 7.

WO 2013/178783 also discloses as SEQ ID NO: 6 an anti-P2X7 receptor Nanobody referred to as 1c81 (see SEQ ID NO:88 herein). In this application, a reference Nanobody (referred to herein as "Reference B") is used that has the same sequence as 1c81, but with humanizing A14P and Q108L substitutions compared to 1c81. The amino acid sequence of 1c81 and Reference B (together with its CDR's according to the Kabat and Abm conventions; note that SEQ ID NOs: 11 and 14 are identical), is given in Table B below as SEQ ID NO: 8 and SEQ ID NOs: 9 to 14.

TABLE A

3c23, Reference A and its CDR's.

| SEQ ID NO | Description | Sequence |
|---|---|---|
| 1 | reference A: 7P2X3c23 (A14P, Q108L) | EVQLVESGGGLVQPGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTLVTVSS |
| 2 | CDR1 (Kabat) | HYAMG |
| 3 | CDR2 (Kabat) | AISSYGSTDYGDSVKG |
| 4 | CDR3 (Kabat/Abm) | ADETLGAVPNFRLHEKYEYEY |
| 5 | CDR1 (Abm) | GRTFRHYAMG |
| 6 | CDR2 (Abm) | AISSYGSTD |
| 7 | CDR3 (Kabat/Abm) | ADETLGAVPNFRLHEKYEYEY |
| 87 | WO 2013/178783; SEQ ID NO: 12 (7P2X3c23) | EVQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTQVTVSS |

TABLE B

1c81, Reference B and its CDR's.

| SEQ ID NO | Description | Sequence |
|---|---|---|
| 8 | reference B: 7P2X1c81 (A14P, Q108L) | EVQLVESGGKLVQPGGSLRLSCSASGRTFSFSTSTMGWFRQAPGKELEFVAAIDWSDFNTYYADSVKGRFTISRHNPRNSVYLQLNSLKPEDTAVYYCAAHSETRGGTRYFDRPSLYNYWGQGTLVTVSS |
| 9 | CDR1 (Kabat) | FSTSTMG |
| 10 | CDR2 (Kabat) | AIDWSDFNTYYADSVKG |
| 11 | CDR3 (Kabat/Abm) | HSETRGGTRYFDRPSLYNY |
| 12 | CDR1 (Abm) | GRTFSFSTSTMG |
| 13 | CDR2 (Abm) | AIDWSDFNTY |
| 14 | CDR3 (Kabat/Abm) | HSETRGGTRYFDRPSLYNY |

TABLE B-continued

1c81, Reference B and its CDR's.

| SEQ ID NO | Description | Sequence |
|---|---|---|
| 88 | WO 2013/178783; SEQ ID NO: 6 (7P2X1c81) | EVQLVESGGKLVQAGGSLRLSCSASGRTFSFSTSTMGWFRQ APGKELEFVAAIDWSDFNTYYADSVKGRFTISRHNPRNSVYL QLNSLKPEDTAVYYCAAHSETRGGTRYFDRPSLYNYWGQG TQVTVSS |

The present invention aims to provide improved P2X7 receptor binders, in particular improved anti-P2X7 receptor ISVD's and more in particular improved anti-P2X7 receptor Nanobodies.

The invention also aims to provide polypeptides, proteins and other compounds and constructs that comprise at least one such anti-P2X7 receptor ISVD. Such polypeptides, proteins and other compounds and constructs are preferably as further described herein.

More in particular, the invention aims to provide improved P2X7 receptor binders that are variants of 3c23 and Reference A and that have reduced binding by interfering factors (generally referred to as "pre-existing antibodies") that may be present in the sera from some healthy human subjects as well as from patients. Reference is made to WO 12/175741, WO 2013/024059 and also for example by Holland et al. (J. Clin. Immunol. 2013, 33(7):1192-203) as well as to the co-pending non-prepublished PCT application PCT/EP2015/060643 by Assignee filed on May 13, 2015 and entitled "Improved immunoglobulin variable domains".

The invention also aims to provide polypeptides, proteins and other compounds and constructs that comprise at least one such 3c23-based binder. Such polypeptides, proteins and other compounds and constructs are preferably as further described herein.

The invention also aims to provide improved P2X7 receptor binders that are variants of 1c81 and Reference B and that have reduced binding by pre-existing antibodies. The invention further aims to provide polypeptides, proteins and other compounds and constructs that comprise at least one such 1c81-based binder. Such polypeptides, proteins and other compounds and constructs are preferably as further described herein.

As mentioned, in one preferred aspect, the invention provides biparatopic anti-P2X7 receptor polypeptides that comprise these 3c23 and/or 1c81-based building blocks of the invention.

Some preferred, but non-limiting 3c23-based building blocks of the invention are listed in FIG. 2 as SEQ ID NOs: 15 to 42, and FIG. 3A gives an alignment of Reference A, 3c23 and the sequences of SEQ ID NOs: 15 to 42.

Some preferred, but non-limiting 1c81-based building blocks of the invention are listed in FIG. 2 as SEQ ID NOs: 43 to 70, and FIG. 3B gives an alignment of Reference B, 1c81 and the sequences of SEQ ID NOs: 43 to 70.

Of the P2X7 binders shown in FIGS. 3 and 4, the sequences of SEQ ID NOs: 29 to 42 and 57 to 70 are examples of P2X7 receptor binders of the invention having a C-terminal alanine extension, i.e. an alanine residue at the C-terminal end of the ISVD-sequence (also sometimes referred to as "position 114") compared to the usual C-terminal sequence VTVSS (SEQ ID NO: 84, as present in Reference A). As described in WO 12/175741 (but also for example in WO 2013/024059 and PCT/EP2015/060643), this C-terminal alanine extension can prevent the binding of so-called "pre-existing antibodies" (assumed to be IgG's) to a putative epitope that is situated at the C-terminal region of the ISV. This epitope is assumed to include, among other residues, the surface-exposed amino acid residues of the C-terminal sequence VTVSS as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in a lot of cases even essentially fully prevent) the binding of the "pre-existing antibodies" that can be found in the sera from a range of subjects (both healthy subjects as patients), it has been found that the sera from some subjects (such as the sera from patients with some immune diseases such as SLE) can contain pre-existing antibodies that can bind to the C-terminal region of an ISV (when such region is exposed) even when the ISV contains such a C-terminal alanine (or more generally, such C-terminal extension). Reference is again made to the co-pending non-prepublished PCT application PCT/EP2015/060643 by Assignee filed on May 13, 2015 and entitled "Improved immunoglobulin variable domains".

Accordingly, one specific objective of the invention is to provide P2X7 receptor binders (and in particular P2X7 receptor binders that are improved variants of either Reference A or Reference B) and that have reduced binding by so-called "pre-existing antibodies", and in particular of the kind described in PCT/EP2015/060643 (i.e. those pre-existing antibodies that can bind to an exposed C-terminal region of an ISV even in the presence of a C-terminal extension). As mentioned, the P2X7 binders provided by the invention can also be suitably used as building blocks to provide polypeptides of the invention that also have low or reduced binding by pre-existing antibodies. Again, such polypeptides are preferably as further described herein.

Generally, the P2X7 binders provided by the invention will comprise (a suitable combination of) mutations at positions 11, 89, 110 and/or 112 that are as further described herein.

Table C lists some preferred but non-limiting possible combinations of the amino acid residues that can be present at positions 11, 89, 110 and 112 of the P2X7 binders of the invention. Combinations that are particularly preferred are indicated in bold, and the most preferred combinations are indicated in bold/underline.

TABLE C

Possible combinations of amino acids at positions 11, 89, 110 and 112.

| COMBI-NATION | POSITION 11 | 89 | 110 | 112 | COMBI-NATION | POSITION 11 | 89 | 110 | 112 |
|---|---|---|---|---|---|---|---|---|---|
| | L | T | T | S | | V | T | T | S |
| | L | T | T | K | | V | T | T | K |
| | L | T | T | Q | | V | T | T | Q |
| | L | T | K | S | | V | T | K | S |
| | L | T | Q | S | | V | T | Q | S |
| | L | V | T | K | | V | V | T | K |
| | L | V | T | Q | | V | V | T | Q |
| | L | V | K | S | | V | V | K | S |
| | L | V | Q | S | | V | V | Q | S |
| | | | | | | V | L | T | S |
| | L | L | T | K | | V | L | T | K |
| | L | L | T | Q | | V | L | T | Q |
| | L | L | K | S | | V | L | K | S |
| | L | L | Q | S | | V | L | Q | S |

When the P2X7 binders of the invention are used in monovalent format, or when they are present at the N-terminal end of a polypeptide of the invention, the P2X7 binders (and thereby, the resulting polypeptide of the invention) preferably have an aspartic acid residue (D) at position 1 (e.g. have an E1D mutation compared to the sequences of SEQ ID NOs 15 to 42 or 43 to 70, respectively).

Also, when the P2X7 binders of the invention are used in monovalent format, or when they are present at the C-terminal end of a polypeptide of the invention, the P2X7 binders (and thereby, the resulting polypeptide of the invention) preferably have a C-terminal extension X(n). Such a C-terminal extension may be as further described herein and in WO 2012/175741 and PCT/EP2015/06043), and preferably is of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as follows:
(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a polypeptide of the invention does not contain a (free) cysteine residue (unless said cysteine residue is used or intended for further functionalization, for example for pegylation).

Some specific, but non-limiting examples of useful C-terminal extensions are the following amino acid sequences: A, AA, AAA, G, GG, GGG, AG, GA, AAG, AGG, AGA, GGA, GAA or GAG.

The present invention also provides a number of sequence optimized immunoglobulin single variable domains, including sequence optimized 3c23 and 1c81 variants.

In particular, sequence optimized immunoglobulin single variable domains may be amino acid sequences that are as generally defined for immunoglobulin single variable domains herein, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domains may be partially humanized or fully humanized. Also, as mentioned, the polypeptides provided by the invention preferably have an extended half-life (as defined herein). Preferably, for this purpose, the polypeptides of the invention also comprise at least one (such as one) ISVD binding to a serum protein such as human serum albumin. Preferred examples of serum albumin binding ISVDs that can be included in the polypeptides of the invention for this purpose will be clear to the skilled person based on the disclosure herein.

The invention also relates to proteins, polypeptides and other constructs, molecules or chemical entities that comprise or essentially consist of the P2X7 receptor binders of the invention (i.e. one or more such as one or two 3c23-based building blocks and/or one or more such as one or two 1c81-based building blocks) as described herein; to methods for expressing/producing the P2X7 receptor binders of the invention and/or for expressing/producing proteins, polypeptides and other constructs, molecules or chemical entities comprising the same; to compositions and products (such as pharmaceutical compositions and products) that comprise the P2X7 receptor binders of the invention and/or proteins, polypeptides and other constructs, molecules or chemical entities comprising the same; to nucleotide sequence and nucleic acids that encode the P2X7 receptor binders of the invention and/or that encode proteins or polypeptides comprising the same; and to uses (and in particular therapeutic, prophylactic and diagnostic uses) of the P2X7 receptor binders of the invention and of proteins, polypeptides and other constructs, molecules or chemical entities comprising the same.

These and other aspects, embodiments, advantages, applications and uses of the invention will become clear from the further description herein.

In the present specification, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regard to the CDR's, as is well-known in the art, there are multiple conventions to define and describe the CDR's of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims, even though the CDR's according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website http://www.bioinf.org.uk/abs/).

Also, in the present specification:

the term "immunoglobulin single variable domain" (also referred to as "ISV" or ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VH's), IgNAR, domains, (single domain) antibodies (such as dAb's™) that are VH domains or that are derived from a VH domain and (single domain) antibodies (such as dAb's™) that are VL domains or that are derived from a VL domain. Unless explicitly mentioned otherwise herein, ISVDs that are, are based on and/or derived from heavy chain variable domains (such as VH or VHH domains) are generally be preferred. Most preferably, unless explicitly indicated otherwise herein, an ISVD will be a Nanobody.

the term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

Generally, unless indicated otherwise herein, the ISVD's, Nanobodies, polypeptides, proteins and other compounds and constructs referred to herein will be intended for use in prophylaxis or treatment of diseases or disorders in man (and/or optionally also in warm-blooded animals and in particular mammals). Thus, generally, the ISVD's, Nanobodies, polypeptides, proteins and other compounds and constructs described herein are preferably such that they can be used as, and/or can suitably be a part of, a (biological) drug or other pharmaceutically or therapeutically active compound and/or of a pharmaceutical product or composition. Such a drug, compound or product is preferably such that it is suitable for administration to a human being, e.g. for prophylaxis or treatment of a subject in need of such prophylaxis or treatment or for example as part of a clinical trial. As further described herein, for this purpose, such a drug or compound may contain other moieties, entities or binding units besides the ISVDs provided by the invention (which as also described herein may for example be one or more other further therapeutic moieties and/or one or more other moieties that influence the pharmacokinetic or pharmacodynamic properties of the ISVD-based or Nanobody-based biological such as its half-life). Suitable examples of such further therapeutic or other moieties will be clear to the skilled person, and for example generally can include any therapeutically active protein, polypeptide or other binding domain or binding unit. Also, as further described herein, an ISVD or Nanobody as described herein may be directed against a (human) serum protein such as (human) serum albumin, and such an ISVD or Nanobody may also find therapeutic uses, in particular in and/or for extending the half-life of therapeutic moieties and compounds (such as in or for the ISV-based biologicals described herein). Reference is for example made to WO 2004/041865, WO 2006/122787 and WO 2012/175400, which generally describe the use of serum-albumin binding Nanobodies for half-life extension. Also, in the present specification, unless explicitly mentioned otherwise herein, all terms mentioned herein have the meaning given in WO 2009/138519 (or in the prior art cited in WO 2009/138519) or WO 2008/020079 (or in the prior art cited in WO 2008/020079). Also, where a method or technique is not specifically described herein, it can be performed as described in WO 2009/138519 (or in the prior art cited in WO 2009/138519) or WO 2008/020079 (or in the prior art cited in WO 2008/020079). Also, as described herein, any pharmaceutical product or composition comprising any ISVD or compound of the invention may also comprise one or more further components known per se for use in pharmaceutical products or compositions (i.e. depending on the intended pharmaceutical form) and/or for example one or more other compounds or active principles intended for therapeutic use (i.e. to provide a combination product).

Also, when used in the present specification or claims, the following terms have the same meaning as given on, and/or where applicable can be determined in the manner described in, pages 62-75 of WO 2009/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 2010/130832 of Ablynx N.V. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 2009/138519, WO 2010/130832 or WO 2008/020079.

The term "half-life" as used herein relates to an ISVD, Nanobody, ISVD-based biological, Nanobody-based biological or any other amino acid sequence, compound or polypeptide referred to herein can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t½-alpha, t½-beta and the area under the curve (AUC). In this respect it should be noted that the term "half-life" as used herein in particular refers to the t½-beta or terminal half-life (in which the t½-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t½-beta, either with or without an increase in the t½-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, N.Y. (2005), as well as to the general background art cited herein.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

Description of the 3c23-Based Binders of the Invention.

Generally, the 3c23-based binders provided by the invention are variants of SEQ ID NO:1 (Reference A) and 3c23 (SEQ ID NO: 87) that comprise the following amino acid residues (i.e. mutations compared to the sequence of SEQ ID NO:1 or 87):

89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, in the 3c23-based binders provided by the invention:
the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q; such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

3c23-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 3c23-based binders in which position 11 is V and position 89 is L, optionally with a 110K or 110Q mutation.

As further described herein, the P2X7 receptor binders of the invention that are 3c23-based building blocks of the invention preferably have the same combination of CDR's (i.e. CDR1, CDR2 and CDR3) as are present in 3c23 and in Reference A.

Accordingly, the 3c23-based binders provided by the invention preferably comprise the following CDRs (according to the Kabat convention):
a CDR1 (according to Kabat) that is the amino acid sequence HYAMG (SEQ ID NO:2); and
a CDR2 (according to Kabat) that is the amino acid sequence AISSYGSTDYGDSVKG (SEQ ID NO:3); and
a CDR3 (according to Kabat) that is the amino acid sequence ADETLGAVPNFRLHEKYEYEY (SEQ ID NO:4).

Alternatively, when the CDR's are given according to the Abm convention, the 3c23-based binders provided by the invention preferably comprise the following CDRs:
a CDR1 (according to Abm) that is the amino acid sequence GRTFRHYAMG (SEQ ID NO:5); and
a CDR2 (according to Abm) that is the amino acid sequence AISSYGSTD (SEQ ID NO:6); and
a CDR3 (according to Abm) that is the amino acid sequence ADETLGAVPNFRLHEKYEYEY (SEQ ID NO:7, which is the same as SEQ ID NO:4).

A 3c23-based binder preferably also has:
a degree of sequence identity with the reference amino acid sequence of SEQ ID NO:1 (in which any C-terminal extension that may be present as well as the CDRs are not taken into account for determining the degree of sequence identity) of at least 85%, preferably at least 90%, more preferably at least 95%; and/or
no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the reference amino acid sequence of SEQ ID NO:1 (in which said amino acid differences, if present, may be present in the frameworks and/or the CDR's but are preferably present only in the frameworks and not in the CDRs).

With regard to the various aspects and preferred aspects of the 3c23-based binders provided by the invention, when it comes to the degree of sequence identity with respect to SEQ ID NO:1 and/or the number and kind of "amino acid differences" that may be present in such a binder of the invention (i.e. compared to the sequence of SEQ ID NO:1), it should be noted that, when it is said that (i) a 3c23-based binder has a degree of sequence identity with the sequence of SEQ ID NO:1 of at least 85%, preferably at least 90%, more preferably at least 95% (in which the CDRs, any C-terminal extension that may be present, as well as the mutations at positions 11, 89, 110 and/or 112 required by the specific aspect involved, are not taken into account for determining the degree of sequence identity); and/or when it is said that (ii) a 3c23-based binder has no more than 7, preferably no more than 5, such as only 3, 2 or 1 "amino acid differences" with the sequence of SEQ ID NO:1 (again, not taking into account any C-terminal extension that may be present and not taking into account the mutations at positions 11, 89, 110 and/or 112 required by the specific aspect involved), then this also includes sequences that have no amino acid differences with the sequence of SEQ ID NO:1 other than the mutations at positions 11, 89, 110 and/or 112 required by the specific aspect involved) and any C-terminal extension that may be present.

Thus, in one specific aspect of the invention, the 3c23-based binders provided by the invention may have 100% sequence identity with SEQ ID NO:1 (including the CDRs, but not taking into account the mutation(s) or combination of mutations at positions 11, 89, 110 and/or 112 disclosed herein and/or any C-terminal extension that may be present) and/or may have no amino acid differences with SEQ ID NO:1 (i.e. other than the mutation(s) or combination of mutations at positions 11, 89, 110 and/or 112 disclosed herein and any C-terminal extension that may be present).

When any amino acid differences are present (i.e. besides any C-terminal extension and the mutations at positions 11, 89, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the 3c23-based binders provided by the invention have the same CDRs (defined according to the Abm convention) as are present in SEQ ID NO:1.

Also, when a 3c23-based binder has one or more amino acid differences with the sequence of SEQ ID NO:1 (besides the mutations at positions 11, 89, 110 and/or 112 that are required by the specific aspect involved), then some specific, but non-limiting examples of such mutations/amino acid differences that may be present (i.e. compared to the sequences of SEQ ID NO:1) are for example A14P, G60A, D73N, A74S, P79Y and/or K83R, or any suitable combination of two or more (and up to and including all) of these mutations, such as for instance depicted by the particularly preferred SEQ ID NO:s 136 to 143, 154 to 161 and 169 to 176. Other examples of mutations are (a suitable combination of) one or more suitable "humanizing" substitutions; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions).

Also, when a 3c23-based binder is in monovalent format or present at and/or forms the N-terminal part of the polypeptide of the invention, then it preferably contains a D at position 1 (i.e. an E1D mutation compared to Reference A). Accordingly, in a further aspect, the invention relates to a polypeptide of the invention (which is as further described herein) that has a 3c23-based binder (which is as further described herein) at its N-terminal end, wherein said 3c23-based binder has a D at position 1 such as e.g. SEQ ID NO:s 154 to 161 and 169 to 176.

Furthermore, when a 3c23-based binder is in monovalent format or is present at and/or forms the C-terminal end of a polypeptide of the invention, it preferably has a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I) such as e.g. SEQ ID NO:s 169 to 176.

According to some preferred, but non-limiting examples of such C-terminal extensions $X_{(n)}$, X and n can be as further described herein for the polypeptides of the invention.

When the 3c23-based binders provided by the invention contain mutations at positions 110 or 112 (optionally in combination with mutations at position 11 and/or 89 as described herein), the C-terminal amino acid residues of framework 4 (starting from position 109) can be as follows: (i) if no C-terminal extension is present: VTVKS (SEQ ID NO:72), VTVQS (SEQ ID NO:73), VKVSS (SEQ ID NO:74) or VQVSS (SEQ ID NO:75); or (ii) if a C-terminal extension is present: VTVKSX$_{(n)}$ (SEQ ID NO:76), VTVQSX(n) (SEQ ID NO:77), VKVSSX(n) (SEQ ID NO:78) or VQVSSX$_{(n)}$ (SEQ ID NO:79), such as VTVKSA (SEQ ID NO:80), VTVQSA (SEQ ID NO:81), VKVSSA (SEQ ID NO:82) or VQVSSA (SEQ ID NO:83). When the 3c23-based binders provided by the invention do not contain mutations at positions 110 or 112 (but only mutations at position 11 and/or 89 as described herein), the C-terminal amino acid residues of framework 4 (starting from position 109) will usually be either: (i) when no C-terminal extension is present: VTVSS (SEQ ID NO:84) (as in the sequence of SEQ ID NO:1); or (ii) when a C-terminal extension is present: VTVSSX$_{(n)}$ (SEQ ID NO:85) such as VTVSSA (SEQ ID NO:86). In these C-terminal sequences, X and n are as defined herein for the C-terminal extensions.

Thus, in a first aspect, a 3c23-based binder has:
 a CDR1 (according to Kabat) that is the amino acid sequence HYAMG (SEQ ID NO:2); and
 a CDR2 (according to Kabat) that is the amino acid sequence AISSYGSTDYGDSVKG (SEQ ID NO:3); and
 a CDR3 (according to Kabat) that is the amino acid sequence ADETLGAVPNFRLHEKYEYEY (SEQ ID NO:4);
and has:
 a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:
no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1), in which:
the amino acid residue at position 11 of the 3c23-based binder is preferably chosen from L or V; and
the amino acid residue at position 89 of the 3c23-based binder is preferably suitably chosen from T, V or L; and
the amino acid residue at position 110 of the 3c23-based binder is preferably suitably chosen from T, K or Q; and
the amino acid residue at position 112 of the 3c23-based binder is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, a 3c23-based binder has:
a CDR1 (according to Kabat) that is the amino acid sequence HYAMG (SEQ ID NO:2); and
a CDR2 (according to Kabat) that is the amino acid sequence AISSYGSTDYGDSVKG (SEQ ID NO:3); and
a CDR3 (according to Kabat) that is the amino acid sequence ADETLGAVPNFRLHEKYEYEY (SEQ ID NO:4);

and has:
a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:
no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1),
such that said 3c23-based binder comprises the following amino acid residues (i.e. mutations compared to the amino acid sequence of SEQ ID NO:1) at the positions mentioned (numbering according to Kabat):
89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

As mentioned, when a 3c23-based binder is present at the C-terminal end of a polypeptide the invention (as defined herein), the 3c23-based binder (and consequently, the resulting polypeptide of the invention) preferably has a C-terminal extension X(n) as described herein for the polypeptides of the invention and/or as described in WO 2012/175741 or PCT/EP2015/060643.

As mentioned, in the invention, 3c23-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 3c23-based binders in which position 11 is V and position 89 is L, optionally with a 110K or 110Q mutation.

Thus, in one preferred aspect, a 3c23-based binder has:
a CDR1 (according to Kabat) that is the amino acid sequence HYAMG (SEQ ID NO:2); and
a CDR2 (according to Kabat) that is the amino acid sequence AISSYGSTDYGDSVKG (SEQ ID NO:3); and
a CDR3 (according to Kabat) that is the amino acid sequence ADETLGAVPNFRLHEKYEYEY (SEQ ID NO:4);

and has:
a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:
no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1), in which:

the amino acid residue at position 11 of the 3c23-based binder is preferably chosen from L or V; and the amino acid residue at position 89 of the 3c23-based binder is T; and the amino acid residue at position 110 of the 3c23-based binder is preferably suitably chosen from T, K or Q (and is preferably T); and the amino acid residue at position 112 of the 3c23-based binder is preferably suitably chosen from S, K or Q (and in preferably S).

In another preferred aspect, a 3c23-based binder has:

a CDR1 (according to Kabat) that is the amino acid sequence HYAMG (SEQ ID NO:2); and a CDR2 (according to Kabat) that is the amino acid sequence AISSYGSTDYGDSVKG (SEQ ID NO:3); and a CDR3 (according to Kabat) that is the amino acid sequence ADETLGAVPNFRLHEKYEYEY (SEQ ID NO:4);

and has:

a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:

no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1), in which:

the amino acid residue at position 11 of the 3c23-based binder is V; and the amino acid residue at position 89 of the 3c23-based binder is L; and the amino acid residue at position 110 of the 3c23-based binder is preferably suitably chosen from T, K or Q; and the amino acid residue at position 112 of the 3c23-based binder is preferably suitably chosen from S, K or Q.

In one specific, but non-limiting aspect, the 3c23-based binders provided by the invention comprise the following amino acid residues (i.e. mutations compared to the sequence of SEQ ID NO:1) at the positions mentioned (numbering according to Kabat):

11V in combination with 89L; or
11V in combination with 110K or 110Q;
11V in combination with 112K or 112Q;
11V in combination with 89L and 110K or 110Q; or
11V in combination with 89L and 112K or 112Q;

and have CDR's (according to Kabat) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):

89L in combination with 11V; or
89L in combination with 110K or 110Q; or
89L in combination with 112K or 112Q; or
89L in combination with 11V and 110K or 110Q; or
89L in combination with 11V and 112K or 112Q;

and have CDR's (according to Kabat) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):

110K or 110Q in combination with 11V; or
110K or 110Q in combination with 89L; or
110K or 110Q in combination with 11V and 89L;

and have CDR's (according to Kabat) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):

112K or 112Q in combination with 11V; or
112K or 112Q in combination with 89L; or
112K or 112Q in combination with 11V and 89L;

and have CDR's (according to Kabat) and have an overall degree of sequence identity with the amino acid sequence of SEQ ID NO:1 that are as described herein.

In another aspect, the 3c23-based binders provided by the invention comprise a T at position 89 and have CDR's (according to Kabat) and have an overall degree of sequence identity with the amino acid sequence of SEQ ID NO:1 that are as described herein.

In another aspect, the 3c23-based binders provided by the invention comprise a V at position 11 and an L at position 89 and have CDR's (according to Kabat) and have an overall degree of sequence identity with the amino acid sequence of SEQ ID NO:1 that are as described herein.

As mentioned, the 3c23-based binders provided by the invention according to the aspects described herein are preferably further such that they contain a suitable combination of an A14P mutation, an A74S mutation and/or a K83R mutation, and preferably a suitable combination of any two of these mutations, such as all three of these mutations (and again, when the 3c23-based binder is present at the N-terminal end of a polypeptide of the invention, preferably also an E1D mutation).

In another aspect, a 3c23-based binder has:
- a CDR1 (according to Abm) that is the amino acid sequence GRTFRHYAMG (SEQ ID NO:5); and
- a CDR2 (according to Abm) that is the amino acid sequence AISSYGSTD (SEQ ID NO:6); and
- a CDR3 (according to Abm) that is the amino acid sequence ADETLGAVPNFRLHEKYEYEY (SEQ ID NO:4);

and has:
- a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1),
in which:
- the amino acid residue at position 11 of the 3c23-based binder is preferably chosen from L or V; and
- the amino acid residue at position 89 of the 3c23-based binder is preferably suitably chosen from T, V or L; and
- the amino acid residue at position 110 of the 3c23-based binder is preferably suitably chosen from T, K or Q; and
- the amino acid residue at position 112 of the 3c23-based binder is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, a 3c23-based binder has:
- a CDR1 (according to Abm) that is the amino acid sequence GRTFRHYAMG (SEQ ID NO:5); and
- a CDR2 (according to Abm) that is the amino acid sequence AISSYGSTD (SEQ ID NO:6); and
- a CDR3 (according to Abm) that is the amino acid sequence ADETLGAVPNFRLHEKYEYEY (SEQ ID NO:4);

and has:
- a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or has:
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:1),
such that said 3c23-based binder comprises the following amino acid residues (i.e. mutations compared to the amino acid sequence of SEQ ID NO:1) at the positions mentioned (numbering according to Kabat):
  89T; or
  89L in combination with 11V; or
  89L in combination with 110K or 110Q; or
  89L in combination with 112K or 112Q; or
  89L in combination with 11V and 110K or 110Q; or
  89L in combination with 11V and 112K or 112Q; or
  11V in combination with 110K or 110Q; or
  11V in combination with 112K or 112Q.

As mentioned, when a 3c23-based binder is used in a monovalent format and/or is present at the C-terminal end of a polypeptide of the invention (as defined herein), the 3c23-based binder (and consequently, the resulting polypeptide of the invention) preferably has a C-terminal extension X(n), which C-terminal extension may be as described herein for the polypeptides of the invention and/or as described in WO 2012/175741 or PCT/EP2015/060643.

As mentioned, in the invention, 3c23-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 3c23-based binders in which position 11 is V and position 89 is L, optionally with a 110K or 110Q mutation.

Thus, in one preferred aspect, a 3c23-based binder has:
 a CDR1 (according to Abm) that is the amino acid sequence GRTFRHYAMG (SEQ ID NO:5); and
 a CDR2 (according to Abm) that is the amino acid sequence AISSYGSTD (SEQ ID NO:6); and
 a CDR3 (according to Abm) that is the amino acid sequence ADETLGAVPNFRLHEKYEYEY (SEQ ID NO:4);
and has:
 a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;
and/or has:
 no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
 a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and optionally (i.e. when in monovalent format or when present at the N-terminal end of a polypeptide of the invention) has a D at position 1 (i.e. an E1D mutation compared to SEQ ID NO:1),
in which
 the amino acid residue at position 11 of the 3c23-based binder is preferably chosen from L or V; and
 the amino acid residue at position 89 of the 3c23-based binder is T; and
 the amino acid residue at position 110 of the 3c23-based binder is preferably suitably chosen from T, K or Q (and is preferably T); and
 the amino acid residue at position 112 of the 3c23-based binder is preferably suitably chosen from S, K or Q (and in preferably S).

In another preferred aspect, a 3c23-based binder has:
 a CDR1 (according to Abm) that is the amino acid sequence GRTFRHYAMG (SEQ ID NO:5); and
 a CDR2 (according to Abm) that is the amino acid sequence AISSYGSTD (SEQ ID NO:6); and
 a CDR3 (according to Abm) that is the amino acid sequence ADETLGAVPNFRLHEKYEYEY (SEQ ID NO:4);
and has:
 a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;
and/or has:
 no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
 a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and optionally (i.e. when in monovalent format or when present at the N-terminal end of a polypeptide of the invention) has a D at position 1 (i.e. an E1D mutation compared to SEQ ID NO:1),
in which:
 the amino acid residue at position 11 of the 3c23-based binder is V; and
 the amino acid residue at position 89 of the 3c23-based binder is L; and
 the amino acid residue at position 110 of the 3c23-based binder is preferably suitably chosen from T, K or Q; and
 the amino acid residue at position 112 of the 3c23-based binder is preferably suitably chosen from S, K or Q.

In one specific, but non-limiting aspect, the 3c23-based binders provided by the invention comprise the following amino acid residues (i.e. mutations compared to the sequence of SEQ ID NO:1) at the positions mentioned (numbering according to Kabat):
 11V in combination with 89L; or
 11V in combination with 110K or 110Q;
 11V in combination with 112K or 112Q;
 11V in combination with 89L and 110K or 110Q; or
 11V in combination with 89L and 112K or 112Q;
and have CDR's (according to Abm) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):
 89L in combination with 11V; or
 89L in combination with 110K or 110Q; or
 89L in combination with 112K or 112Q; or 89L in combination with 11V and 110K or 110Q; or
89L in combination with 11V and 112K or 112Q;
and have CDR's (according to Abm) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):
110K or 110Q in combination with 11V; or
110K or 110Q in combination with 89L; or
110K or 110Q in combination with 11V and 89L;
and have CDR's (according to Abm) and have an overall degree of sequence identity with the amino acid sequence of SEQ ID NO:1 that are as described herein.

In another specific, but non-limiting aspect, the 3c23-based binders provided by the invention comprise the following amino acid residues (i.e. mutations compared to the sequence of SEQ ID NO:1) at the positions mentioned (numbering according to Kabat):
112K or 112Q in combination with 11V; or
112K or 112Q in combination with 89L; or
112K or 112Q in combination with 11V and 89L;
and have CDR's (according to Abm) and have an overall degree of sequence identity with the amino acid sequence of SEQ ID NO:1 that are as described herein.

In another aspect, the 3c23-based binders provided by the invention comprise a T at position 89 and have CDR's (according to Abm) and have an overall degree of sequence identity with the amino acid sequence of SEQ ID NO:1 that are as described herein.

In another aspect, the 3c23-based binders provided by the invention comprise a V at position 11 and an L at position 89 and have CDR's (according to Abm) and have an overall degree of sequence identity with the amino acid sequence of SEQ ID NO:1 that are as described herein.

Some preferred but non-limiting examples of 3c23-based binders that can be present in the polypeptides of the invention are given in SEQ ID NO's: 15 to 42, and polypeptides of the invention that suitably comprise one or more of these sequences form further aspects of the invention (in each case, preferably with a D at position 1 when at the N-terminal end of the polypeptide and with a C-terminal alanine when at the C-terminal end of the polypeptide). Some particularly preferred 3c23-based binders that can be present in the polypeptides of the invention are the sequences of SEQ ID NOs: 24, 25, 38 and 39 or variants thereof with a (suitable combination of) one or more mutations chosen from A14P, G60A, D73N, A74S, P79Y and/or K83R, or any suitable combination of two or more (and up to and including all) of these mutations, such as for instance depicted by the particularly preferred SEQ ID NO:s 136 to 143 (again, in each case, preferably with a D at position 1 when at the N-terminal end of the polypeptide such as e.g. SEQ ID NO:s 154 to 161 and with a C-terminal alanine when at the C-terminal end of the polypeptide such as e.g. SEQ ID NO:s 169 to 176).

Description of the 1c81-Based Binders of the Invention

Generally, the 1c81-based binders provided by the invention are variants of SEQ ID NO:8 (Reference B) and 1c81 (SEQ ID NO:88) that comprise the following amino acid residues (i.e. mutations compared to the sequence of SEQ ID NO:8):
89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, in the 1c81-based binders provided by the invention:
the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q;
such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

1c81-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 1c81-based binders in which position 11 is V and position 89 is L, optionally with a 110K or 110Q mutation.

As also further described herein, the P2X7 receptor binders of the invention that are 1c81-based building blocks of the invention preferably have the same combination of CDR's (i.e. CDR1, CDR2 and CDR3) as are present in 1c81 and in Reference B.

Accordingly, the 1c81-based binders provided by the invention preferably comprise the following CDRs (according to the Kabat convention):
a CDR1 (according to Kabat) that is the amino acid sequence FSTSTMG (SEQ ID NO:9); and
a CDR2 (according to Kabat) that is the amino acid sequence AIDWSDFNTYYADSVKG (SEQ ID NO:10); and
a CDR3 (according to Kabat) that is the amino acid sequence HSETRGGTRYFDRPSLYNY (SEQ ID NO:11).

Alternatively, when the CDR's are given according to the Abm convention, the 1c81-based binders provided by the invention preferably comprise the following CDRs:
a CDR1 (according to Abm) that is the amino acid sequence GRTFSFSTSTMG (SEQ ID NO:12); and
a CDR2 (according to Abm) that is the amino acid sequence AIDWSDFNTY (SEQ ID NO:13); and
a CDR3 (according to Abm) that is the amino acid sequence HSETRGGTRYFDRPSLYNY (SEQ ID NO:14, which is the same as SEQ ID NO:11).

The above preferred CDR's are the same as are present in 1c81 (SEQ ID NO:88) and Reference B (SEQ ID NO:8).

A 1c81-based binder that is present in the polypeptides of the invention preferably also has:
a degree of sequence identity with the amino acid sequence of SEQ ID NO:8 (in which any C-terminal extension that may be present, as well as the CDRs, are not taken into account for determining the degree of sequence identity) of at least 85%, preferably at least 90%, more preferably at least 95%; and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs).

With regard to the various aspects and preferred aspects of the 1c81-based binders provided by the invention, when it comes to the degree of sequence identity with respect to SEQ ID NO:8 and/or the number and kind of "amino acid differences" that may be present in such a binder of the invention (i.e. compared to the sequence of SEQ ID NO:8), it should be noted that, when it is said that (i) 1c81-based binder has a degree of sequence identity with the sequence of SEQ ID NO:8 of at least 85%, preferably at least 90%, more preferably at least 95% (in which the CDRs, any C-terminal extension that may be present, as well as the mutations at positions 11, 89, 110 and/or 112 required by the specific aspect involved, are not taken into account for determining the degree of sequence identity); and/or when it is said that (ii) a 1c81-based binder has no more than 7, preferably no more than 5, such as only 3, 2 or 1 "amino acid differences" with the sequence of SEQ ID NO:8 (again, not taking into account any C-terminal extension that may be present and not taking into account the mutations at positions 11, 89, 110 and/or 112 required by the specific aspect involved), then this also includes sequences that have no amino acid differences with the sequence of SEQ ID NO:8 other than the mutations at positions 11, 89, 110 and/or 112 required by the specific aspect involved) and any C-terminal extension that may be present.

Thus, in one specific aspect of the invention, the 1c81-based binders provided by the invention may have 100% sequence identity with SEQ ID NO:8 (including the CDR's, but not taking into account the mutation(s) or combination of mutations at positions 11, 89, 110 and/or 112 disclosed herein and/or any C-terminal extension that may be present) and/or may have no amino acid differences with SEQ ID NO:8 (i.e. other than the mutation(s) or combination of mutations at positions 11, 89, 110 and/or 112 disclosed herein and any C-terminal extension that may be present).

When any amino acid differences are present (i.e. besides any C-terminal extension and the mutations at positions 11, 89, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the 1c81-based binders provided by the invention have the same CDRs (defined according to the Abm convention) as are present in SEQ ID NO:8.

Also, when a 1c81-based binder that is present in the polypeptides of the invention according to any aspect of the invention has one or more amino acid differences with the sequence of SEQ ID NO:8 (besides the mutations at positions 11, 89, 110 and/or 112 that are required by the specific aspect involved), then some specific, but non-limiting examples of such mutations/amino acid differences that may be present (i.e. compared to the sequences of SEQ ID NO:8) are for example K10G, A14P, L82M, K83R, L45R, H72D, P74S, R75K and/or S77T, or any suitable combination of two or more (and up to and including all) of these mutations, such as for instance depicted by SEQ ID NO:s 129 to 135, 147 to 153 and 162 to 168, of which SEQ ID NO:s 134, 152 and 167 are particularly preferred. Other examples of mutations are (a suitable combination of) one or more suitable "humanizing" substitutions; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions).

Also, when a 1c81-based binder is in monovalent format or present at and/or forms the N-terminal part of the polypeptide of the invention, then it preferably contains a D at position 1 (i.e. an E1D mutation compared to SEQ ID NO:8). Accordingly, in a further aspect, the invention relates to a polypeptide of the invention (which is as further described herein) that has a 1c81-based binder (which is as further described herein) at its N-terminal end, wherein said 1c81-based binder has a D at position 1, such as for instance depicted by SEQ ID NO:s 147 to 153 and 162 to 168 of which SEQ ID NO: 152 and 167 are particularly preferred.

When a 1c81-based binder is in monovalent format or present at and/or form the C-terminal end of the protein, polypeptide or other compound or construct in which they are present (or when they otherwise have an "exposed" C-terminal end in such protein, polypeptide or other compound or construct, by which is generally meant that the C-terminal end of the ISV is not associated with or linked to a constant domain (such as a CH1 domain); reference is again made to WO 2012/175741 and PCT/EP2015/06043), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I), such as for instance depicted by SEQ ID NO:s 162 to 168 of which SEQ ID NO: 167 is particularly preferred.

According to some preferred, but non-limiting examples of such C-terminal extensions $X_{(n)}$, X and n can be as further described herein for the polypeptides of the invention.

When the 1c81-based binders provided by the invention contain mutations at positions 110 or 112 (optionally in combination with mutations at position 11 and/or 89 as described herein), the C-terminal amino acid residues of framework 4 (starting from position 109) can be as follows: (i) if no C-terminal extension is present: VTVKS (SEQ ID NO:72), VTVQS (SEQ ID NO:73), VKVSS (SEQ ID NO:74) or VQVSS (SEQ ID NO:75); or (ii) if a C-terminal extension is present: VTVKSX$_{(n)}$ (SEQ ID NO:76), VTVQSX(n) (SEQ ID NO:77), VKVSSX(n) (SEQ ID NO:78) or VQVSSX$_{(n)}$ (SEQ ID NO:79), such as VTVKSA (SEQ ID NO:80), VTVQSA (SEQ ID NO:81), VKVSSA (SEQ ID NO:82) or VQVSSA (SEQ ID NO:83). When the 1c81-based binders provided by the invention do not contain mutations at positions 110 or 112 (but only mutations at position 11 and/or 89 as described herein), the C-terminal amino acid residues of framework 4 (starting from position 109) will usually be either: (i) when no C-terminal extension is present: VTVSS (SEQ ID NO:84) (as in the sequence of SEQ ID NO:1); or (ii) when a C-terminal extension is present: VTVSSX$_{(n)}$ (SEQ ID NO:85) such as VTVSSA (SEQ ID NO:86). In these C-terminal sequences, X and n are as defined herein for the C-terminal extensions.

Thus, in a first aspect, a 1c81-based binder has:
- a CDR1 (according to Kabat) that is the amino acid sequence FSTSTMG (SEQ ID NO:9); and
- a CDR2 (according to Kabat) that is the amino acid sequence AIDWSDFNTYYADSVKG (SEQ ID NO:10); and
- a CDR3 (according to Kabat) that is the amino acid sequence HSETRGGTRYFDRPSLYNY (SEQ ID NO:11);

and has:
- a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;

and/or has:
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:8), in which:
- the amino acid residue at position 11 of the 1c81-based binder is preferably chosen from L or V; and
- the amino acid residue at position 89 of the 1c81-based binder is preferably suitably chosen from T, V or L; and
- the amino acid residue at position 110 of the 1c81-based binder is preferably suitably chosen from T, K or Q; and
- the amino acid residue at position 112 of the 1c81-based binder is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, a 1c81-based binder that is present in a polypeptide of the invention has:
- a CDR1 (according to Kabat) that is the amino acid sequence FSTSTMG (SEQ ID NO:9); and
- a CDR2 (according to Kabat) that is the amino acid sequence AIDWSDFNTYYADSVKG (SEQ ID NO:10); and
- a CDR3 (according to Kabat) that is the amino acid sequence HSETRGGTRYFDRPSLYNY (SEQ ID NO:11);

and has:
- a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;

and/or has:
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:8), such that said 3c23-based binder comprises the following amino acid residues (i.e. mutations compared to the amino acid sequence of SEQ ID NO:8) at the positions mentioned (numbering according to Kabat):
- 89T; or
- 89L in combination with 11V; or
- 89L in combination with 110K or 110Q; or
- 89L in combination with 112K or 112Q; or
- 89L in combination with 11V and 110K or 110Q; or
- 89L in combination with 11V and 112K or 112Q; or
- 11V in combination with 110K or 110Q; or
- 11V in combination with 112K or 112Q.

As mentioned, when a 1c81-based binder that is present in the polypeptides of the invention is used in a monovalent format and/or is present at the C-terminal end of a polypeptide of the invention (as defined herein), the 1c81-based binder (and consequently, the resulting polypeptide of the invention) preferably has a C-terminal extension X(n) as described herein for the polypeptides of the invention and/or as described in WO 2012/175741 or PCT/EP2015/060643.

As mentioned, in the invention, 1c81-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 1c81-based binders in which position 11 is V and position 89 is L, optionally with a 110K or 110Q mutation.

Thus, in one preferred aspect, a 1c81-based binder that is present in a polypeptide of the invention has:

a CDR1 (according to Kabat) that is the amino acid sequence FSTSTMG (SEQ ID NO:9); and a CDR2 (according to Kabat) that is the amino acid sequence AIDWSDFNTYYADSVKG (SEQ ID NO:10); and a CDR3 (according to Kabat) that is the amino acid sequence HSETRGGTRYFDRPSLYNY (SEQ ID NO:11);

and has:

a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;

and/or has:

no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:8), in which:

the amino acid residue at position 11 of the 1c81-based binder is preferably chosen from L or V; and the amino acid residue at position 89 of the 1c81-based binder is T; and the amino acid residue at position 110 of the 1c81-based binder is preferably suitably chosen from T, K or Q (and is preferably T); and the amino acid residue at position 112 of the 1c81-based binder is preferably suitably chosen from S, K or Q (and in preferably S).

In another preferred aspect, a 1c81-based binder that is present in a polypeptide of the invention has:

a CDR1 (according to Kabat) that is the amino acid sequence FSTSTMG (SEQ ID NO:9); and a CDR2 (according to Kabat) that is the amino acid sequence AIDWSDFNTYYADSVKG (SEQ ID NO:10); and a CDR3 (according to Kabat) that is the amino acid sequence HSETRGGTRYFDRPSLYNY (SEQ ID NO:11);

and has:

a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;

and/or has:

no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);

and optionally (i.e. when in monovalent format or when present at the C-terminal end of a polypeptide of the invention) has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:8), in which:

the amino acid residue at position 11 of the 1c81-based binder is V; and the amino acid residue at position 89 of the 1c81-based binder is L; and the amino acid residue at position 110 of the 1c81-based binder is preferably suitably chosen from T, K or Q; and the amino acid residue at position 112 of the 1c81-based binder is preferably suitably chosen from S, K or Q.

In one specific, but non-limiting aspect, the 1c81-based binders provided by the invention comprise the following amino acid residues (i.e. mutations compared to the sequence of SEQ ID NO:8) at the positions mentioned (numbering according to Kabat):

11V in combination with 89L; or
11V in combination with 110K or 110Q;
11V in combination with 112K or 112Q;
11V in combination with 89L and 110K or 110Q; or
11V in combination with 89L and 112K or 112Q;

and have CDR's (according to Kabat) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):

89L in combination with 11V; or
89L in combination with 110K or 110Q; or
89L in combination with 112K or 112Q; or
89L in combination with 11V and 110K or 110Q; or
89L in combination with 11V and 112K or 112Q;

and have CDR's (according to Kabat) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):

110K or 110Q in combination with 11V; or
110K or 110Q in combination with 89L; or
110K or 110Q in combination with 11V and 89L;
and have CDR's (according to Kabat) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):
112K or 112Q in combination with 11V; or
112K or 112Q in combination with 89L; or
112K or 112Q in combination with 11V and 89L;
and have CDR's (according to Kabat) and have an overall degree of sequence identity with the amino acid sequence of SEQ ID NO:8 that are as described herein.

In another aspect, the 1c81-based binders provided by the invention comprise a T at position 89 and have CDR's (according to Kabat) and have an overall degree of sequence identity with the amino acid sequence of SEQ ID NO:8 that are as described herein.

In another aspect, the 1c81-based binders provided by the invention comprise a V at position 11 and an L at position 89 and have CDR's (according to Kabat) and have an overall degree of sequence identity with the amino acid sequence of SEQ ID NO:8 that are as described herein.

As mentioned, the 1c81-based binders provided by the invention according to the aspects described herein may contain a K10G, A14P, L82M, K83R, L45R, H72D, P74S, R75K and/or S77T mutation, or any suitable combination of two or more (and up to and including all) of these mutations (and again, when the 1c81-based binder is monovalent or present at the N-terminal end of a compound or polypeptide of the invention, preferably also an E1D mutation).

In another aspect, a 1c81-based binder that is present in a polypeptide of the invention has:
  a CDR1 (according to Abm) that is the amino acid sequence GRTFSFSTSTMG (SEQ ID NO:12); and
  a CDR2 (according to Abm) that is the amino acid sequence AIDWSDFNTY (SEQ ID NO:13); and
  a CDR3 (according to Abm) that is the amino acid sequence HSETRGGTRYFDRPSLYNY (SEQ ID NO:11);
and has:
  a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;
and/or has:
  no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and optionally (i.e. when in monovalent format or when present at the N-terminal end of a polypeptide of the invention) has a D at position 1 (i.e. an E1D mutation compared to SEQ ID NO:8),
in which:
  the amino acid residue at position 11 of the 1c81-based binder is preferably chosen from L or V; and
  the amino acid residue at position 89 of the 1c81-based binder is preferably suitably chosen from T, V or L; and
  the amino acid residue at position 110 of the 1c81-based binder is preferably suitably chosen from T, K or Q; and
  the amino acid residue at position 112 of the 1c81-based binder is preferably suitably chosen from S, K or Q;
such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, a 1c81-based binder that is present in a polypeptide of the invention has:
  a CDR1 (according to Abm) that is the amino acid sequence GRTFSFSTSTMG (SEQ ID NO:12); and
  a CDR2 (according to Abm) that is the amino acid sequence AIDWSDFNTY (SEQ ID NO:13); and
  a CDR3 (according to Abm) that is the amino acid sequence HSETRGGTRYFDRPSLYNY (SEQ ID NO:11);
and has:
  a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;
and/or has:
  no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally (i.e. when in monovalent format or when present at the N-terminal end of a polypeptide of the invention) has a D at position 1 (i.e. an E1D mutation compared to SEQ ID NO:8);
such that said 1c81-based binder comprises the following amino acid residues (i.e. mutations compared to the amino acid sequence of SEQ ID NO:8) at the positions mentioned (numbering according to Kabat):
  89T; or
  89L in combination with 11V; or
  89L in combination with 110K or 110Q; or
  89L in combination with 112K or 112Q; or
  89L in combination with 11V and 110K or 110Q; or
  89L in combination with 11V and 112K or 112Q; or
  11V in combination with 110K or 110Q; or
  11V in combination with 112K or 112Q.

As mentioned, when a 1c81-based binder that is present in the polypeptides of the invention is used in a monovalent format and/or is present at the C-terminal end of a polypeptide of the invention (as defined herein), the 1c81-based binder (and consequently, the resulting polypeptide of the invention) preferably has a C-terminal extension X(n), which C-terminal extension may be as described herein for the 1c81-based binders provided by the invention and/or as described in WO 2012/175741 or PCT/EP2015/060643.

As mentioned, in the invention, 1c81-based binders in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are 1c81-based binders in which position 11 is V and position 89 is L, optionally with a 110K or 110Q mutation.

Thus, in one preferred aspect, a 1c81-based binder that is present in a polypeptide of the invention has:
  a CDR1 (according to Abm) that is the amino acid sequence GRTFSFSTSTMG (SEQ ID NO:12); and
  a CDR2 (according to Abm) that is the amino acid sequence AIDWSDFNTY (SEQ ID NO:13); and
  a CDR3 (according to Abm) that is the amino acid sequence HSETRGGTRYFDRPSLYNY (SEQ ID NO:11);
and has:
  a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;
and/or has:
  no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and optionally (i.e. when in monovalent format or when present at the N-terminal end of a polypeptide of the invention) has a D at position 1 (i.e. an E1D mutation compared to SEQ ID NO:8),
in which
  the amino acid residue at position 11 of the 1c81-based binder is preferably chosen from L or V; and
  the amino acid residue at position 89 of the 1c81-based binder is T; and
  the amino acid residue at position 110 of the 1c81-based binder is preferably suitably chosen from T, K or Q (and is preferably T); and
  the amino acid residue at position 112 of the 1c81-based binder is preferably suitably chosen from S, K or Q (and in preferably S).

In another preferred aspect, a 1c81-based binder that is present in a polypeptide of the invention has:
  a CDR1 (according to Abm) that is the amino acid sequence GRTFSFSTSTMG (SEQ ID NO:12); and
  a CDR2 (according to Abm) that is the amino acid sequence AIDWSDFNTY (SEQ ID NO:13); and
  a CDR3 (according to Abm) that is the amino acid sequence HSETRGGTRYFDRPSLYNY (SEQ ID NO:11);
and has:
  a degree of sequence identity with the amino acid sequence of SEQ ID NO:8 (in which any C-terminal extension that may be present as well as the CDRs are not taken into account for determining the degree of sequence identity) of at least 85%, preferably at least 90%, more preferably at least 95%;
and/or has:
  no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:8 (in which said amino acid differences, if present, may be present in the frameworks and/or the CDR's but are preferably present only in the frameworks and not in the CDRs);
and optionally (i.e. when in monovalent format or when present at the C-terminal end of a polypeptide of the invention) has:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and optionally (i.e. when in monovalent format or when present at the N-terminal end of a polypeptide of the invention) has a D at position 1 (i.e. an E1D mutation compared to SEQ ID NO:8),
in which:
  the amino acid residue at position 11 of the 1c81-based binder is V; and
  the amino acid residue at position 89 of the 1c81-based binder is L; and the amino acid residue at position 110 of the 1c81-based binder is preferably suitably chosen from T, K or Q; and the amino acid residue at position 112 of the 1c81-based binder is preferably suitably chosen from S, K or Q.

In one specific, but non-limiting aspect, the 1c81-based binders provided by the invention comprise the following amino acid residues (i.e. mutations compared to the sequence of SEQ ID NO:8) at the positions mentioned (numbering according to Kabat):

11V in combination with 89L; or
11V in combination with 110K or 110Q;
11V in combination with 112K or 112Q;
11V in combination with 89L and 110K or 110Q; or
11V in combination with 89L and 112K or 112Q;

and have CDR's (according to Abm) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):

89L in combination with 11V; or
89L in combination with 110K or 110Q; or
89L in combination with 112K or 112Q; or
89L in combination with 11V and 110K or 110Q; or
89L in combination with 11V and 112K or 112Q;

and have CDR's (according to Abm) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):

110K or 110Q in combination with 11V; or
110K or 110Q in combination with 89L; or
110K or 110Q in combination with 11V and 89L;

and have CDR's (according to Abm) and have an overall degree of sequence identity with the amino acid sequence of SEQ ID NO:8 that are as described herein.

In another specific, but non-limiting aspect, the 1c81-based binders provided by the invention comprise the following amino acid residues (i.e. mutations compared to the sequence of SEQ ID NO:8) at the positions mentioned (numbering according to Kabat):

112K or 112Q in combination with 11V; or
112K or 112Q in combination with 89L; or
112K or 112Q in combination with 11V and 89L;

and have CDR's (according to Abm) and have an overall degree of sequence identity with the amino acid sequence of SEQ ID NO:8 that are as described herein.

In another aspect, the 1c81-based binders provided by the invention comprise a T at position 89 and have CDR's (according to Abm) and have an overall degree of sequence identity with the amino acid sequence of SEQ ID NO:8 that are as described herein.

In another aspect, the 1c81-based binders provided by the invention comprise a V at position 11 and an L at position 89 and have CDR's (according to Abm) and have an overall degree of sequence identity with the amino acid sequence of SEQ ID NO:8 that are as described herein.

Some preferred but non-limiting examples of 1c81-based binder(s) that can be present in the polypeptides of the invention are given in SEQ ID NO's: 43 to 70, and polypeptides of the invention that suitably comprise one or more of these sequences form further aspects of the invention (in each case, preferably with a D at position 1 when at the N-terminal end of the polypeptide and with a C-terminal alanine when at the C-terminal end of the polypeptide). Some particularly preferred 1c81 binders that can be present in the polypeptides of the invention are the sequences of SEQ ID NOs: 52, 53, 66 or 67 or variants thereof with (a suitable combination of) one or more mutations chosen from K10G, A14P, L82M, K83R, L45R, H72D, P74S, R75K and/or S77T such as for instance depicted by SEQ ID NO:s 129 to 135, of which SEQ ID NO: 134 is particularly preferred (again, in each case, preferably with a D at position 1 when at the N-terminal end of the polypeptide, such as e.g. SEQ ID NO:s 147 to 153 of which SEQ ID NO: 152 is particularly preferred and with a C-terminal alanine when at the C-terminal end of the polypeptide, such as e.g. SEQ ID NO:s 162 to 168 of which SEQ ID NO: 167 is particularly preferred).

Polypeptides of the Invention

As mentioned, in further aspects, the invention relates to proteins, polypeptides, constructs, compounds or other chemical entities that comprise or essentially consist of at least one (such as one, two or three) P2X7 receptor binders of the invention (also collectively referred to herein as "polypeptides of the invention" or "compounds of the invention").

These anti-P2X7 receptor polypeptides can for example comprise one or more (such as one or two) 3c23-based building blocks and/or one or more (such as one or two) 1c81-based building blocks, and may in particular either comprise one, two or three (and in particular two) 3c23-based building blocks (and no 1c81-based building blocks) or comprise one, two or three (and in particular two) 1c81-based building blocks (and no 3c23-based building blocks) or can be biparatopic, i.e. comprise one or two (and in particular one) 3c23-based building blocks and one or two (and in particular one) 1c81-based building blocks.

As mentioned, the polypeptides of the invention preferably also have an increased half-life (as defined herein), by which is generally meant that the polypeptide has a half-life (as defined herein) that is at least 2 times, preferably at least 5 times, for example at least 10 times or more than 20 times, greater than the half-life of the monovalent 3c23-based binder that is present in the polypeptide of the invention as well as a half-life (as defined herein) that is at least 2 times, preferably at least 5 times, for example at least 10 times or more than 20 times, greater than the half-life of the monovalent 1c81-based binder that is present in the polypeptide of the invention (as measured in either in man and/or a suitable animal model, such as mouse or cynomolgus monkey).

In particular, a polypeptide of the invention preferably has a half-life (as defined herein) in human subjects of at least 1 day, preferably at least 3 days, more preferably at least 7 days, such as at least 10 days.

In order to provide the polypeptides of the invention with such an (increased) half-life, the polypeptides of the invention preferably contain a serum albumin binding ISVD, and in particular a serum albumin binding Nanobody.

In particular, such a serum albumin binding ISVD or Nanobody may be (single) domain antibody or dAb against human serum albumin as described in for example EP 2 139 918, WO 2011/006915, WO 2012/175400, WO 2014/111550 and may in particular be a serum albumin binding Nanobody as described in WO 2004/041865, WO 2006/122787, WO 2012/175400 or PCT/EP2015/060643. Particularly preferred serum albumin binding ISVDs are the Nanobody Alb-1 (see WO 2006/122787) or its humanized variants such as Alb-8 (WO 2006/122787, SEQ ID NO:62), Alb-23 (WO 2012/175400, SEQ ID NO:1) and other humanized (and preferably also sequence-optimized) variants of Alb-1 and/or variants of Alb-8 or Alb-23 (or more generally ISVDs that have essentially the same CDRs as Alb-1, Alb-8 and Alb-23). The amino acid sequences of some particularly preferred but non-limiting serum albumin binders that can be present in the polypeptides of the invention are given in Figure as SEQ ID NOs: 89 to 92, of which SEQ ID NO's: 90 to 92 are particularly preferred.

Again, as mentioned, such a serum albumin binding ISVD, when present, may contain within its sequence one or more framework mutations that reduce binding by pre-existing antibodies. In particular, when such a serum albumin binding ISVD is a Nanobody or a (single) domain antibody that is, essentially consist of and/or is derived from a VH domain, the serum albumin binding ISVD may contain (a suitable combination of) amino acid residues/mutations at positions 11, 89, 110 and/or 112 that are as described in PCT/EP2015/060643 and/or that essentially are as described herein for the P2X7 binders provided by the invention. For example, PCT/EP2015/060643 describes a number of variants of Alb-1, Alb-8 and Alb-23 that contain amino acid residues/mutations at positions 11, 89, 110 and/or 112 that reduce binding by pre-existing antibodies that can be used in the compounds of the invention.

Again, when such a serum albumin binding ISVD is present at the C-terminal end of a compound of the invention, the serum albumin binding ISVD (and as a result, the compound of the invention) preferably has a C-terminal extension X(n), which C-terminal extension may be as described herein for the P2X7 binders provided by the invention and/or as described in WO 2012/175741 or PCT/EP2015/060643. Also, preferably, at least said C-terminal ISVD has mutations that reduce the binding of pre-existing antibodies, like (a suitable combination of) the amino acid residues/mutations at positions 11, 89, 110 and/or 112 described in PCT/EP2015/060643.

Although the presence/use of a serum albumin binding ISVD is the preferred way of providing the polypeptides of the invention with an increased half-life, other means of increasing the half-life of a compound of the invention (such as the use of other binding domains binding to serum albumin, the use of ISVD's binding to other serum proteins such as transferrin or IgG, PEGylation, fusion to human albumin or a suitable fragment thereof, or the use of a suitable serum albumin-binding peptide), although less preferred, are also included in the scope of the invention.

As mentioned, the polypeptides of the invention preferably also have a C-terminal extension X(n) (as further described herein) and preferably the amino acid residue at position 1 (i.e. at the N-terminal end of the polypeptide) is D.

In the polypeptides of the invention, the P2X7 binders (and the serum albumin binding ISV, if present) can be directly linked to each other or via one or more suitable linkers. Some preferred but non-limiting linkers are a 9GS, 15GS or 35GS linker.

Although less preferred, it is also not excluded that the polypeptides of the invention can, besides the one or more P2X7 binders and the serum albumin binding ISVD (if present), contain one or more other amino acid sequences, chemical entities or moieties. These other amino acid sequences, chemical entities or moieties can confer one or more desired properties to the (resulting) compound of the invention and/or can alter the properties of the (resulting) compound of the invention in a desired manner, for example to provide the (resulting) compound of the invention with a desired biological and/or therapeutic activity, to modify or improve pharmacokinetic and/or pharmacodynamic properties, to target the compound of the invention to specific cells, tissues or organs (including cancer cells and cancer tissues), to provide a cytotoxic effect and/or to serve as a detectable tag or label. Some non-limiting examples of such other amino acid sequences, chemical entities or moieties are:

- one or more binding domains or binding units that are directed against a therapeutically relevant target other than P2X7 (i.e. so as to provide a compound of the invention that (in addition to being biparatopic for P2X7) is bispecific for P2X7 and said other target); and/or
- one or more binding domains or binding units that provide for increased specificity against P2X7 receptor (usually, these will be able to bind to P2X7 receptor but will generally by themselves essentially not be functional against the P2X7 receptor); and/or
- one or more binding domains or binding units that target the compound of the invention to a desired cell, tissue or organ (such as a cancer cell); and/or
- a payload such as a cytotoxic payload; and/or
- a detectable label or tag, such as a radiolabel or fluorescent label; and/or
- a tag that can help with immobilization, detection and/or purification of the compound of the invention, such as a HIS or FLAG3 tag; and/or
- a tag that can be functionalized, such as a C-terminal GGC or GGGC tag.

It is also not excluded from the scope of the invention that the compounds of the invention can also contain one or more parts or fragments of a (preferably human) conventional antibody (such as an Fc part or a functional fragment thereof or one or more constant domains) and/or from a Camelid heavy-chain only antibody (such as one or more constant domains).

When the polypeptides of the invention contain one or more further binding domains or binding units (e.g. as described in the previous paragraphs), these other binding domains or binding units preferably comprise one or more ISVD's, and more preferably are all ISVD's. For example and without limitation, these one or more further binding domains or binding units can be one or more Nanobodies (including a VHH, a humanized VHH and/or a camelized VHs such as camelized human VH's), a (single domain) antibody is a VH domain or that is derived from a VH domain, a dAb that is or essentially consists of a VH domain or that is derived from a VH domain, or even a (single) domain antibody or a dAb that is or essentially consists of VL domain. In particular, these one or more binding domains or binding units, when present, may comprise one or more Nanobodies, and more in particular are all Nanobodies.

When a polypeptide of the invention has an ISVD at its C-terminal end (which C-terminal ISVD may be a P2X7 binder, a serum albumin binding ISVD or another ISVD as referred to in the previous paragraphs), then the polypeptide of the invention (i.e. said C-terminal ISVD) preferably has a C-terminal extension X(n) as described herein.

When a polypeptide of the invention contains, in addition to the one or more P2X7 binders and the serum albumin binding ISVD (if present) any further ISVDs (as referred to in the previous paragraphs), and where such further ISVD's are Nanobodies or are ISVD's that are, that essentially consist of and/or that are derived from VH sequences, then according to a preferred aspect of the invention said one or more (and preferably all) of such ISVDs present in the polypeptide of the invention will contain within their sequence one or more framework mutations that reduce binding by pre-existing antibodies. In particular, according to this aspect of the invention, such further ISVDs may contain (a suitable combination of) amino acid residues/mutations at positions 11, 89, 110 and/or 112 that are as described in PCT/EP2015/060643 and/or that essentially are as described herein for the P2X7. In one specific aspect, when the polypeptide of the invention has an ISVD at its C-terminal end (which C-terminal ISVD may be a P2X7, a serum albumin binding ISVD or another ISVD as referred to in the previous paragraphs), then at least said ISVD that is present at and/or forms the C-terminal has such framework mutations that reduce binding by pre-existing antibodies (and said C-terminal ISVD will preferably also have a C-terminal extension X(n) as described herein).

In one aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  the amino acid residue at position 11 is preferably chosen from L or V; and
  the amino acid residue at position 89 is preferably suitably chosen from T, V or L; and
  the amino acid residue at position 110 is preferably suitably chosen from T, K or Q; and
  the amino acid residue at position 112 is preferably suitably chosen from S, K or Q;
such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  89T; or
  89L in combination with 11V; or
  89L in combination with 110K or 110Q; or
  89L in combination with 112K or 112Q; or
  89L in combination with 11V and 110K or 110Q; or
  89L in combination with 11V and 112K or 112Q; or
  11V in combination with 110K or 110Q; or
  11V in combination with 112K or 112Q.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  the amino acid residue at position 11 is preferably chosen from L or V; and
  the amino acid residue at position 89 is T; and
  the amino acid residue at position 110 is preferably suitably chosen from T, K or Q (and is preferably T); and
  the amino acid residue at position 112 is preferably suitably chosen from S, K or Q (and in preferably S).

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  the amino acid residue at position 11 is V; and
  the amino acid residue at position 89 is L; and
  the amino acid residue at position 110 is preferably suitably chosen from T, K or Q; and
  the amino acid residue at position 112 is preferably suitably chosen from S, K or Q.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  11V in combination with 89L; or
  11V in combination with 110K or 110Q;
  11V in combination with 112K or 112Q;
  11V in combination with 89L and 110K or 110Q; or
  11V in combination with 89L and 112K or 112Q.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  89L in combination with 11V; or
  89L in combination with 110K or 110Q; or
  89L in combination with 112K or 112Q; or
  89L in combination with 11V and 110K or 110Q; or
  89L in combination with 11V and 112K or 112Q.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  110K or 110Q in combination with 11V; or
  110K or 110Q in combination with 89L; or
  110K or 110Q in combination with 11V and 89L.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain the following amino acid residues:
  112K or 112Q in combination with 11V; or
  112K or 112Q in combination with 89L; or
  112K or 112Q in combination with 11V and 89L.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain a T at position 89.

In another aspect, the invention relates to an anti-P2X7 receptor polypeptide that comprises at least one P2X7 binder (as described herein) and optionally one or more other ISVDs (such as a serum albumin binding ISVD), in which all of the ISVDs present in said polypeptide contain a V at position 11 and an L at position 89.

Again, all these biparatopic anti-P2X7 receptor polypeptide preferably contain a C-terminal extension X(n) (as described herein) and a D at position 1, and as further described herein may contain a serum albumin binding ISVD.

It will be clear from the disclosure herein that the anti-P2X7 polypeptides provided by the invention can have different "formats", i.e. essentially be monovalent, bivalent or trivalent, can be monospecific, bispecific, trispecific etc., and can be biparatopic (as defined herein and in for example WO 08/020079). For example, a compound of the invention can be:

- (essentially) monovalent, i.e. (essentially) comprising a single P2X7 receptor binder of the invention. As mentioned, when used in monovalent format, a P2X7 receptor binder of the invention preferably has a C-terminal extension X(n) as further described herein. Such a compound of the invention may also be half-life extended;
- can be (essentially) bivalent or trivalent and monospecific. Such a compound of the invention will comprise two or more ISVD's against P2X7 receptor, which may be the same or different and when different may be directed against the same epitope or P2X7 receptor or against different epitopes on P2X7 receptor (in the latter case, so as to provide a biparatopic or multiparatopic compound of the invention). Such a compound of the invention may also be half-life extended;
- can be (essentially) bivalent, trivalent (or multivalent) and bispecific or trispecific (or multispecific). Such a compound of the invention will be directed against P2X7 receptor and at least one other target. As described herein, said other target may for example be another therapeutically relevant target (i.e. other than P2X7 receptor) so as to provide a compound of the invention that is bispecific with regard to P2X7 receptor and said other therapeutic target. Said other target may also be a target that provides for increased half-life (such as human serum albumin), so as to provide a compound of the invention that has increased half-life. As also mentioned herein, such other target may allow also for the compound of the invention to be targeted to specific cells, tissues or organs). It is also possible to combine these approaches/ISVDs, for example to provide a compound of the invention that is bispecific for P2X7 receptor and for at least one other therapeutically relevant target and that is half-life extended.

Again, these polypeptides are all preferably as further described herein.

As will be clear to the skilled person, when a compound of the invention is intended for topical use (i.e. on the skin or in the eye) or is for example meant to have a (localized) therapeutic action somewhere in for example the GI tract (gastro-intestinal tract; i.e. after oral administration or administration by suppository) or in the lungs (i.e. after administration by inhalation) or is otherwise meant to be directly applied to its intended place of action (for example, by direct injection), a compound of the invention will usually not require half-life extension. Also, for treatment of certain acute conditions or indications, it may be preferable not to have a prolonged half-life. In these cases, the use of a monovalent compound of the invention or of a another compound of the invention without half-life extension (for example, a compound of the invention that is bivalent or biparatopic with respect to P2X7 receptor).

Some preferred, but non-limiting examples of such compounds of the invention are schematically represented in Table D-1 below, and each of these forms a further aspect of the invention (it should also be noted that when two or more 3c23-based binders are present in a polypeptide of the invention, they may be the same or different, and when they are different, they preferably all contain (a suitable combination of) mutations at positions 11, 89, 110 and/or 112 as described herein, and preferably also have the same CDR's as described herein. The same applies when two or more 1C81-based binders are present in a polypeptides of the invention). Other examples of suitable compounds of the invention without half-life extension will be clear to the skilled person based on the disclosure herein. Some preferred examples of biparatopic polypeptides of the invention will be given in Tables E-1 and E-2 below.

TABLE D-1

Schematic representation of some polypeptides of the invention without a half-lite extending ISVD.

[3c23]
[3c23]-X(n)
[3c23]-[3c23]
[3c23]-[3c23]-X(n)
[1c81]
[1c81]-X(n)
[1c81]-[1c81]
[1c81]-[1c81]-X(n)

Legend:
"[3c23]" represents a 3c23 building block of the invention
"[1c81]" represents a 1c81 building block of the invention
"-" represents either a direct covalent linkage or a suitable linker, such as a 9GS, 15GS or 35GS linker
"X(n)" represents a C-terminal extension as defined herein such as a single alanine residue.

As will be clear to the skilled person, when a compound of the invention is intended for systemic administration and/or for prevention and/or treatment of a chronic disease or disorder, it will usually be preferred that said compound of the invention has increased half-life (as defined herein), i.e. compared to the P2X7 receptor binder(s) present in such compound of the invention. More preferably, such a compound of the invention will contain a half-life extending ISVD such as, preferably, an ISVD and in particular a Nanobody binding to human serum albumin (as described herein).

Some preferred, but non-limiting examples of such compounds of the invention are schematically represented in Table D-2 below, and each of these forms a further aspect of the invention. Other examples of suitable compounds of the invention with half-life extension will be clear to the skilled person based on the disclosure herein. Generally, for compounds of the invention with half-life extension, the presence of a C-terminal extension is much preferred.

TABLE D-2

Schematic representation of some polypeptides of the invention of the invention with a half-life extending ISVD.

[3c23]-[HLE]
[HLE]-[3c23]
[3c23]-[HLE]-X(n)
[HLE]-[3c23]-X(n)
[3c23]-[3c23]-[HLE]
[3c23]-[HLE]-[3c23]
[HLE]-[3c23]-[3c23]
[3c23]-[3c23]-[HLE]-X(n)
[3c23]-[HLE]-[3c23]-X(n)
[HLE]-[3c23]-[3c23]-X(n)
[1c81]-[HLE]
[HLE]-[1c81]
[1c81]-[HLE]-X(n)
[HLE]-[1c81]-X(n)
[1c81]-[1c81]-[HLE]

TABLE D-2-continued

Schematic representation of some polypeptides of the invention of the invention with a half-life extending ISVD.

[1c81]-[HLE]-[1c81]
[HLE]-[1c81]-[1c81]
[1c81]-[1c81]-[HLE]-X(n)
[1c81]-[HLE]-[1c81]-X(n)
[HLE]-[1c81]-[1c81]-X(n)

Legend:
"[3c23]" represents a 3c23 building block of the invention
"[1c81]" represents a 1c81 building block of the invention
"[HLE]" represents a half-life extending binding domain or binding unit (and in particular a half-life extending ISVD), such as an ISVD (and in particular Nanobody) against (human) serum albumin
"-" represents either a direct covalent linkage or a suitable linker, such as a 9GS, 15GS or 35GS linker
"X(n)" represents a C-terminal extension as defined herein such as a single alanine residue.

FIG. 4A gives as SEQ ID NOs: 93 to 98 some non-limiting examples of compounds of the invention of the general formula [3c23]-[3c23]-[HLE]. The 3c23 building blocks used carry either L11V+V89L mutations or V11V+V89L+T110K mutations. The serum albumin binder is either SEQ ID NO: 89 or the albumin binder of SEQ ID NO: 89 with L11V+V89L mutations or L11V+V89L+T110K mutations, which mutations reduce binding by pre-existing antibodies and are preferred. The linkers are 35GS and 9GS linkers, respectively. The polypeptides have a D at position 1 and carry a C-terminal alanine. FIG. 4A also gives as SEQ ID NO: 144 a non-limiting example of a compound of the invention of the general formula [3c23]-[3c23]-[HLE] which is humanized.

FIG. 4B gives as SEQ ID NOs: 99 to 104 some non-limiting examples of compounds of the invention of the general formula [1c81]-[1c81]-[HLE]. The 1c81 building blocks used carry either L11V+V89L mutations or V11V+V89L+T110K mutations. The serum albumin binder is either SEQ ID NO: 89 or the albumin binder of SEQ ID NO: 89 with L11V+V89L mutations or L11V+V89L+T110K mutations, which mutations reduce binding by pre-existing antibodies and are preferred. The linkers are 35GS and 9GS linkers, respectively. The polypeptides have a D at position 1 and carry a C-terminal alanine. FIG. 4B also gives as SEQ ID NO: 145 a non-limiting example of a compound of the invention of the general formula [1c81]-[1c81]-[HLE] which is humanized.

Biparatopic Polypeptides Provided by the Invention

As mentioned, in one specifically preferred embodiment, the invention provides biparatopic anti-P2X7 receptor polypeptides. In particular, the biparatopic anti-P2X7 polypeptides provided by the invention comprise at least one (such as one or two) 3c23-based binder as described herein and at least one (such as one or two) 1c81-based binder as described herein.

Thus, in a further aspect, the invention relates to a polypeptide (which is preferably a fusion protein) that comprises at least one (such as one or two) 3c23-based binder as described herein and at least one (such as one or two) 1c81-based binder as described herein.

The biparatopic polypeptides provided by the invention may have an increased half-life (as generally described herein for the polypeptides of the invention) and for this purpose may contain a serum-albumin binding ISVD (again, as generally described herein for the polypeptides of the invention).

Thus, in a further aspect, the invention relates to a polypeptide (which is preferably a fusion protein) that comprises at least one (such as one or two) 3c23-based binder as described herein and at least one (such as one or two) 1c81-based binder as described herein, wherein said polypeptide has a half-life (as defined herein) in human subjects of at least 1 day, preferably at least 3 days, more preferably at least 7 days, such as at least 10 days.

In a further aspect, the invention relates to a polypeptide (which is preferably a fusion protein) that comprises at least one (such as one or two) 3c23-based binder as described herein and at least one (such as one or two) 1c81-based binder as described herein and at least one (and preferably one) serum albumin binding ISVD (and in particular a serum albumin binding Nanobody). Again, said polypeptide preferably has a half-life (as defined herein) in human subjects of at least 1 day, preferably at least 3 days, more preferably at least 7 days, such as at least 10 days.

As mentioned, the biparatopic polypeptides of the invention preferably also have a C-terminal extension X(n) (as further described herein) and preferably the amino acid residue at position 1 (i.e. at the N-terminal end of the polypeptide) is D.

In the biparatopic polypeptides of the invention, the 3c23-based binder(s) and 1c81-based binder(s) (and the serum albumin binding ISV, if present) can again be directly linked to each other or via one or more suitable linkers. Some preferred but non-limiting linkers are a 9GS, 15GS or 35GS linker.

Although less preferred, it is also not excluded that the polypeptides of the invention can, besides the one or more 3c23-based binders, the one or more 1c81-based binders and the serum albumin binding ISVD (if present), contain one or more other amino acid sequences, chemical entities or moieties, as generally described herein for the compounds of the invention. Again, these other binding domains or binding units preferably comprise one or more ISVD's, and more preferably are all ISVD's, and again when the biparatopic polypeptide has an ISVD at its C-terminal end, then the polypeptide of the invention (i.e. said C-terminal ISVD) preferably has a C-terminal extension X(n) as described herein. Again, all ISVDs present will preferably contain within their sequence one or more framework mutations that reduce binding by pre-existing antibodies, and in particular amino acid residues/mutations at positions 11, 89, 110 and/or 112 that are as described in PCT/EP2015/060643 and/or that essentially are as described herein for the P2X7 binders. Also, the biparatopic polypeptides of the invention preferably have a D at position 1.

In one aspect, the invention relates to a biparatopic anti-P2X7 receptor polypeptide that comprises at least one 3c23 binder (as described herein) and at least one 1c81 binder (as described herein) (which bispecific polypeptide is as further described herein), in which all of the ISVDs present in said polypeptide contain the following amino acid residues:

the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- 89T; or
- 89L in combination with 11V; or
- 89L in combination with 110K or 110Q; or
- 89L in combination with 112K or 112Q; or
- 89L in combination with 11V and 110K or 110Q; or
- 89L in combination with 11V and 112K or 112Q; or
- 11V in combination with 110K or 110Q; or
- 11V in combination with 112K or 112Q.

In another aspect, the invention relates to a biparatopic anti-P2X7 receptor polypeptide that comprises at least one 3c23 binder (as described herein) and at least one 1c81 binder (as described herein) (which bispecific polypeptide is as further described herein), in which all of the ISVDs present in said polypeptide contain the following amino acid residues:
- the amino acid residue at position 11 is preferably chosen from L or V; and
- the amino acid residue at position 89 is T; and
- the amino acid residue at position 110 is preferably suitably chosen from T, K or Q (and is preferably T); and
- the amino acid residue at position 112 is preferably suitably chosen from S, K or Q (and in preferably S).

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- the amino acid residue at position 11 is V; and
- the amino acid residue at position 89 is L; and
- the amino acid residue at position 110 is preferably suitably chosen from T, K or Q; and
- the amino acid residue at position 112 is preferably suitably chosen from S, K or Q.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- 11V in combination with 89L; or
- 11V in combination with 110K or 110Q;
- 11V in combination with 112K or 112Q;
- 11V in combination with 89L and 110K or 110Q; or
- 11V in combination with 89L and 112K or 112Q.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- 89L in combination with 11V; or
- 89L in combination with 110K or 110Q; or
- 89L in combination with 112K or 112Q; or
- 89L in combination with 11V and 110K or 110Q; or
- 89L in combination with 11V and 112K or 112Q.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- 110K or 110Q in combination with 11V; or
- 110K or 110Q in combination with 89L; or
- 110K or 110Q in combination with 11V and 89L.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain the following amino acid residues:
- 112K or 112Q in combination with 11V; or
- 112K or 112Q in combination with 89L; or
- 112K or 112Q in combination with 11V and 89L.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain a T at position 89.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which all of the ISVDs present in said polypeptide contain a V at position 11 and an L at position 89.

In another aspect, the invention relates to a biparatopic anti-P2X7 receptor polypeptide that comprises at least one 3 c23 binder (as described herein) and at least one 1c81 binder (as described herein) (which biparatopic polypeptide is as further described herein), in which the 3c23 binder is suitably chosen from SEQ ID NOs: 15 to 42 and 136 to 143 and 169-176 or variants thereof with a (suitable combination of) one or more mutations chosen from A14P, G60A, D73N, A74S, P79Y and/or K83R, or any suitable combination of two or more (and up to and including all) of these mutations (again, in each case, preferably with a D at position 1 when at the N-terminal of the polypeptide, such as e.g. SEQ ID NO:s 154 to 161, and with a C-terminal alanine when at the C-terminal end of the polypeptide, such as e.g. SEQ ID NO:s 169 to 176. end of the polypeptide and with a C-terminal alanine when at the C-terminal end of the polypeptide, and in which the 1c81 binder is suitably chosen from SEQ ID NOs: 43 to 70 and 129 to 135 or from variants thereof with (a suitable combination of) one or more mutations chosen from K10G, A14P, L82M, K83R, L45R, H72D, P74S, R75K and/or S77T (again, in each case, preferably with a D at position 1 when at the N-terminal end of the polypeptide, such as e.g. SEQ ID NO:s 147 to 153 of which SEQ ID NO: 152 is particularly preferred and with a C-terminal alanine when at the C-terminal end of the polypeptide, such as e.g. SEQ ID NO:s 162 to 168 of which SEQ ID NO: 167 is particularly preferred.

In another aspect, the invention relates to a biparatopic anti-P2X7 receptor polypeptide that comprises at least one 3c23 binder (as described herein) and at least one 1c81 binder (as described herein) (which biparatopic polypeptide is as further described herein), in which the 3c23 binder is suitably chosen from SEQ ID NOs: 24, 25, 38, 39, 136, 137, 138, 139, 140, 141, 142 and 143, or variants thereof with a (suitable combination of) one or more mutations chosen from A14P, G60A, D73N, A74S, P79Y and/or K83R, or any suitable combination of two or more (and up to and including all) of these mutations, (again, in each case, preferably with a D at position 1 when at the N-terminal end of the polypeptide, such as e.g. SEQ ID NO:s 154, 155, 156, 157, 158, 159, 160 and 161, and with a C-terminal alanine when at the C-terminal end of the polypeptide such as e.g. SEQ ID NO:s 169, 170, 171, 172, 173, 174, 175 and 176, and in which the 1c81 binder is suitably chosen from SEQ ID NOs: 52, 53, 66, 67, 129, 130, 131, 132, 133, 134 and 135, or from variants thereof with (a suitable combination of) one or more mutations chosen from K10G, A14P, L82M, K83R, L45R, H72D, P74S, R75K and/or S77T (again, in each case, preferably with a D at position 1 when at the N-terminal end of the polypeptide such as e.g. SEQ ID NO:s 147, 148, 149, 150, 151, 152 and 153 of which SEQ ID NO: 152 is particularly preferred, and with a C-terminal alanine when at the C-terminal end of the polypeptide, such as e.g. SEQ ID NO:s 162, 163, 164, 165, 166, 167 and 168 of which SEQ ID NO: 167 is particularly preferred).

Again, all these biparatopic anti-P2X7 receptor polypeptide preferably contain a C-terminal extension X(n) (as described herein) and a D at position 1, and as further described herein may contain a serum albumin binding ISVD.

It will be clear from the disclosure herein that biparatopic polypeptides of the invention can have different "formats". For example and without limitation, a biparatopic polypeptide of the invention can:

- essentially consist of one 3c23-based binder (as described herein) and one 1c81-based binder (as described herein);
- essentially consist of two 3c23-based binders (as described herein) and one 1c81-based binder (as described herein);
- essentially consist of one 3c23-based binder (as described herein) and two 1c81-based binders (as described herein);
- essentially consist of two 3c23-based binders (as described herein) and two 1c81-based binders (as described herein);
- essentially consist of one 3c23-based binder (as described herein), one 1c81-based binder (as described herein) and one ISVD against human serum albumin (as described herein);
- essentially consist of two 3c23-based binders (as described herein), one 1c81-based binder (as described herein) and one ISVD against human serum albumin (as described herein);
- essentially consist of one 3c23-based binder (as described herein), two 1c81-based binders (as described herein) and one ISVD against human serum albumin (as described herein); or
- essentially consist of two 3c23-based binders (as described herein), two 1c81-based binders (as described herein) and one ISVD against human serum albumin (as described herein).

Other suitable formats for a biparatopic polypeptide of the invention will be clear to the skilled person based on the disclosure herein.

As will be clear to the skilled person, when a biparatopic polypeptide of the invention is intended for topical use (i.e. on the skin or in the eye) or is for example meant to have a (localized) therapeutic action somewhere in for example the GI tract (i.e. after oral administration or administration by suppository) or in the lungs (i.e. after administration by inhalation) or is otherwise meant to be directly applied to its intended place of action (for example, by direct injection), a polypeptide of the invention will usually not require half-life extension. In these cases, the use of a bivalent bispecific polypeptide of the invention or of another polypeptide of the invention without half-life extension may be preferred.

Some preferred, but non-limiting examples of biparatopic polypeptides of the invention without half-life extension are schematically represented in Table E-1 below, and each of these forms a further aspect of the invention (again, when two or more 3c23-based binders are present in a biparatopic polypeptide of the invention, they may be the same or different, and when they are different, they preferably all contain (a suitable combination of) mutations at positions 11, 89, 110 and/or 112 as described herein, and preferably also have the same CDR's as described herein. The same applies when two or more 1C81-based binders are present in a biparatopic polypeptide of the invention). Other examples of suitable biparatopic polypeptides of the invention without half-life extension will be clear to the skilled person based on the disclosure herein. Again, these polypeptides preferably have a D at position 1.

TABLE E-1

Schematic representation of some biparatopic polypeptides of the invention without a half-life extending ISVD.

[3c23]-[1c81]
[3c23]-[1c81]-X(n)
[3c23]-[3c23]-[1c81]
[3c23]-[3c23]-[1c81]-X(n)
[3c23]-[1c81]-[3c23]
[3c23]-[1c81]-[3c23]-X(n)
[3c23]-[1c81]-[1c81]
[3c23]-[1c81]-[1c81]-X(n)
[1c81]-[3c23]
[1c81]-[3c23]-X(n)
[1c81]-[1c81]-[3c23]
[1c81]-[1c81]-[3c23]-X(n)
[1c81]-[3c23]-[1c81]
[1c81]-[3c23]-[1c81]-X(n)
[1c81]-[3c23]-[3c23]
[1c81]-[3c23]-[3c23]-X(n)

Legend:
"[3c23]" = 3c23-based binder as described herein
"[1c81]" = 1c81 -based binder as described herein
"-" = suitable linker (such as 9GS, 15GS or 35GS)
"X(n)" = C-terminal extension (as described herein)

As will be clear to the skilled person, when a biparatopic polypeptide of the invention is intended for systemic administration and/or for prevention and/or treatment of a chronic disease or disorder, it will usually be preferred that said biparatopic polypeptide of the invention has increased half-life (as defined herein), i.e. compared to the 1c81-based binder(s) present in such polypeptide of the invention. More preferably, such a biparatopic polypeptide of the invention will contain a half-life extending ISVD such as, preferably, an ISVD and in particular a Nanobody binding to human serum albumin (as described herein).

Some preferred, but non-limiting examples of such biparatopic polypeptides of the invention are schematically represented in Table E-2 below, and each of these forms a further aspect of the invention. Other examples of suitable biparatopic polypeptides of the invention with half-life extension will be clear to the skilled person based on the disclosure herein. Generally, for biparatopic polypeptides of the invention with half-life extension, the presence of a C-terminal extension is much preferred. Again, these polypeptides preferably have a D at position 1.

TABLE E-2

Schematic representation of some biparatopic polypeptides of the invention with a half-life extending ISVD.

[3c23]-[1c81]-[HLE]
[3c23]-[1c81]-[HLE]-X(n)
[3c23]-[HLE]-[1c81]
[3c23]-[HLE]-[1c81]-X(n)
[HLE]-[3c23]-[1c81]
[HLE]-[3c23]-[1c81]-X(n)
[1c81]-[3c23]-[HLE]
[1c81]-[3c23]-[HLE]-X(n)
[1c81]-[HLE]-[3c23]
[1c81]-[HLE]-[3c23]-X(n)
[HLE]-[1c81]-[3c23]
[HLE]-[1c81]-[3c23]-X(n)
[3c23]-[3c23]-[1c81]-[HLE]-X(n)
[3c23]-[1c81]-[3c23]-[HLE]-X(n)
[3c23]-[1c81]-[1c81]-[HLE]-X(n)
[1c81]-[1c81]-[3c23]-[HLE]-X(n)
[1c81]-[3c23]-[1c81]-[HLE]-X(n)
[1c81]-[3c23]-[3c23]-[HLE]-X(n)
[3c23]-[3c23]-[1c81]-[1c81]-[HLE]-X(n)
[1c81]-[1c81]-[3c23]-[3c23]-[HLE]-X(n)

Legend:
"[3c23-based binder]" = 3c23-based binder as described herein
"[1c81-based binder]" = 1c81 -based binder as described herein
"[HLE]" = serum albumin binding ISVD
"-" = suitable linker (such as 9GS, 15GS or 35GS)
"X(n)" = C-terminal extension (as described herein)

FIG. 4C gives as SEQ ID NOs: 105 to 128 some non-limiting examples of biparatopic compounds of the invention of the general formula [3c23]-[1c81]-[HLE] (SEQ ID NOs: 105 to 116) or [1c81]-[3c23]-[HLE] (SEQ ID NOs: 117 to 128). The 3c23 and 1c81 building blocks used carry either L11V+V89L mutations or V11V+V89L+T110K mutations. The serum albumin binder is either SEQ ID NO: 89 or the albumin binder of SEQ ID NO: 89 with L11V+V89L mutations or L11V+V89L+T110K mutations, which mutations reduce binding by pre-existing antibodies and are preferred. The linkers are 35GS and 9GS linkers, respectively. The polypeptides have a D at position 1 and carry a C-terminal alanine. FIG. 4C also gives as SEQ ID NO: 146 a non-limiting example of a biparatopic compound of the invention of the general formula [3c23]-[1c81]-[HLE] which is humanized.

Further Aspects of the Invention

The invention also relates to nucleotide sequences or nucleic acids that encode the polypeptides of the invention as described herein. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 2004/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), polypeptides of the invention Again, such host cells can be generally as described in the published patent applications of Ablynx N.V., such as for example WO 2004/041862, WO 2006/122786, WO 2008/020079, WO 2008/142164 or WO 2009/068627.

The invention also relates to a method for preparing the polypeptides of the invention, which method comprises cultivating or maintaining a host cell as described herein under conditions such that said host cell produces or expresses an amino acid sequence, fusion protein or construct as described herein, and optionally further comprises isolating the polypeptide of the invention so produced. Again, such methods can be performed as generally described in the published patent applications of Ablynx N.V., such as for example WO 2004/041862, WO 2006/122786, WO 2008/020079, WO 2008/142164 or WO 2009/068627.

The invention also relates to a pharmaceutical composition that comprises at least one polypeptide of the invention, and optionally at least one pharmaceutically acceptable carrier, diluent or excipient. Such preparations, carriers, excipients and diluents may generally be as described in the published patent applications of Ablynx N.V., such as for example WO 2004/041862, WO 2006/122786, WO 2008/020079, WO 2008/142164 or WO 2009/068627.

However, since the preferred polypeptides of the invention have an increased half-life, they are preferably administered to the circulation. As such, they can be administered in any suitable manner that allows the polypeptides of the invention to enter the circulation, such as intravenously, via injection or infusion, or in any other suitable manner (including oral administration, subcutaneous administration, intramuscular administration, administration through the skin, intranasal administration, administration via the lungs, etc.) that allows the polypeptides of the invention to enter the circulation. Suitable methods and routes of administration will be clear to the skilled person, again for example also from the teaching of the published patent applications of Ablynx N.V., such as for example WO 2004/041862, WO 2006/122786, WO 2008/020079, WO 2008/142164 or WO 2009/068627.

Thus, in another aspect, the invention relates to a method for the prevention and/or treatment of at least one disease or disorder that can be prevented or treated by the use of a polypeptide of the invention, which method comprises administering, to a subject in need thereof, a pharmaceutically active amount of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, which method comprises administering, to a subject suffering from or at risk of the diseases and disorders mentioned herein, a pharmaceutically active amount of a polypeptide of the invention, and/or of a pharmaceutical composition comprising the same.

The polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the polypeptides of the invention to be used, the specific route of administration and the specific pharmaceutical formulation or composition used, the polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, in particular a mammal, and more in particular a human being. As will be clear to the skilled person, the subject to be treated will in particular be a person suffering from, or at risk from, the diseases and disorders mentioned herein.

As the P2X7 receptor binders and compounds of the invention are capable of binding to P2X7 receptor, they can in particular be used for the prevention and or treatment of diseases or disorders that are associated with P2X7, the P2X7 receptor or the P2X7 signalling pathway and/or that can be prevented, treated or alleviated by modulating the P2X7 signalling pathway. These include, but are not limited to diseases such as inflammatory bowel disease (IBD), rheumatoid arthritis, osteoarthritis, cancer, diabetes, nephritis, neuropathic pain, epilepsy, neurodegenerative diseases such as Alzheimer's disease and Huntington's disease, multiple sclerosis and cardiovascular diseases, including stroke and hypertension, ischemia, as well as other disorders and diseases described herein. In particular, the polypeptides and compositions of the present invention can be used for the diagnosis, prevention and treatment of diseases involving P2X7 mediated disorders.

Other aspects, embodiments, advantages and applications of the invention will become clear from the further description herein.

The invention will now be further described by means of the following non-limiting preferred aspects, examples and figures, in which:

FIG. 1 is a table listing some of the amino acid positions that will be specifically referred to herein and their numbering according to some alternative numbering systems (such as Aho and IMGT);

FIG. 2 lists the amino acid sequences referred to herein;

FIG. 3A shows an alignment of the sequence of Reference A (SEQ ID NO:1) with 3c23 (SEQ ID NO:87) and the 3c23-based building blocks of SEQ ID NOs: 15 to 42;

FIG. 3B shows an alignment of the sequence of Reference B (SEQ ID NO:8) with 1c81 ((SEQ ID NO:88) and the 1c81-based building blocks of SEQ ID NOs: 43 to 70;

Figure 5:
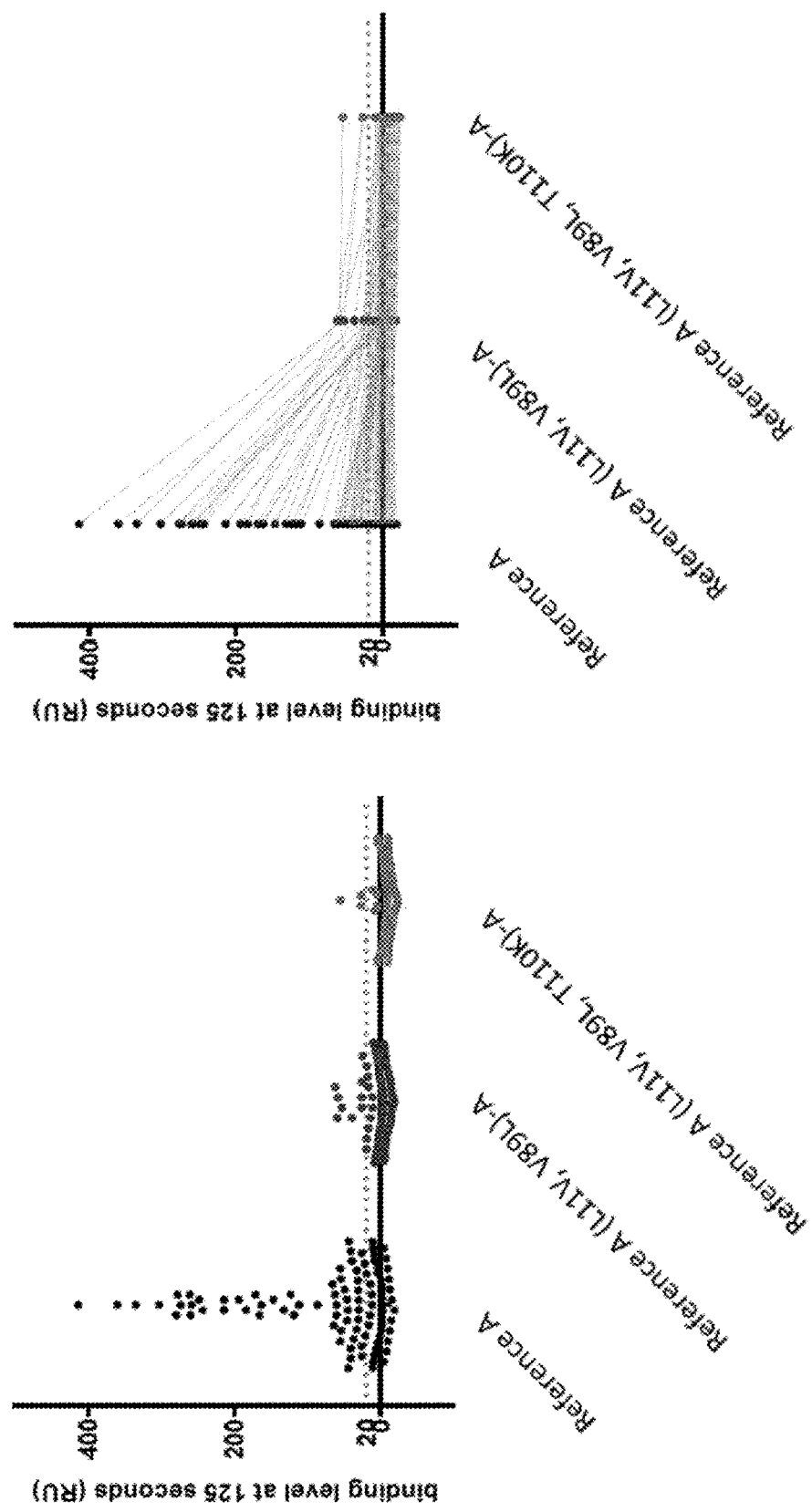
Figure 7:
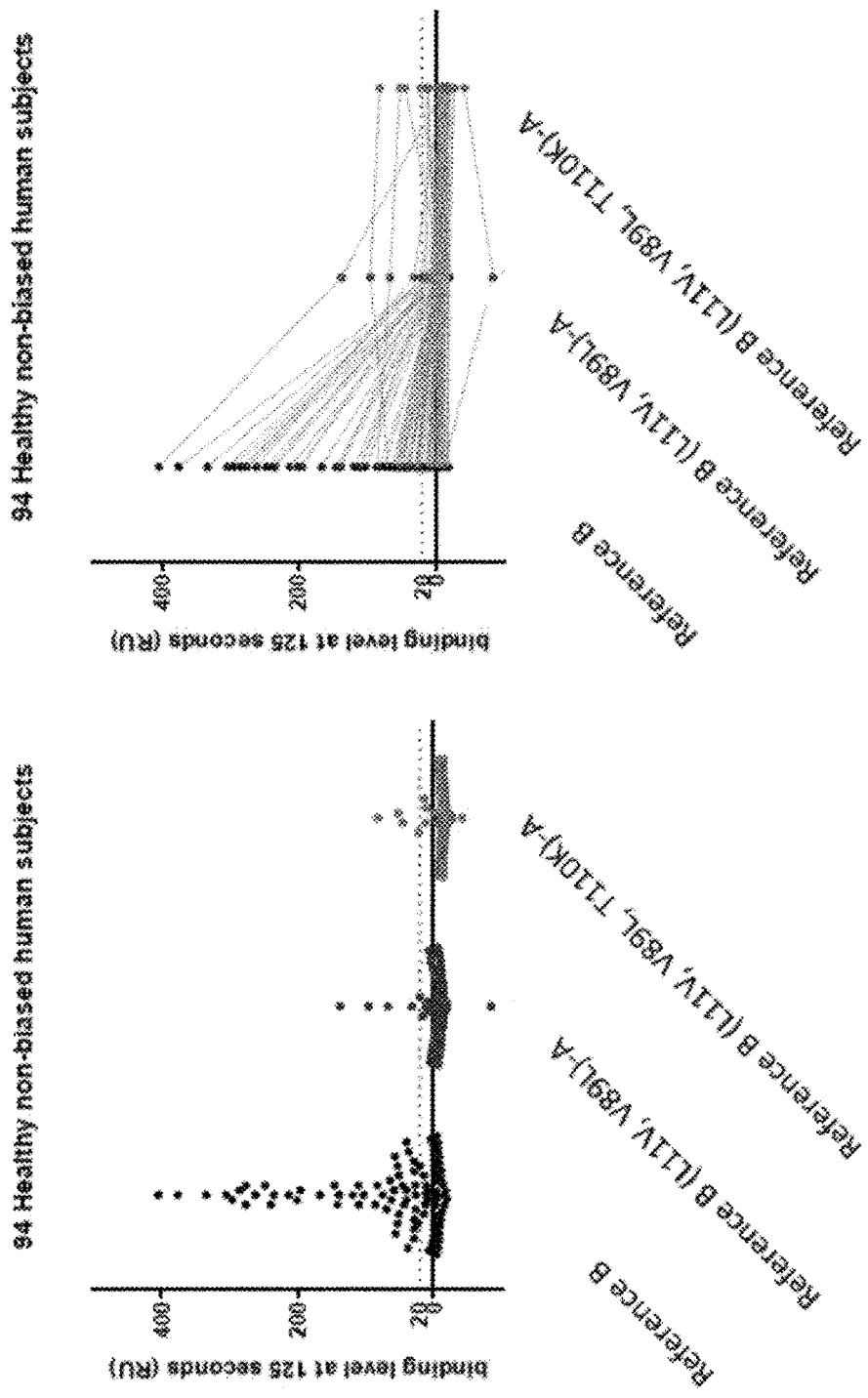

FIG. 4 gives the amino acid sequences of some exemplary polypeptides of the invention;

FIG. 5 shows two corresponding plots of data points obtained in Example 1 when 96 serum samples from human healthy subjects were tested for binding to Reference A and two representative variants of Reference A according to the invention (i.e. [Reference A+L11V+V89L+C-terminal alanine] and [Reference A+L11V+V89L+T110K+C-terminal alanine], respectively). Each dot represents the binding level for one of the 96 samples tested. The data points shown in the right hand panel and the left hand panel are the same; in the right hand panel the data points measured with each individual sample for each of the three compounds tested (i.e. Ref. A; Ref. A+L11V+V89L+114A; and Ref. A+L11V+V89L+T110K+114A) are connected by means of a line (as a result, the declination of the line gives an indication of the extent to which binding by pre-existing antibodies is reduced when the mutations of the invention and the C-terminal alanine are introduced);

FIG. 6 is a table listing the binding data (3 columns giving normalized PreAb binding levels (RU at 125 seconds) and 2 columns giving percentage of reduction in PreAb binding compared to the reference compound used, respectively) of the data points compiled in FIG. 4;

FIG. 7 shows two corresponding plots of data points obtained in Example 2 when 96 serum samples from human healthy subjects were tested for binding to Reference B and two representative variants of Reference B according to the invention (i.e. [Reference B+L11V+V89L+C-terminal alanine] and [Reference B+L11V+V89L+T110K+C-terminal alanine], respectively). Each dot represents the binding level for one of the 96 samples tested. The data points shown in the right hand panel and the left hand panel are the same; in the right hand panel the data points measured with each individual sample for each of the three compounds tested (i.e. Ref. B; Ref. B+L11V+V89L+114A; and Ref. B+L11V+V89L+T110K+114A) are connected by means of a line (as a result, the declination of the line gives an indication of the extent to which binding by pre-existing antibodies is reduced when the mutations of the invention and the C-terminal alanine are introduced);

FIG. 8 is a table listing the binding data (3 columns giving normalized PreAb binding levels (RU at 125 seconds) and 2 columns giving percentage of reduction in PreAb binding compared to the reference compound used, respectively) of the data points compiled in FIG. 7.

FIG. 9 shows inhibition of ATP-mediated calcium uptake of anti-P2X7 1c81 SO variants in Hek-mP2X7 cells. Panel A: Calcium uptake measured directly after ATP addition of variants at 100 nM and 10 nM concentrations. Panel B: Calcium uptake recorded over time of variants tested at 100 nM concentration.

Figure 10:
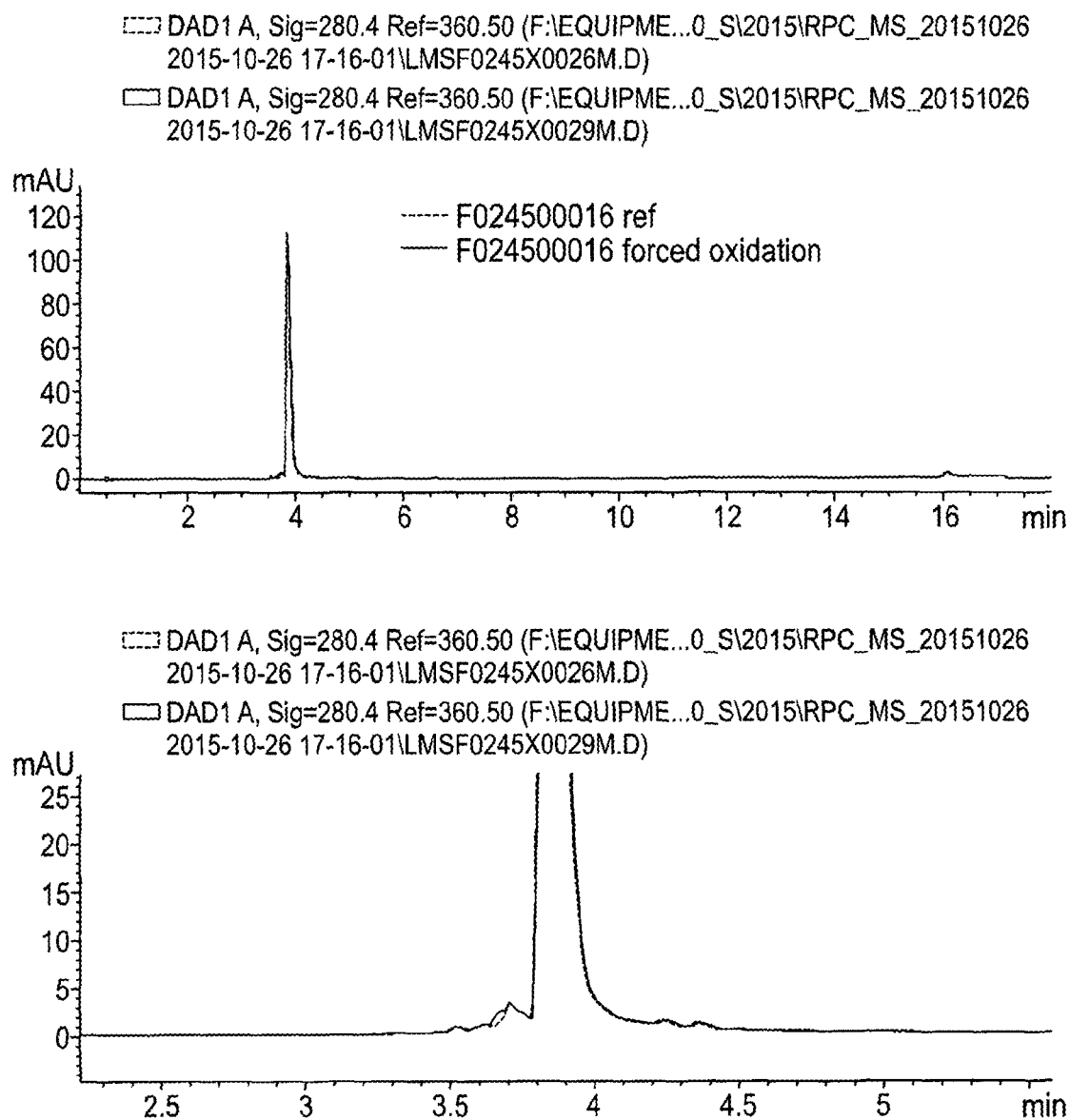

FIG. 10. Overlay of UV 280 nm chromatograms of the intact mass LC-MS analysis of F024500016 control and forced oxidation sample.

FIG. 11. Overlay of UV 280 nm chromatograms of the intact mass LC-MS analysis of F024500016 control and temperature stressed samples.

EXPERIMENTAL PART

The human samples used in the Experimental Part below were either obtained from commercial sources or from human volunteers (after all required consents and approvals were obtained) and were used in according with the applicable legal and regulatory requirements (including but not limited to those regarding medical secret and patient privacy)

In the Examples below, unless explicitly indicated otherwise, the binding of pre-existing antibodies that are present in the samples used to the Nanobodies tested was determined using ProteOn as follows:

Nanobodies were captured either on serum albumin or via a FLAG3 tag using monoclonal anti-FLAG M2.

In case of binding of pre-existing antibodies on Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and HSA was injected at 10 µg/ml in ProteOn Acetate buffer pH4.5 (flow rate 100 µl/min) to render immobilization levels of approximately 3200 RU. After immobilization, surfaces were deactivated with ethanolamine HCl (flow rate 30 µl/min). Nanobodies were injected for 2 minutes at 45 µl/min over the HSA surface to render a Nanobody capture level of approximately 200 RU. The samples containing pre-existing antibodies were centrifuged for 2 minutes at 14,000 rpm and supernatant was diluted 1:10 in PBS-Tween20 (0.005%) before being injected for 2 minutes at 45 µl/min followed by a subsequent 400 seconds dissociation step. After each cycle (i.e. before a new Nanobody capture and blood sample injection step) the HSA surfaces were regenerated with a 2 minute injection of HCl (100 mM) at 45 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

In case of binding of pre-existing antibodies on FLAG-tagged Nanobodies captured on monoclonal anti-FLAG M2 (Sigma) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and anti-FLAG M2 mAb was injected at 10 µg/ml in ProteOn Acetate buffer pH4.5 (flow rate 100 µl/min) to render immobilization levels of approximately 4000 RU. After immobilization, surfaces were deactivated with ethanolamine HCl (flow rate 30 µl/min). Nanobodies were injected for 2 minutes at 45 µl/min over the anti-FLAG M2 surface to render a Nanobody capture level of approximately 100 RU. To reduce non-specific binding of the blood samples to the anti-FLAG M2 surface 100 nM 3×FLAG peptide (Sigma) was added to the blood samples. The samples containing pre-existing antibodies were centrifuged for 2 minutes at 14,000 rpm and supernatant was diluted 1:10 in PBS-Tween20 (0.005%) before being injected for 2 minutes at 45 µl/min followed by a subsequent 600 seconds dissociation step. After each cycle (i.e. before a new Nanobody capture and blood sample injection step) the anti-FLAG M2 surfaces were regenerated with a 10 seconds injection of Glycine pH1.5 (10 mM) at 150 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-anti-FLAG M2 dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

Example 1: Introducing the Mutations of the Invention in Reference A (SEQ ID NO: 1) Leads to a Reduction in Binding by Pre-Existing Antibodies Reference A (SEQ ID NO: 1) and two representative examples of the improved variants of Reference A carrying a C-terminal alanine extension and representative mutations according to the invention ([Reference A (L11V, V89L)-A] and [Reference A (L11V, V89L, T110K)-A], both tested with an N-terminal HIS6-FLAG3 tag, see SEQ ID NO:71) were tested for binding by pre-existing antibodies that are present in the samples from 96 serum samples from healthy human volunteers. The compounds were captured using the FLAG-tag and binding was measured using ProteOn according to the protocol given in the preamble to this Experimental Part.

The results are shown in FIG. 5. FIG. 6 lists the results for each of the samples that forms one of the data points in FIG. 5.

It can be seen that for most of the 96 samples tested, introducing the mutations according to the invention leads to a reduction in pre-existing antibody binding, with the degree of reduction generally being dependent on the level to which the pre-existing antibodies in each sample were capable of binding to Reference A.

Example 2: Introducing the Mutations of the Invention in Reference B (SEQ ID NO: 8) Leads to a Reduction in Binding by Pre-Existing Antibodies Reference B (SEQ ID NO: 8) and two representative examples of the improved variants of Reference A carrying a C-terminal alanine extension and representative mutations according to the invention ([Reference B (L11V, V89L)-A] and [Reference B (L11V, V89L,T110K)-A], both tested with an N-terminal HIS6-FLAG3 tag, see SEQ ID NO:71) were tested for binding by pre-existing antibodies that are present in the samples from 96 serum samples from healthy human volunteers. The compounds were captured using the FLAG-tag and binding was measured using ProteOn according to the protocol given in the preamble to this Experimental Part.

The results are shown in FIG. 7. FIG. 8 lists the results for each of the samples that forms one of the data points in FIG. 7.

It can be seen that for most of the 96 samples tested, introducing the mutations according to the invention leads to a reduction in pre-existing antibody binding, with the degree of reduction generally being dependent on the level to which the pre-existing antibodies in each sample were capable of binding to Reference A.

Example 3: Further Sequence Optimization of 1c81

In the process of sequence optimisation it is attempted to (1) knock out sites for post-translational modifications (PTM); (2) humanize the parental Nanobody; as well as (3) knock out epitopes for potential pre-existing antibodies. On the same time the functional and biophysical characteristics of the Nanobodies should preferably be preserved or even ameliorated.

Epitopes for potential pre-existing antibodies have been identified and eliminated in Example 2. In this example, sites for humanization and potential PTM were identified and elaborated.

In particular, for humanisation, the ISVD sequence is made more homologous to the human IGHV3-IGHJ germline consensus sequence. With the exception of the VHH "hallmark" residues, specific amino acids in the framework regions that differ between the ISVD and the human IGHV3-IGHJ germline consensus sequence were altered to the human counterpart in such a way that the protein structure, activity and stability were kept intact. For this all possible permutations of 1c81 were elaborated in view of the human IGHV3-IGHJ germline consensus sequence.

In the process of further sequence optimization the amino acid residues particularly considered were: 10G, 14P, 45R, 72D, 74S, 75K, 77T, 82M, 83R, and 108L.

3.1 Stability

As a first assessment the solubility of the SO variants produced as tagless proteins in *Escherichia coli* were assessed, in particular the stability during various steps of the purification process were elaborated, (e.g. after concentration, freeze/thawing), by visual inspection and by measuring aggregation at OD340 nm according to standard spectrophotometric methods. An OD340 nm with values >0.1 indicate possible aggregation.

Nanobodies were purified by affinity chromatography and reconstituted in Dulbecco's PBS. Samples with concentrations below 5 mg/mL were concentrated using VivaSpin columns (MWCO 5000, PES). Nanobody F024500044 (WT) showed protein loss and precipitation. Samples were filtered using Low binding Durapore 0.22 μm PVDF membrane (MilliPore). Concentrations of the filtered samples were measured using the Trinean Dropsense. Samples were stored at −20° C., and thawed followed by a centrifugation step and re-measurement of the protein concentration to assess freeze/thaw sensitivity.

The results are depicted in the Table 3.1

TABLE 3.1

| Nanobody ID | Yield (mg/L) | Conc. after purification (mg/ml) | A340 after purification | % Nb loss during desalting* | A340 after desalting | % Nb loss after FT | Conclusion on stability and yield |
|---|---|---|---|---|---|---|---|
| F024500044 (wt) | nd** | 5.6 | 6.19 | 89 | 0.15 | 37 | very high OD340 + serious precipitation (90%) during purification + Freeze/Thaw sensitivity |
| F024500045 | 3.5 | 6.0 | 0.08 | 27 | 0.02 | 0 | OK |
| F024500046 | 3.8 | 5.9 | 0.08 | 28 | 0.06 | 0 | OK |
| F024500047 | 3.8 | 5.9 | 0.29 | 27 | 0.02 | 1 | OK -> slightly elevated OD340 after purification, |
| F024500048 | 3.3 | 5.4 | 0.16 | 28 | 0.21 | 2 | OK -> slightly elevated OD340 after purification and desalting |
| F024500049 | 2.1 | 5.5 | 0.07 | 29 | 0.03 | 0 | OK, but decreased expression level (~50%) |

TABLE 3.1-continued

| Nanobody ID | Yield (mg/L) | Conc. after purification (mg/ml) | A340 after purification | % Nb loss during desalting* | A340 after desalting | % Nb loss after FT | Conclusion on stability and yield |
|---|---|---|---|---|---|---|---|
| F024500050 | 3.7 | 5.9 | 0.07 | 26 | 0.02 | 1 | OK |
| F024500051 | 4.1 | 6.6 | 0.31 | 23 | 0.03 | 25 | slightly elevated OD340 after purification + Freeze/Thaw sensitivity |

It was concluded that all variants showed improved solubility compared to wildtype 1c81. For two variants, however, some aggregation was observed resulting in a minor loss of protein.

3.2 Functionality

Next the functionality of the SO variants was assessed in comparison to the wild type 1c81. In particular, the inhibition of ATP-mediated $Ca^{2+}$ influx was assessed in mP2X7-HEK cells, essentially according to the methods described WO2013/178783.

Briefly, gating of P2X7 was monitored by real time flow cytometry on a FACS-CantoII (BD) equipped with an infrared lamp to maintain a constant temperature of 37° C. HEK293-hP2X7 cells were loaded with 2 μM Fluo-4 calcium indicator (Invitrogen) for 20 minutes at 37° C., and washed two times. Pelleted cells were resuspended in PBS supplemented with $Ca^{2+}$, $Mg^{2+}$ and 0.1% BSA, in the presence or absence of monovalent purified Nanobodies (10 nM or 100 nM). Cells were kept on ice and adjusted to 37° C. in a water bath for 1 min before analysis. ATP (Sigma-Aldrich) was added to a final concentration of 5 mM, and the mean fluorescence intensity of Fluo-4 uptake in cells was recorded for 30 minutes.

The results are depicted in FIG. 9, which shows inhibition of ATP-mediated calcium uptake of anti-P2X7 1c81 SO variants in Hek-mP2X7 cells. Panel A: Calcium uptake measured directly after ATP addition of variants at 100 nM and 10 nM concentrations. Panel B: Calcium uptake recorded over time of variants tested at 100 nM concentration.

From the results it can be concluded that two SO variants (#45 and #50) maintain full affinity and functionality in blocking P2X7, similar to wild type 1c81 (#44), while the binding affinity of the other variants varies, since they appear to not completely block ATP-mediated calcium influx over the timeframe of 30 minutes in this assay.

3.3 Stability Testing

Variant F024500050 (#50) was subjected to further stability testing. In particular, #50 was subjected to forced oxidation and temperature stress.

For testing temperature stress, the samples were subjected to 4 weeks storage at elevated temperatures, i.e. 25° C. and 40° C., after which the samples were analyzed using intact mass LC-MS and/or peptide map LC-MS (Agilent 1290 Infinity UHPLC system and Agilent Q-TOF Mass spectrometer). The results were compared to the reference material which was stored at −20° C.

For testing chemical stability, the sample was subjected to forced oxidation by $H_2O_2$ (10 mM final concentration) for 3 h in the dark. Thereafter the reaction was quenched by methionine (112 mM final concentration) for 1 h at room temperature. The samples were analyzed as set out above for testing temperature samples.

In the forced oxidation setting, the samples did not demonstrate any Methionine oxidation (data not shown).

The results from the intact mass LC-MS analysis of the control and 40° C. temperature stressed samples at 4 weeks storage are summarized in Table 3.3.

TABLE 3.3

Overview of the peaks observed in the intact mass LC-MS analysis of F02450050 control and 40° C. temperature stressed sample: 4 weeks storage

| peak | Mass (Da) | Identification | % Area ref | % Area 4 w 40° C. |
|---|---|---|---|---|
| 1 | 14488.92 | Intact mass + 17.84 Da possible oxidation | 0.8 | 3.7 |
| 2 | 14471.08 | Intact mass | 96.0 | 71.4 |
| 3 | 14471.05 | intact mass possible isomerization | 2.4 | 3.7 |
| 4 | 14453.06 | pyroglutamate | 0.8 | 21.2 |

In conclusion, under the forced oxidation conditions, no M oxidation was observed. Under the temperature stress conditions applied, mainly pyroglutamate formation was observed by intact mass analysis. Also by tryptic peptide map analysis, mainly pyroglutamate formation was observed. In addition, a small, negligible amount of isomerization and deamidation were observed.

Mutating E1D in #50 virtually abolished pyroglutamate formation (data not shown). Hence, a preferred mutation would be E1D (cf. SEQ ID NO:s 147-153 and 162-168).

3.4 Conclusion

It can be seen that variant F024500050 is particularly preferred since it shows improved stability at higher protein concentrations while retaining functionality. This variant F024500050 can be combined with the mutations of the invention that lead to a reduction in binding by pre-existing antibodies (cf. Example 2). Preferred mutations are L11V, V89L, T110K, Q108L and/or 114A, as well as E1D and/or N-terminal Alanine preferably all of these mutations.

Example 4: Further Sequence Optimization of 3c23

Similar to Example 3, the sequence of 3c23 was analysed for sequence optimization. In Example 2, epitopes for potential pre-existing antibodies were identified and eliminated.

In this example, sites for humanization and potential PTM were identified and further elaborated.

4.1 Stability Testing

Similar to Example 3.3, variant F024500016 (#16; SEQ ID NO: 87) was subjected to further stability testing. In particular, #16 was subjected to forced oxidation and temperature stress.

For testing temperature stress, the samples were subjected to 4 weeks storage at elevated temperatures, i.e. 25° C. and 40° C., after which the samples were analyzed using intact mass LC-MS and/or peptide map LC-MS (Agilent 1290

Infinity UHPLC system and Agilent Q-TOF Mass spectrometer). The results were compared to the reference material which was stored at −20° C.

For testing chemical stability, the sample was subjected to forced oxidation by $H_2O_2$ (10 mM final concentration) for 3 h in the dark. Thereafter the reaction was quenched by methionine (112 mM final concentration) for 1 h at room temperature. The samples were analyzed as set out above for testing temperature samples.

The intact mass chromatograms of the F024500016 control and forced oxidation sample are given in FIG. 10. Only a very small increase in pre peak region was observed, indicating that no methionines susceptible for oxidation are present in this nanobody.

The intact mass chromatograms of the F024500016 control and temperature stressed samples are given in FIG. 11.

Upon temperature stress, mainly pyroglutamate formation was observed. Only very small amounts of oxidation, deamidation and intact +12 Da were seen.

Based on these results E1D is a preferred mutation (see e.g. SEQ ID NO:s 154 to 161 and 169 to 176).

4.2 Humanisation

For humanisation, the ISVD sequence is made more homologous to the human IGHV3-IGHJ germline consensus sequence. With the exception of the VHH "hallmark" residues, specific amino acids in the framework regions that differ between the ISVD and the human IGHV3-IGHJ germline consensus sequence were altered to the human counterpart in such a way that the protein structure, activity and stability were kept intact. For this all possible permutations of 3c23 were elaborated in view of the human IGHV3-IGHJ germline consensus sequence.

In the process of further sequence optimization the amino acid residues particularly considered were: 14P, 60A, 73N, 74S, 79Y, and 83R. Various permutations are represented by SEQ ID NO:s 136-143 (and based on the results of Example 4.1 SEQ ID NO:s 154 to 161 and 169 to 176 comprising E1D).

Similar to Examples 3.1 and 3.2 the stability and the functionality of these variants can be tested.

After selecting a particularly preferred sequence variant, which would show stability and functionality, this variant can be combined with the mutations of the invention that lead to a reduction in binding by pre-existing antibodies (cf. Example 1). Preferred mutations are L11V, V89L, T110K, Q108L and/or 114A, as well as E1D and/or N-terminal Alanine, preferably all of these mutations.

The entire contents of all of the references (including literature references, issued patents, published patent applications, and co-pending patent applications) cited throughout this application are hereby expressly incorporated by reference, in particular for the teaching that is referenced hereinabove.

The invention claimed is:

1. An immunoglobulin single variable domain that binds to the P2X7 receptor comprising the structure of FR1-CDR1-FR2-CDR2-FR3-CDR3-FR4; wherein FR1 to FR4 refer to framework regions (FRs) 1 to 4 of the immunoglobulin single variable domain; wherein CDR1 to CDR3 refer to complementary determining regions (CDRs) 1 to 3 of the immunoglobulin single variable domain; and wherein the immunoglobulin single variable domain has:
 a CDR1 chosen from the group consisting of SEQ ID NO: 2 and amino acid sequences that have 1 amino acid difference with (SEQ ID NO:2; and
 a CDR2 chosen from the group consisting of SEQ ID NO: 3 and amino acid sequences that have 1 or 2 amino acid differences with SEQ ID NO:3; and
 a CDR3 chosen from the group consisting of SEQ ID NO: 4 and amino acid sequences that have 1 or 2 amino acid differences with SEQ ID NO:4;
and has:
 FRs that cumulatively have a degree of sequence identity of at least 85% with the FRs of SEQ ID NO:1;
and/or has:
 FRs that cumulatively have no more than 11 amino acid differences with the FRs of SEQ ID NO:1.

2. A polypeptide comprising the immunoglobulin single variable domain according to claim 1.

3. The polypeptide of claim 2, further comprising a second immunoglobulin single variable domain, wherein the second immunoglobulin single variable domain comprises the structure of FR1-CDR1-FR2-CDR2-FR3-CDR3-FR4 and has:

a CDR1 chosen from the group consisting of SEQ ID NO: 9 and amino acid sequences that have 1 amino acid difference with SEQ ID NO:9; and a CDR2 chosen from the group consisting of SEQ ID NO: 10 and amino acid sequences that have 1 or 2 amino acid differences with SEQ ID NO:10; and a CDR3 chosen from the group consisting of SEQ ID NO: 11 and amino acid sequences that have 1 or 2 amino acid differences with SEQ ID NO:11;

and has:

FRs that cumulatively have a degree of sequence identity of at least 85% with the FRs of SEQ ID NO:8;

and/or has:

FRs that cumulatively have no more than 11 amino acid differences with the FRs of SEQ ID NO:8.

4. The polypeptide of claim 3, wherein the second immunoglobulin domain comprises an E1D mutation compared to SEQ ID NO: 8.

5. The immunoglobulin single variable domain of claim 1, comprising an E1D mutation compared to SEQ ID NO: 1.

6. An immunoglobulin single variable domain that binds to the P2X7 receptor comprising the structure of FR1-CDR1-FR2-CDR2-FR3-CDR3-FR4; wherein FR1 to FR4 refer to framework regions (FRs) 1 to 4 of the immunoglobulin single variable domain; wherein CDR1 to CDR3 refer to complementary determining regions (CDRs) 1 to 3 of the immunoglobulin single variable domain; and wherein the immunoglobulin single variable domain has:

a CDR1 chosen from the group consisting of SEQ ID NO: 9 and amino acid sequences that have 1 amino acid difference with SEQ ID NO:9; and a CDR2 chosen from the group consisting of SEQ ID NO: 10 and amino acid sequences that have 1 or 2 amino acid differences with SEQ ID NO:10; and a CDR3 chosen from the group consisting of SEQ ID NO: 11 and amino acid sequences that have 1 or 2 amino acid differences with SEQ ID NO:11;

and has:

FRs that cumulatively have a degree of sequence identity of at least 85% with the FRs of SEQ ID NO:8;

and/or has:

FRs that cumulatively have no more than 11 amino acid differences with the FRs of SEQ ID NO:8.

7. A polypeptide comprising the immunoglobulin single variable domain according to claim 6.

8. The immunoglobulin single variable domain of claim 6, comprising an E1D mutation compared to SEQ ID NO: 8.

* * * * *

SEQUENCE LISTING

```
<160> NUMBER OF SEQ ID NOS: 177

<210> SEQ ID NO 1
<211> LENGTH: 129
<212> TYPE: PRT
<213> ORGANISM: Artificial Sequence
<220> FEATURE:
<223> OTHER INFORMATION: CDR Sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 2
<211> LENGTH: 5
<212> TYPE: PRT
<213> ORGANISM: Artificial Sequence
<220> FEATURE:
<223> OTHER INFORMATION: CDR Sequence
```

<400> SEQUENCE: 2

His Tyr Ala Met Gly
1               5

<210> SEQ ID NO 3
<211> LENGTH: 16
<212> TYPE: PRT
<213> ORGANISM: Artificial Sequence
<220> FEATURE:
<223> OTHER INFORMATION: CDR Sequence

<400> SEQUENCE: 3

Ala Ile Ser Ser Tyr Gly Ser Thr Asp Tyr Gly Asp Ser Val Lys Gly
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: CDR Sequence

<400> SEQUENCE: 4

Ala Asp Glu Thr Leu Gly Ala Val Pro Asn Phe Arg Leu His Glu Lys
1               5                   10                  15

Tyr Glu Tyr Glu Tyr
            20

<210> SEQ ID NO 5
<211> LENGTH: 10
<212> TYPE: PRT
<213> ORGANISM: Artificial Sequence
<220> FEATURE:
<223> OTHER INFORMATION: CDR Sequence

<400> SEQUENCE: 5

Gly Arg Thr Phe Arg His Tyr Ala Met Gly
1               5                   10

<210> SEQ ID NO 6
<211> LENGTH: 9
<212> TYPE: PRT
<213> ORGANISM: Artificial Sequence
<220> FEATURE:
<223> OTHER INFORMATION: CDR Sequence

<400> SEQUENCE: 6

Ala Ile Ser Ser Tyr Gly Ser Thr Asp
1               5

<210> SEQ ID NO 7
<211> LENGTH: 21
<212> TYPE: PRT
<213> ORGANISM: Artificial Sequence
<220> FEATURE:
<223> OTHER INFORMATION: CDR Sequence

<400> SEQUENCE: 7

Ala Asp Glu Thr Leu Gly Ala Val Pro Asn Phe Arg Leu His Glu Lys
1               5                   10                  15

Tyr Glu Tyr Glu Tyr
            20

<210> SEQ ID NO 8

<211> LENGTH: 130
<212> TYPE: PRT
<213> ORGANISM: Artificial Sequence
<220> FEATURE:
<223> OTHER INFORMATION: CDR Sequence

<400> SEQUENCE: 8

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Ser Ser
    130

<210> SEQ ID NO 9
<211> LENGTH: 7
<212> TYPE: PRT
<213> ORGANISM: Artificial Sequence
<220> FEATURE:
<223> OTHER INFORMATION: CDR Sequence

<400> SEQUENCE: 9

Phe Ser Thr Ser Thr Met Gly
1               5

<210> SEQ ID NO 10
<211> LENGTH: 17
<212> TYPE: PRT
<213> ORGANISM: Artificial Sequence
<220> FEATURE:
<223> OTHER INFORMATION: CDR Sequence

<400> SEQUENCE: 10

Ala Ile Asp Trp Ser Asp Phe Asn Thr Tyr Tyr Ala Asp Ser Val Lys
1               5                   10                  15

Gly

<210> SEQ ID NO 11
<211> LENGTH: 19
<212> TYPE: PRT
<213> ORGANISM: Artificial Sequence
<220> FEATURE:
<223> OTHER INFORMATION: CDR Sequence

<400> SEQUENCE: 11

His Ser Glu Thr Arg Gly Gly Thr Arg Tyr Phe Asp Arg Pro Ser Leu
1               5                   10                  15

Tyr Asn Tyr

```
<210> SEQ ID NO 12
<211> LENGTH: 12
<212> TYPE: PRT
<213> ORGANISM: Artificial Sequence
<220> FEATURE:
<223> OTHER INFORMATION: CDR Sequence

<400> SEQUENCE: 12

Gly Arg Thr Phe Ser Phe Ser Thr Ser Thr Met Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR Sequence

<400> SEQUENCE: 13

Ala Ile Asp Trp Ser Asp Phe Asn Thr Tyr
1               5                   10

<210> SEQ ID NO 14
<211> LENGTH: 19
<212> TYPE: PRT
<213> ORGANISM: Artificial Sequence
<220> FEATURE:
<223> OTHER INFORMATION: CDR Sequence

<400> SEQUENCE: 14

His Ser Glu Thr Arg Gly Gly Thr Arg Tyr Phe Asp Arg Pro Ser Leu
1               5                   10                  15

Tyr Asn Tyr

<210> SEQ ID NO 15
<211> LENGTH: 129
<212> TYPE: PRT
<213> ORGANISM: Artificial Sequence
<220> FEATURE:
<223> OTHER INFORMATION: CDR Sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Thr Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 16
<211> LENGTH: 129
```

<212> TYPE: PRT
<213> ORGANISM: Artificial Sequence
<220> FEATURE:
<223> OTHER INFORMATION: CDR Sequence

<400> SEQUENCE: 16

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: CDR Sequence

<400> SEQUENCE: 17

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Gln Val Ser
        115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: CDR Sequence

<400> SEQUENCE: 18

```
Glu Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65              70                  75                  80

Gln Met Asn Ser Leu Lys Pro Glu Asp Thr Ala Val Tyr Tyr Cys Ala
            85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
            115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: CDR Sequence

<400> SEQUENCE: 19

Glu Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65              70                  75                  80

Gln Met Asn Ser Leu Lys Pro Glu Asp Thr Ala Val Tyr Tyr Cys Ala
            85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Gln
            115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: CDR Sequence

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
```

```
                35                  40                  45
Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Lys Val Ser
                115                 120                 125

Ser

<210> SEQ ID NO 21
<211> LENGTH: 129
<212> TYPE: PRT
<213> ORGANISM: Artificial Sequence
<220> FEATURE:
<223> OTHER INFORMATION: CDR Sequence

<400> SEQUENCE: 21

Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
                35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Gln Val Ser
                115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: CDR Sequence

<400> SEQUENCE: 22

Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
                35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
 65                  70                  75                  80
```

```
Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
        115                 120                 125

Ser
```

<210> SEQ ID NO 23
<211> LENGTH: 129
<212> TYPE: PRT
<213> ORGANISM: Artificial Sequence
<220> FEATURE:
<223> OTHER INFORMATION: CDR Sequence

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Gln
        115                 120                 125

Ser
```

<210> SEQ ID NO 24
<211> LENGTH: 129
<212> TYPE: PRT
<213> ORGANISM: Artificial Sequence
<220> FEATURE:
<223> OTHER INFORMATION: CDR Sequence

<400> SEQUENCE: 24

```
Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110
```

Lys Tyr Glu Tyr Glu Tyr Trp Gly Gln Gly Thr Leu Val Thr Val Ser
                115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: CDR Sequence

<400> SEQUENCE: 25

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
                115                 120                 125

Ser

<210> SEQ ID NO 26
<211> LENGTH: 129
<212> TYPE: PRT
<213> ORGANISM: Artificial Sequence
<220> FEATURE:
<223> OTHER INFORMATION: CDR Sequence

<400> SEQUENCE: 26

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Gln Val Ser
                115                 120                 125

Ser

<210> SEQ ID NO 27

```
<211> LENGTH: 129
<212> TYPE: PRT
<213> ORGANISM: Artificial Sequence
<220> FEATURE:
<223> OTHER INFORMATION: CDR Sequence

<400> SEQUENCE: 27

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
        115                 120                 125

Ser

<210> SEQ ID NO 28
<211> LENGTH: 129
<212> TYPE: PRT
<213> ORGANISM: Artificial Sequence
<220> FEATURE:
<223> OTHER INFORMATION: CDR Sequence

<400> SEQUENCE: 28

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Gln
        115                 120                 125

Ser

<210> SEQ ID NO 29
<211> LENGTH: 130
<212> TYPE: PRT
<213> ORGANISM: Artificial Sequence
<220> FEATURE:
<223> OTHER INFORMATION: CDR Sequence

<400> SEQUENCE: 29
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Thr Tyr Tyr Cys Ala
            85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Ala
    130

<210> SEQ ID NO 30
<211> LENGTH: 130
<212> TYPE: PRT
<213> ORGANISM: Artificial Sequence
<220> FEATURE:
<223> OTHER INFORMATION: CDR Sequence

<400> SEQUENCE: 30

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
            85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
            115                 120                 125

Ser Ala
    130

<210> SEQ ID NO 31
<211> LENGTH: 130
<212> TYPE: PRT
<213> ORGANISM: Artificial Sequence
<220> FEATURE:
<223> OTHER INFORMATION: CDR Sequence

<400> SEQUENCE: 31

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
```

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Gln Val Ser
        115                 120                 125

Ser Ala
    130

<210> SEQ ID NO 32
<211> LENGTH: 130
<212> TYPE: PRT
<213> ORGANISM: Artificial Sequence
<220> FEATURE:
<223> OTHER INFORMATION: CDR Sequence

<400> SEQUENCE: 32

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
        115                 120                 125

Ser Ala
    130

<210> SEQ ID NO 33
<211> LENGTH: 130
<212> TYPE: PRT
<213> ORGANISM: Artificial Sequence
<220> FEATURE:
<223> OTHER INFORMATION: CDR Sequence

<400> SEQUENCE: 33

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

```
Ala Ala Ile Ser Ser Tyr Gly Ser Thr Asp Tyr Gly Asp Ser Val Lys
         50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Val Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Gln
            115                 120                 125

Ser Ala
    130

<210> SEQ ID NO 34
<211> LENGTH: 130
<212> TYPE: PRT
<213> ORGANISM: Artificial Sequence
<220> FEATURE:
<223> OTHER INFORMATION: CDR Sequence

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
         50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Leu Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
            115                 120                 125

Ser Ala
    130

<210> SEQ ID NO 35
<211> LENGTH: 130
<212> TYPE: PRT
<213> ORGANISM: Artificial Sequence
<220> FEATURE:
<223> OTHER INFORMATION: CDR Sequence

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
         50                  55                  60

Gly Arg Phe Thr Ile Ser Arg Asp Asp Ala Lys Asn Thr Val Pro Leu
 65                  70                  75                  80
```

```
Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Gln Val Ser
        115                 120                 125

Ser Ala
    130

<210> SEQ ID NO 36
<211> LENGTH: 130
<212> TYPE: PRT
<213> ORGANISM: Artificial Sequence
<220> FEATURE:
<223> OTHER INFORMATION: CDR Sequence

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
        115                 120                 125

Ser Ala
    130

<210> SEQ ID NO 37
<211> LENGTH: 130
<212> TYPE: PRT
<213> ORGANISM: Artificial Sequence
<220> FEATURE:
<223> OTHER INFORMATION: CDR Sequence

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
```

```
                100             105             110
Lys Tyr Glu Tyr Glu Tyr Trp Gly Gln Gly Thr Leu Val Thr Val Gln
            115             120             125

Ser Ala
    130

<210> SEQ ID NO 38
<211> LENGTH: 130
<212> TYPE: PRT
<213> ORGANISM: Artificial Sequence
<220> FEATURE:
<223> OTHER INFORMATION: CDR Sequence

<400> SEQUENCE: 38

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Ala
    130

<210> SEQ ID NO 39
<211> LENGTH: 130
<212> TYPE: PRT
<213> ORGANISM: Artificial Sequence
<220> FEATURE:
<223> OTHER INFORMATION: CDR Sequence

<400> SEQUENCE: 39

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125
```

Ser Ala
    130

<210> SEQ ID NO 40
<211> LENGTH: 130
<212> TYPE: PRT
<213> ORGANISM: Artificial Sequence
<220> FEATURE:
<223> OTHER INFORMATION: CDR Sequence

<400> SEQUENCE: 40

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Gln Val Ser
        115                 120                 125

Ser Ala
    130

<210> SEQ ID NO 41
<211> LENGTH: 130
<212> TYPE: PRT
<213> ORGANISM: Artificial Sequence
<220> FEATURE:
<223> OTHER INFORMATION: CDR Sequence

<400> SEQUENCE: 41

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Lys
        115                 120                 125

Ser Ala
    130

<210> SEQ ID NO 42

<211> LENGTH: 130
<212> TYPE: PRT
<213> ORGANISM: Artificial Sequence
<220> FEATURE:
<223> OTHER INFORMATION: CDR Sequence

<400> SEQUENCE: 42

Glu Val Gln Leu Val Glu Ser Gly Gly Gly Val Val Gln Pro Gly Gly
1               5                   10                  15
Ser Leu Arg Leu Ser Cys Ala Ala Ser Gly Arg Thr Phe Arg His Tyr
            20                  25                  30
Ala Met Gly Trp Phe Arg Gln Ala Pro Gly Lys Glu Arg Glu Phe Val
        35                  40                  45
Ala Ala Ile Ser Ser Tyr Gly Ser Thr Asp Tyr Gly Asp Ser Val Lys
    50                  55                  60
Gly Arg Phe Thr Ile Ser Arg Asp Asp Ala Lys Asn Thr Val Pro Leu
65                  70                  75                  80
Gln Met Asn Ser Leu Lys Pro Glu Asp Thr Ala Leu Tyr Tyr Cys Ala
                85                  90                  95
Ala Ala Asp Glu Thr Leu Gly Ala Val Pro Asn Phe Arg Leu His Glu
            100                 105                 110
Lys Tyr Glu Tyr Glu Tyr Trp Gly Gln Gly Thr Leu Val Thr Val Gln
        115                 120                 125
Ser Ala
    130

<210> SEQ ID NO 43
<211> LENGTH: 130
<212> TYPE: PRT
<213> ORGANISM: Artificial Sequence
<220> FEATURE:
<223> OTHER INFORMATION: CDR Sequence

<400> SEQUENCE: 43

Glu Val Gln Leu Val Glu Ser Gly Gly Lys Leu Val Gln Pro Gly Gly
1               5                   10                  15
Ser Leu Arg Leu Ser Cys Ser Ala Ser Gly Arg Thr Phe Ser Phe Ser
            20                  25                  30
Thr Ser Thr Met Gly Trp Phe Arg Gln Ala Pro Gly Lys Glu Leu Glu
        35                  40                  45
Phe Val Ala Ala Ile Asp Trp Ser Asp Phe Asn Thr Tyr Tyr Ala Asp
    50                  55                  60
Ser Val Lys Gly Arg Phe Thr Ile Ser Arg His Asn Pro Arg Asn Ser
65                  70                  75                  80
Val Tyr Leu Gln Leu Asn Ser Leu Lys Pro Glu Asp Thr Ala Thr Tyr
                85                  90                  95
Tyr Cys Ala Ala His Ser Glu Thr Arg Gly Thr Arg Tyr Phe Asp
            100                 105                 110
Arg Pro Ser Leu Tyr Asn Tyr Trp Gly Gln Gly Thr Leu Val Thr Val
        115                 120                 125
Ser Ser
    130

<210> SEQ ID NO 44
<211> LENGTH: 130
<212> TYPE: PRT
<213> ORGANISM: Artificial Sequence
<220> FEATURE:
<223> OTHER INFORMATION: CDR Sequence

```
<400> SEQUENCE: 44

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Leu Val Lys Val
            115                 120                 125

Ser Ser
    130

<210> SEQ ID NO 45
<211> LENGTH: 130
<212> TYPE: PRT
<213> ORGANISM: Artificial Sequence
<220> FEATURE:
<223> OTHER INFORMATION: CDR Sequence

<400> SEQUENCE: 45

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Gln Val
            115                 120                 125

Ser Ser
    130

<210> SEQ ID NO 46
<211> LENGTH: 130
<212> TYPE: PRT
<213> ORGANISM: Artificial Sequence
<220> FEATURE:
<223> OTHER INFORMATION: CDR Sequence

<400> SEQUENCE: 46

Glu Val Gln Leu Val Glu Ser Gly Gly Lys Val Val Gln Pro Gly Gly
1               5                   10                  15
```

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
 50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
                    100                 105                 110

Arg Pro Ser Leu Tyr Asn Tyr Trp Gly Gln Gly Thr Leu Val Thr Val
            115                 120                 125

Lys Ser
    130

<210> SEQ ID NO 47
<211> LENGTH: 130
<212> TYPE: PRT
<213> ORGANISM: Artificial Sequence
<220> FEATURE:
<223> OTHER INFORMATION: CDR Sequence

<400> SEQUENCE: 47

Glu Val Gln Leu Val Glu Ser Gly Gly Lys Val Val Gln Pro Gly Gly
 1               5                  10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
 50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
                    100                 105                 110

Arg Pro Ser Leu Tyr Asn Tyr Trp Gly Gln Gly Thr Leu Val Thr Val
            115                 120                 125

Gln Ser
    130

<210> SEQ ID NO 48
<211> LENGTH: 130
<212> TYPE: PRT
<213> ORGANISM: Artificial Sequence
<220> FEATURE:
<223> OTHER INFORMATION: CDR Sequence

<400> SEQUENCE: 48

Glu Val Gln Leu Val Glu Ser Gly Gly Lys Leu Val Gln Pro Gly Gly
 1               5                  10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu

```
                35                  40                  45

Phe Val Ala Ala Ile Asp Trp Ser Asp Phe Asn Thr Tyr Tyr Ala Asp
     50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Lys Val
                115                 120                 125

Ser Ser
130

<210> SEQ ID NO 49
<211> LENGTH: 130
<212> TYPE: PRT
<213> ORGANISM: Artificial Sequence
<220> FEATURE:
<223> OTHER INFORMATION: CDR Sequence

<400> SEQUENCE: 49

Glu Val Gln Leu Val Glu Ser Gly Gly Lys Leu Val Gln Pro Gly Gly
 1               5                  10                  15

Ser Leu Arg Leu Ser Cys Ser Ala Ser Gly Arg Thr Phe Ser Phe Ser
                 20                  25                  30

Thr Ser Thr Met Gly Trp Phe Arg Gln Ala Pro Gly Lys Glu Leu Glu
                 35                  40                  45

Phe Val Ala Ala Ile Asp Trp Ser Asp Phe Asn Thr Tyr Tyr Ala Asp
     50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Gln Val
                115                 120                 125

Ser Ser
130

<210> SEQ ID NO 50
<211> LENGTH: 130
<212> TYPE: PRT
<213> ORGANISM: Artificial Sequence
<220> FEATURE:
<223> OTHER INFORMATION: CDR Sequence

<400> SEQUENCE: 50

Glu Val Gln Leu Val Glu Ser Gly Gly Lys Leu Val Gln Pro Gly Gly
 1               5                  10                  15

Ser Leu Arg Leu Ser Cys Ser Ala Ser Gly Arg Thr Phe Ser Phe Ser
                 20                  25                  30

Thr Ser Thr Met Gly Trp Phe Arg Gln Ala Pro Gly Lys Glu Leu Glu
                 35                  40                  45

Phe Val Ala Ala Ile Asp Trp Ser Asp Phe Asn Thr Tyr Tyr Ala Asp
     50                  55                  60
```

```
Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Lys Ser
    130

<210> SEQ ID NO 51
<211> LENGTH: 130
<212> TYPE: PRT
<213> ORGANISM: Artificial Sequence
<220> FEATURE:
<223> OTHER INFORMATION: CDR Sequence

<400> SEQUENCE: 51

Glu Val Gln Leu Val Glu Ser Gly Gly Lys Leu Val Gln Pro Gly Gly
 1               5                  10                  15

Ser Leu Arg Leu Ser Cys Ser Ala Ser Gly Arg Thr Phe Ser Phe Ser
             20                  25                  30

Thr Ser Thr Met Gly Trp Phe Arg Gln Ala Pro Gly Lys Glu Leu Glu
         35                  40                  45

Phe Val Ala Ala Ile Asp Trp Ser Asp Phe Asn Thr Tyr Tyr Ala Asp
 50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Gln Ser
    130

<210> SEQ ID NO 52
<211> LENGTH: 130
<212> TYPE: PRT
<213> ORGANISM: Artificial Sequence
<220> FEATURE:
<223> OTHER INFORMATION: CDR Sequence

<400> SEQUENCE: 52

Glu Val Gln Leu Val Glu Ser Gly Gly Lys Val Val Gln Pro Gly Gly
 1               5                  10                  15

Ser Leu Arg Leu Ser Cys Ser Ala Ser Gly Arg Thr Phe Ser Phe Ser
             20                  25                  30

Thr Ser Thr Met Gly Trp Phe Arg Gln Ala Pro Gly Lys Glu Leu Glu
         35                  40                  45

Phe Val Ala Ala Ile Asp Trp Ser Asp Phe Asn Thr Tyr Tyr Ala Asp
 50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95
```

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Thr Val
            115                 120                 125

Ser Ser
    130

<210> SEQ ID NO 53
<211> LENGTH: 130
<212> TYPE: PRT
<213> ORGANISM: Artificial Sequence
<220> FEATURE:
<223> OTHER INFORMATION: CDR Sequence

<400> SEQUENCE: 53

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
            115                 120                 125

Ser Ser
    130

<210> SEQ ID NO 54
<211> LENGTH: 130
<212> TYPE: PRT
<213> ORGANISM: Artificial Sequence
<220> FEATURE:
<223> OTHER INFORMATION: CDR Sequence

<400> SEQUENCE: 54

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Gln Val

Ser Ser
    130

<210> SEQ ID NO 55
<211> LENGTH: 130
<212> TYPE: PRT
<213> ORGANISM: Artificial Sequence
<220> FEATURE:
<223> OTHER INFORMATION: CDR Sequence

<400> SEQUENCE: 55

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Lys Ser
    130

<210> SEQ ID NO 56
<211> LENGTH: 130
<212> TYPE: PRT
<213> ORGANISM: Artificial Sequence
<220> FEATURE:
<223> OTHER INFORMATION: CDR Sequence

<400> SEQUENCE: 56

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Gln Ser
    130

-continued

<210> SEQ ID NO 57
<211> LENGTH: 131
<212> TYPE: PRT
<213> ORGANISM: Artificial Sequence
<220> FEATURE:
<223> OTHER INFORMATION: CDR Sequence

<400> SEQUENCE: 57

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Thr Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Ser Ser Ala
        130

<210> SEQ ID NO 58
<211> LENGTH: 131
<212> TYPE: PRT
<213> ORGANISM: Artificial Sequence
<220> FEATURE:
<223> OTHER INFORMATION: CDR Sequence

<400> SEQUENCE: 58

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Ala
        130

<210> SEQ ID NO 59
<211> LENGTH: 131
<212> TYPE: PRT
<213> ORGANISM: Artificial Sequence -continued
<220> FEATURE:
<223> OTHER INFORMATION: CDR Sequence

<400> SEQUENCE: 59

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Gln Val
        115                 120                 125

Ser Ser Ala
    130

<210> SEQ ID NO 60
<211> LENGTH: 131
<212> TYPE: PRT
<213> ORGANISM: Artificial Sequence
<220> FEATURE:
<223> OTHER INFORMATION: CDR Sequence

<400> SEQUENCE: 60

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Lys Ser Ala
    130

<210> SEQ ID NO 61
<211> LENGTH: 131
<212> TYPE: PRT
<213> ORGANISM: Artificial Sequence
<220> FEATURE:
<223> OTHER INFORMATION: CDR Sequence

<400> SEQUENCE: 61

```
Glu Val Gln Leu Val Glu Ser Gly Gly Lys Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
        50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Thr Val
            115                 120                 125

Gln Ser Ala
    130

<210> SEQ ID NO 62
<211> LENGTH: 131
<212> TYPE: PRT
<213> ORGANISM: Artificial Sequence
<220> FEATURE:
<223> OTHER INFORMATION: CDR Sequence

<400> SEQUENCE: 62

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
        50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Lys Val
            115                 120                 125

Ser Ser Ala
    130

<210> SEQ ID NO 63
<211> LENGTH: 131
<212> TYPE: PRT
<213> ORGANISM: Artificial Sequence
<220> FEATURE:
<223> OTHER INFORMATION: CDR Sequence

<400> SEQUENCE: 63

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30
```

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Gln Val
            115                 120                 125

Ser Ser Ala
    130

<210> SEQ ID NO 64
<211> LENGTH: 131
<212> TYPE: PRT
<213> ORGANISM: Artificial Sequence
<220> FEATURE:
<223> OTHER INFORMATION: CDR Sequence

<400> SEQUENCE: 64

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Thr Val
            115                 120                 125

Lys Ser Ala
    130

<210> SEQ ID NO 65
<211> LENGTH: 131
<212> TYPE: PRT
<213> ORGANISM: Artificial Sequence
<220> FEATURE:
<223> OTHER INFORMATION: CDR Sequence

<400> SEQUENCE: 65

Glu Val Gln Leu Val Glu Ser Gly Gly Lys Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp

```
                    50                  55                  60
Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                     85                  90                  95

Tyr Cys Ala Ala His Ser Glu Thr Arg Gly Gly Thr Arg Tyr Phe Asp
                    100                 105                 110

Arg Pro Ser Leu Tyr Asn Tyr Trp Gly Gln Gly Thr Leu Val Thr Val
                    115                 120                 125

Gln Ser Ala
        130

<210> SEQ ID NO 66
<211> LENGTH: 131
<212> TYPE: PRT
<213> ORGANISM: Artificial Sequence
<220> FEATURE:
<223> OTHER INFORMATION: CDR Sequence

<400> SEQUENCE: 66

Glu Val Gln Leu Val Glu Ser Gly Gly Lys Val Val Gln Pro Gly Gly
  1               5                  10                  15

Ser Leu Arg Leu Ser Cys Ser Ala Ser Gly Arg Thr Phe Ser Phe Ser
                 20                  25                  30

Thr Ser Thr Met Gly Trp Phe Arg Gln Ala Pro Gly Lys Glu Leu Glu
                 35                  40                  45

Phe Val Ala Ala Ile Asp Trp Ser Asp Phe Asn Thr Tyr Tyr Ala Asp
             50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                     85                  90                  95

Tyr Cys Ala Ala His Ser Glu Thr Arg Gly Gly Thr Arg Tyr Phe Asp
                    100                 105                 110

Arg Pro Ser Leu Tyr Asn Tyr Trp Gly Gln Gly Thr Leu Val Thr Val
                    115                 120                 125

Ser Ser Ala
        130

<210> SEQ ID NO 67
<211> LENGTH: 131
<212> TYPE: PRT
<213> ORGANISM: Artificial Sequence
<220> FEATURE:
<223> OTHER INFORMATION: CDR Sequence

<400> SEQUENCE: 67

Glu Val Gln Leu Val Glu Ser Gly Gly Lys Val Val Gln Pro Gly Gly
  1               5                  10                  15

Ser Leu Arg Leu Ser Cys Ser Ala Ser Gly Arg Thr Phe Ser Phe Ser
                 20                  25                  30

Thr Ser Thr Met Gly Trp Phe Arg Gln Ala Pro Gly Lys Glu Leu Glu
                 35                  40                  45

Phe Val Ala Ala Ile Asp Trp Ser Asp Phe Asn Thr Tyr Tyr Ala Asp
             50                  55                  60

Ser Val Lys Gly Arg Phe Thr Ile Ser Arg His Asn Pro Arg Asn Ser
 65                  70                  75                  80
```

```
Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Ala
    130

<210> SEQ ID NO 68
<211> LENGTH: 131
<212> TYPE: PRT
<213> ORGANISM: Artificial Sequence
<220> FEATURE:
<223> OTHER INFORMATION: CDR Sequence

<400> SEQUENCE: 68

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Gln Val
        115                 120                 125

Ser Ser Ala
    130

<210> SEQ ID NO 69
<211> LENGTH: 131
<212> TYPE: PRT
<213> ORGANISM: Artificial Sequence
<220> FEATURE:
<223> OTHER INFORMATION: CDR Sequence

<400> SEQUENCE: 69

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110
```

```
Arg Pro Ser Leu Tyr Asn Tyr Trp Gly Gln Gly Thr Leu Val Thr Val
        115                 120                 125

Lys Ser Ala
    130

<210> SEQ ID NO 70
<211> LENGTH: 131
<212> TYPE: PRT
<213> ORGANISM: Artificial Sequence
<220> FEATURE:
<223> OTHER INFORMATION: CDR Sequence

<400> SEQUENCE: 70

Glu Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Gln Ser Ala
    130

<210> SEQ ID NO 71
<211> LENGTH: 34
<212> TYPE: PRT
<213> ORGANISM: Artificial Sequence
<220> FEATURE:
<223> OTHER INFORMATION: HIS6-FLAG3 tag

<400> SEQUENCE: 71

His His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 72
<211> LENGTH: 5
<212> TYPE: PRT
<213> ORGANISM: Artificial Sequence
<220> FEATURE:
<223> OTHER INFORMATION: C-terminal end

<400> SEQUENCE: 72

Val Thr Val Lys Ser
1               5

<210> SEQ ID NO 73
<211> LENGTH: 5
<212> TYPE: PRT
```

```
<213> ORGANISM: Artificial Sequence
<220> FEATURE:
<223> OTHER INFORMATION: C-terminal end

<400> SEQUENCE: 73

Val Thr Val Gln Ser
1               5

<210> SEQ ID NO 74
<211> LENGTH: 5
<212> TYPE: PRT
<213> ORGANISM: Artificial Sequence
<220> FEATURE:
<223> OTHER INFORMATION: C-terminal end

<400> SEQUENCE: 74

Val Lys Val Ser Ser
1               5

<210> SEQ ID NO 75
<211> LENGTH: 5
<212> TYPE: PRT
<213> ORGANISM: Artificial Sequence
<220> FEATURE:
<223> OTHER INFORMATION: C-terminal end

<400> SEQUENCE: 75

Val Gln Val Ser Ser
1               5

<210> SEQ ID NO 76
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 76

Val Thr Val Lys Ser Xaa
1               5

<210> SEQ ID NO 77
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 77

Val Thr Val Gln Ser Xaa
1               5

<210> SEQ ID NO 78
<211> LENGTH: 6
<212> TYPE: PRT
<213> ORGANISM: Artificial Sequence
<220> FEATURE:
```

```
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 78

Val Lys Val Ser Ser Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 79

Val Gln Val Ser Ser Xaa
1               5

<210> SEQ ID NO 80
<211> LENGTH: 6
<212> TYPE: PRT
<213> ORGANISM: Artificial Sequence
<220> FEATURE:
<223> OTHER INFORMATION: C-terminal end

<400> SEQUENCE: 80

Val Thr Val Lys Ser Ala
1               5

<210> SEQ ID NO 81
<211> LENGTH: 6
<212> TYPE: PRT
<213> ORGANISM: Artificial Sequence
<220> FEATURE:
<223> OTHER INFORMATION: C-terminal end

<400> SEQUENCE: 81

Val Thr Val Gln Ser Ala
1               5

<210> SEQ ID NO 82
<211> LENGTH: 6
<212> TYPE: PRT
<213> ORGANISM: Artificial Sequence
<220> FEATURE:
<223> OTHER INFORMATION: C-terminal end

<400> SEQUENCE: 82

Val Lys Val Ser Ser Ala
1               5

<210> SEQ ID NO 83
<211> LENGTH: 6
<212> TYPE: PRT
<213> ORGANISM: Artificial Sequence
<220> FEATURE:
<223> OTHER INFORMATION: C-terminal end
```

```
<400> SEQUENCE: 83

Val Gln Val Ser Ser Ala
1               5

<210> SEQ ID NO 84
<211> LENGTH: 5
<212> TYPE: PRT
<213> ORGANISM: Artificial Sequence
<220> FEATURE:
<223> OTHER INFORMATION: C-terminal end

<400> SEQUENCE: 84

Val Thr Val Ser Ser
1               5

<210> SEQ ID NO 85
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 85

Val Thr Val Ser Ser Xaa
1               5

<210> SEQ ID NO 86
<211> LENGTH: 6
<212> TYPE: PRT
<213> ORGANISM: Artificial Sequence
<220> FEATURE:
<223> OTHER INFORMATION: C-terminal end

<400> SEQUENCE: 86

Thr Val Thr Ser Ser Ala
1               5

<210> SEQ ID NO 87
<211> LENGTH: 129
<212> TYPE: PRT
<213> ORGANISM: Artificial Sequence
<220> FEATURE:
<223> OTHER INFORMATION: CDR Sequence

<400> SEQUENCE: 87

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
```

```
                    100                 105                 110
Lys Tyr Glu Tyr Glu Tyr Trp Gly Gln Gly Thr Gln Val Thr Val Ser
            115                 120                 125
Ser
```

<210> SEQ ID NO 88
<211> LENGTH: 130
<212> TYPE: PRT
<213> ORGANISM: Artificial Sequence
<220> FEATURE:
<223> OTHER INFORMATION: CDR Sequence

<400> SEQUENCE: 88

```
Glu Val Gln Leu Val Glu Ser Gly Gly Lys Leu Val Gln Ala Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130
```

<210> SEQ ID NO 89
<211> LENGTH: 115
<212> TYPE: PRT
<213> ORGANISM: Artificial Sequence
<220> FEATURE:
<223> OTHER INFORMATION: CDR Sequence

<400> SEQUENCE: 89

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
    115
```

<210> SEQ ID NO 90
<211> LENGTH: 115
<212> TYPE: PRT
<213> ORGANISM: Artificial Sequence
<220> FEATURE:
<223> OTHER INFORMATION: CDR Sequence

<400> SEQUENCE: 90

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 91
<211> LENGTH: 115
<212> TYPE: PRT
<213> ORGANISM: Artificial Sequence
<220> FEATURE:
<223> OTHER INFORMATION: CDR Sequence

<400> SEQUENCE: 91

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser
        115
```

<210> SEQ ID NO 92
<211> LENGTH: 115
<212> TYPE: PRT
<213> ORGANISM: Artificial Sequence
<220> FEATURE:
<223> OTHER INFORMATION: CDR Sequence

<400> SEQUENCE: 92

```
Glu Val Gln Leu Leu Glu Ser Gly Gly Gly Val Val Gln Pro Gly Gly
1               5                   10                  15
```

Ser Leu Arg Leu Ser Cys Ala Ala Ser Gly Phe Thr Phe Arg Ser Phe
        20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 93
<211> LENGTH: 417
<212> TYPE: PRT
<213> ORGANISM: Artificial Sequence
<220> FEATURE:
<223> OTHER INFORMATION: CDR Sequence

<400> SEQUENCE: 93

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
        20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Gly Gly Gly Gly Ser Gly Gly Gly Ser Gly Gly Gly Gly Ser
        130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Val Val Gln
                165                 170                 175

Pro Gly Gly Ser Leu Arg Leu Ser Cys Ala Ala Ser Gly Arg Thr Phe
            180                 185                 190

Arg His Tyr Ala Met Gly Trp Phe Arg Gln Ala Pro Gly Lys Glu Arg
        195                 200                 205

Glu Phe Val Ala Ala Ile Ser Ser Tyr Gly Ser Thr Asp Tyr Gly Asp
    210                 215                 220

Ser Val Lys Gly Arg Phe Thr Ile Ser Arg Asp Asp Ala Lys Asn Thr
225                 230                 235                 240

Val Pro Leu Gln Met Asn Ser Leu Lys Pro Glu Asp Thr Ala Leu Tyr
                245                 250                 255

Tyr Cys Ala Ala Ala Asp Glu Thr Leu Gly Ala Val Pro Asn Phe Arg
                260                 265                 270

Leu His Glu Lys Tyr Glu Tyr Glu Tyr Trp Gly Gln Gly Thr Leu Val
            275                 280                 285

Thr Val Ser Ser Gly Gly Gly Ser Gly Gly Gly Ser Glu Val Gln
290                 295                 300

Leu Val Glu Ser Gly Gly Gly Leu Val Gln Pro Gly Asn Ser Leu Arg
305                 310                 315                 320

Leu Ser Cys Ala Ala Ser Gly Phe Thr Phe Ser Ser Phe Gly Met Ser
                325                 330                 335

Trp Val Arg Gln Ala Pro Gly Lys Gly Leu Glu Trp Val Ser Ser Ile
                340                 345                 350

Ser Gly Ser Gly Ser Asp Thr Leu Tyr Ala Asp Ser Val Lys Gly Arg
            355                 360                 365

Phe Thr Ile Ser Arg Asp Asn Ala Lys Thr Thr Leu Tyr Leu Gln Met
        370                 375                 380

Asn Ser Leu Arg Pro Glu Asp Thr Ala Val Tyr Tyr Cys Thr Ile Gly
385                 390                 395                 400

Gly Ser Leu Ser Arg Ser Ser Gln Gly Thr Leu Val Thr Val Ser Ser
                405                 410                 415

Ala

<210> SEQ ID NO 94
<211> LENGTH: 417
<212> TYPE: PRT
<213> ORGANISM: Artificial Sequence
<220> FEATURE:
<223> OTHER INFORMATION: CDR Sequence

<400> SEQUENCE: 94

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Thr Val Ser
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Gly Val Val Gln
                165                 170                 175

Pro Gly Gly Ser Leu Arg Leu Ser Cys Ala Ala Ser Gly Arg Thr Phe
            180                 185                 190

```
Arg His Tyr Ala Met Gly Trp Phe Arg Gln Ala Pro Gly Lys Glu Arg
            195                 200                 205
Glu Phe Val Ala Ala Ile Ser Ser Tyr Gly Ser Thr Asp Tyr Gly Asp
    210                 215                 220
Ser Val Lys Gly Arg Phe Thr Ile Ser Arg Asp Asp Ala Lys Asn Thr
225                 230                 235                 240
Val Pro Leu Gln Met Asn Ser Leu Lys Pro Glu Asp Thr Ala Leu Tyr
                245                 250                 255
Tyr Cys Ala Ala Ala Asp Glu Thr Leu Gly Ala Val Pro Asn Phe Arg
            260                 265                 270
Leu His Glu Lys Tyr Glu Tyr Glu Tyr Trp Gly Gln Gly Thr Leu Val
        275                 280                 285
Thr Val Ser Ser Gly Gly Gly Ser Gly Gly Gly Ser Glu Val Gln
    290                 295                 300
Leu Val Glu Ser Gly Gly Gly Val Val Gln Pro Gly Asn Ser Leu Arg
305                 310                 315                 320
Leu Ser Cys Ala Ala Ser Gly Phe Thr Phe Ser Ser Phe Gly Met Ser
            325                 330                 335
Trp Val Arg Gln Ala Pro Gly Lys Gly Leu Glu Trp Val Ser Ser Ile
            340                 345                 350
Ser Gly Ser Gly Ser Asp Thr Leu Tyr Ala Asp Ser Val Lys Gly Arg
        355                 360                 365
Phe Thr Ile Ser Arg Asp Asn Ala Lys Thr Thr Leu Tyr Leu Gln Met
            370                 375                 380
Asn Ser Leu Arg Pro Glu Asp Thr Ala Leu Tyr Tyr Cys Thr Ile Gly
385                 390                 395                 400
Gly Ser Leu Ser Arg Ser Ser Gln Gly Thr Leu Val Thr Val Ser Ser
                405                 410                 415
Ala

<210> SEQ ID NO 95
<211> LENGTH: 417
<212> TYPE: PRT
<213> ORGANISM: Artificial Sequence
<220> FEATURE:
<223> OTHER INFORMATION: CDR Sequence

<400> SEQUENCE: 95

Asp Val Gln Leu Val Glu Ser Gly Gly Gly Val Val Gln Pro Gly Gly
1               5                   10                  15
Ser Leu Arg Leu Ser Cys Ala Ala Ser Gly Arg Thr Phe Arg His Tyr
            20                  25                  30
Ala Met Gly Trp Phe Arg Gln Ala Pro Gly Lys Glu Arg Glu Phe Val
        35                  40                  45
Ala Ala Ile Ser Ser Tyr Gly Ser Thr Asp Tyr Gly Asp Ser Val Lys
    50                  55                  60
Gly Arg Phe Thr Ile Ser Arg Asp Asp Ala Lys Asn Thr Val Pro Leu
65                  70                  75                  80
Gln Met Asn Ser Leu Lys Pro Glu Asp Thr Ala Leu Tyr Tyr Cys Ala
                85                  90                  95
Ala Ala Asp Glu Thr Leu Gly Ala Val Pro Asn Phe Arg Leu His Glu
            100                 105                 110
Lys Tyr Glu Tyr Glu Tyr Trp Gly Gln Gly Thr Leu Val Thr Val Ser
        115                 120                 125
Ser Gly Gly Gly Gly Ser Gly Gly Gly Gly Ser Gly Gly Gly Gly Ser
```

```
                130               135                140
Gly Gly Gly Gly Ser Gly Gly Gly Ser Gly Gly Gly Ser Gly
145                 150                 155                 160

Gly Gly Gly Glu Val Gln Leu Val Glu Ser Gly Gly Val Val Gln
                165                 170                 175

Pro Gly Gly Ser Leu Arg Leu Ser Cys Ala Ala Ser Gly Arg Thr Phe
                180                 185                 190

Arg His Tyr Ala Met Gly Trp Phe Arg Gln Ala Pro Gly Lys Glu Arg
                195                 200                 205

Glu Phe Val Ala Ala Ile Ser Ser Tyr Gly Ser Thr Asp Tyr Gly Asp
                210                 215                 220

Ser Val Lys Gly Arg Phe Thr Ile Ser Arg Asp Asp Ala Lys Asn Thr
225                 230                 235                 240

Val Pro Leu Gln Met Asn Ser Leu Lys Pro Glu Asp Thr Ala Leu Tyr
                245                 250                 255

Tyr Cys Ala Ala Ala Asp Glu Thr Leu Gly Ala Val Pro Asn Phe Arg
                260                 265                 270

Leu His Glu Lys Tyr Glu Tyr Glu Tyr Trp Gly Gln Gly Thr Leu Val
                275                 280                 285

Thr Val Ser Ser Gly Gly Gly Gly Ser Gly Gly Gly Ser Glu Val Gln
                290                 295                 300

Leu Val Glu Ser Gly Gly Gly Val Val Gln Pro Gly Asn Ser Leu Arg
305                 310                 315                 320

Leu Ser Cys Ala Ala Ser Gly Phe Thr Phe Ser Ser Phe Gly Met Ser
                325                 330                 335

Trp Val Arg Gln Ala Pro Gly Lys Gly Leu Glu Trp Val Ser Ser Ile
                340                 345                 350

Ser Gly Ser Gly Ser Asp Thr Leu Tyr Ala Asp Ser Val Lys Gly Arg
                355                 360                 365

Phe Thr Ile Ser Arg Asp Asn Ala Lys Thr Thr Leu Tyr Leu Gln Met
                370                 375                 380

Asn Ser Leu Arg Pro Glu Asp Thr Ala Leu Tyr Tyr Cys Thr Ile Gly
385                 390                 395                 400

Gly Ser Leu Ser Arg Ser Ser Gln Gly Thr Leu Val Lys Val Ser Ser
                405                 410                 415

Ala

<210> SEQ ID NO 96
<211> LENGTH: 417
<212> TYPE: PRT
<213> ORGANISM: Artificial Sequence
<220> FEATURE:
<223> OTHER INFORMATION: CDR Sequence

<400> SEQUENCE: 96

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
                35                  40                  45

Ala Ala Ile Ser Ser Tyr Gly Ser Thr Asp Tyr Gly Asp Ser Val Lys
                50                  55                  60

Gly Arg Phe Thr Ile Ser Arg Asp Asp Ala Lys Asn Thr Val Pro Leu
65                  70                  75                  80
```

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Val Val Gln
                165                 170                 175

Pro Gly Gly Ser Leu Arg Leu Ser Cys Ala Ala Ser Gly Arg Thr Phe
            180                 185                 190

Arg His Tyr Ala Met Gly Trp Phe Arg Gln Ala Pro Gly Lys Glu Arg
        195                 200                 205

Glu Phe Val Ala Ala Ile Ser Ser Tyr Gly Ser Thr Asp Tyr Gly Asp
    210                 215                 220

Ser Val Lys Gly Arg Phe Thr Ile Ser Arg Asp Asp Ala Lys Asn Thr
225                 230                 235                 240

Val Pro Leu Gln Met Asn Ser Leu Lys Pro Glu Asp Thr Ala Leu Tyr
            245                 250                 255

Tyr Cys Ala Ala Asp Glu Thr Leu Gly Ala Val Pro Asn Phe Arg
        260                 265                 270

Leu His Glu Lys Tyr Glu Tyr Glu Tyr Trp Gly Gln Gly Thr Leu Val
            275                 280                 285

Lys Val Ser Ser Gly Gly Gly Ser Gly Gly Gly Ser Glu Val Gln
            290                 295                 300

Leu Val Glu Ser Gly Gly Gly Leu Val Gln Pro Gly Asn Ser Leu Arg
305                 310                 315                 320

Leu Ser Cys Ala Ala Ser Gly Phe Thr Phe Ser Ser Phe Gly Met Ser
            325                 330                 335

Trp Val Arg Gln Ala Pro Gly Lys Gly Leu Glu Trp Val Ser Ser Ile
            340                 345                 350

Ser Gly Ser Gly Ser Asp Thr Leu Tyr Ala Asp Ser Val Lys Gly Arg
            355                 360                 365

Phe Thr Ile Ser Arg Asp Asn Ala Lys Thr Thr Leu Tyr Leu Gln Met
        370                 375                 380

Asn Ser Leu Arg Pro Glu Asp Thr Ala Val Tyr Tyr Cys Thr Ile Gly
385                 390                 395                 400

Gly Ser Leu Ser Arg Ser Ser Gln Gly Thr Leu Val Thr Val Ser Ser
            405                 410                 415

Ala

<210> SEQ ID NO 97
<211> LENGTH: 417
<212> TYPE: PRT
<213> ORGANISM: Artificial Sequence
<220> FEATURE:
<223> OTHER INFORMATION: CDR Sequence

<400> SEQUENCE: 97

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Val Val Gln
            165                 170                 175

Pro Gly Gly Ser Leu Arg Leu Ser Cys Ala Ala Ser Gly Arg Thr Phe
        180                 185                 190

Arg His Tyr Ala Met Gly Trp Phe Arg Gln Ala Pro Gly Lys Glu Arg
    195                 200                 205

Glu Phe Val Ala Ala Ile Ser Ser Tyr Gly Ser Thr Asp Tyr Gly Asp
210                 215                 220

Ser Val Lys Gly Arg Phe Thr Ile Ser Arg Asp Asp Ala Lys Asn Thr
225                 230                 235                 240

Val Pro Leu Gln Met Asn Ser Leu Lys Pro Glu Asp Thr Ala Leu Tyr
            245                 250                 255

Tyr Cys Ala Ala Ala Asp Glu Thr Leu Gly Ala Val Pro Asn Phe Arg
        260                 265                 270

Leu His Glu Lys Tyr Glu Tyr Glu Tyr Trp Gly Gln Gly Thr Leu Val
    275                 280                 285

Lys Val Ser Ser Gly Gly Gly Ser Gly Gly Gly Ser Glu Val Gln
290                 295                 300

Leu Val Glu Ser Gly Gly Val Val Gln Pro Gly Asn Ser Leu Arg
305                 310                 315                 320

Leu Ser Cys Ala Ala Ser Gly Phe Thr Phe Ser Ser Phe Gly Met Ser
            325                 330                 335

Trp Val Arg Gln Ala Pro Gly Lys Gly Leu Glu Trp Val Ser Ser Ile
        340                 345                 350

Ser Gly Ser Gly Ser Asp Thr Leu Tyr Ala Asp Ser Val Lys Gly Arg
    355                 360                 365

Phe Thr Ile Ser Arg Asp Asn Ala Lys Thr Thr Leu Tyr Leu Gln Met
370                 375                 380

Asn Ser Leu Arg Pro Glu Asp Thr Ala Leu Tyr Tyr Cys Thr Ile Gly
385                 390                 395                 400

Gly Ser Leu Ser Arg Ser Ser Gln Gly Thr Leu Val Thr Val Ser Ser
            405                 410                 415

Ala

<210> SEQ ID NO 98

-continued

<211> LENGTH: 417
<212> TYPE: PRT
<213> ORGANISM: Artificial Sequence
<220> FEATURE:
<223> OTHER INFORMATION: CDR Sequence

<400> SEQUENCE: 98

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser Gly Gly Gly Ser Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Glu Val Gln Leu Val Glu Ser Gly Gly Gly Val Val Gln
                165                 170                 175

Pro Gly Gly Ser Leu Arg Leu Ser Cys Ala Ala Ser Gly Arg Thr Phe
            180                 185                 190

Arg His Tyr Ala Met Gly Trp Phe Arg Gln Ala Pro Gly Lys Glu Arg
        195                 200                 205

Glu Phe Val Ala Ala Ile Ser Ser Tyr Gly Ser Thr Asp Tyr Gly Asp
    210                 215                 220

Ser Val Lys Gly Arg Phe Thr Ile Ser Arg Asp Asp Ala Lys Asn Thr
225                 230                 235                 240

Val Pro Leu Gln Met Asn Ser Leu Lys Pro Glu Asp Thr Ala Leu Tyr
                245                 250                 255

Tyr Cys Ala Ala Ala Asp Glu Thr Leu Gly Ala Val Pro Asn Phe Arg
            260                 265                 270

Leu His Glu Lys Tyr Glu Tyr Glu Tyr Trp Gly Gln Gly Thr Leu Val
        275                 280                 285

Lys Val Ser Ser Gly Gly Gly Gly Ser Gly Gly Gly Ser Glu Val Gln
    290                 295                 300

Leu Val Glu Ser Gly Gly Gly Val Val Gln Pro Gly Asn Ser Leu Arg
305                 310                 315                 320

Leu Ser Cys Ala Ala Ser Gly Phe Thr Phe Ser Ser Phe Gly Met Ser
                325                 330                 335

Trp Val Arg Gln Ala Pro Gly Lys Gly Leu Glu Trp Val Ser Ser Ile
            340                 345                 350

Ser Gly Ser Gly Ser Asp Thr Leu Tyr Ala Asp Ser Val Lys Gly Arg
        355                 360                 365

Phe Thr Ile Ser Arg Asp Asn Ala Lys Thr Thr Leu Tyr Leu Gln Met
    370                 375                 380

-continued

Asn Ser Leu Arg Pro Glu Asp Thr Ala Leu Tyr Tyr Cys Thr Ile Gly
385                 390                 395                 400

Gly Ser Leu Ser Arg Ser Ser Gln Gly Thr Leu Val Lys Val Ser Ser
            405                 410                 415

Ala

<210> SEQ ID NO 99
<211> LENGTH: 419
<212> TYPE: PRT
<213> ORGANISM: Artificial Sequence
<220> FEATURE:
<223> OTHER INFORMATION: CDR Sequence

<400> SEQUENCE: 99

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Ser Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Lys Val Val
                165                 170                 175

Gln Pro Gly Gly Ser Leu Arg Leu Ser Cys Ser Ala Ser Gly Arg Thr
            180                 185                 190

Phe Ser Phe Ser Thr Ser Thr Met Gly Trp Phe Arg Gln Ala Pro Gly
        195                 200                 205

Lys Glu Leu Glu Phe Val Ala Ala Ile Asp Trp Ser Asp Phe Asn Thr
    210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
                245                 250                 255

Thr Ala Leu Tyr Tyr Cys Ala Ala His Ser Glu Thr Arg Gly Gly Thr
            260                 265                 270

Arg Tyr Phe Asp Arg Pro Ser Leu Tyr Asn Tyr Trp Gly Gln Gly Thr
        275                 280                 285

Leu Val Thr Val Ser Ser Gly Gly Gly Gly Ser Gly Gly Gly Ser Glu
    290                 295                 300

Val Gln Leu Val Glu Ser Gly Gly Gly Leu Val Gln Pro Gly Asn Ser
305                 310                 315                 320

```
Leu Arg Leu Ser Cys Ala Ala Ser Gly Phe Thr Ser Ser Phe Gly
            325                 330                 335

Met Ser Trp Val Arg Gln Ala Pro Gly Lys Gly Leu Glu Trp Val Ser
            340                 345                 350

Ser Ile Ser Gly Ser Gly Ser Asp Thr Leu Tyr Ala Asp Ser Val Lys
            355                 360                 365

Gly Arg Phe Thr Ile Ser Arg Asp Asn Ala Lys Thr Thr Leu Tyr Leu
            370                 375                 380

Gln Met Asn Ser Leu Arg Pro Glu Asp Thr Ala Val Tyr Tyr Cys Thr
385                 390                 395                 400

Ile Gly Gly Ser Leu Ser Arg Ser Ser Gln Gly Thr Leu Val Thr Val
            405                 410                 415

Ser Ser Ala

<210> SEQ ID NO 100
<211> LENGTH: 419
<212> TYPE: PRT
<213> ORGANISM: Artificial Sequence
<220> FEATURE:
<223> OTHER INFORMATION: CDR Sequence

<400> SEQUENCE: 100

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
            50                  55                  60

Ser Val Lys Gly Arg Phe Thr Ile Ser Arg His Asn Pro Arg Asn Ser
65              70                  75                  80

Val Tyr Leu Gln Leu Asn Ser Leu Lys Pro Glu Asp Thr Ala Leu Tyr
            85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
            115                 120                 125

Ser Ser Gly Gly Gly Gly Ser Gly Gly Gly Gly Ser Gly Gly Gly Gly
            130                 135                 140

Ser Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Lys Val Val
                165                 170                 175

Gln Pro Gly Gly Ser Leu Arg Leu Ser Cys Ser Ala Ser Gly Arg Thr
            180                 185                 190

Phe Ser Phe Ser Thr Ser Thr Met Gly Trp Phe Arg Gln Ala Pro Gly
            195                 200                 205

Lys Glu Leu Glu Phe Val Ala Ala Ile Asp Trp Ser Asp Phe Asn Thr
            210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
            245                 250                 255

Thr Ala Leu Tyr Tyr Cys Ala Ala His Ser Glu Thr Arg Gly Gly Thr
```

```
                260               265               270
Arg Tyr Phe Asp Arg Pro Ser Leu Tyr Asn Tyr Trp Gly Gln Gly Thr
            275               280               285

Leu Val Thr Val Ser Ser Gly Gly Gly Gly Ser Gly Gly Gly Ser Glu
        290               295               300

Val Gln Leu Val Glu Ser Gly Gly Val Val Gln Pro Gly Asn Ser
305               310               315               320

Leu Arg Leu Ser Cys Ala Ala Ser Gly Phe Thr Phe Ser Ser Phe Gly
            325               330               335

Met Ser Trp Val Arg Gln Ala Pro Gly Lys Gly Leu Glu Trp Val Ser
            340               345               350

Ser Ile Ser Gly Ser Gly Ser Asp Thr Leu Tyr Ala Asp Ser Val Lys
            355               360               365

Gly Arg Phe Thr Ile Ser Arg Asp Asn Ala Lys Thr Thr Leu Tyr Leu
            370               375               380

Gln Met Asn Ser Leu Arg Pro Glu Asp Thr Ala Leu Tyr Tyr Cys Thr
385               390               395               400

Ile Gly Gly Ser Leu Ser Arg Ser Ser Gln Gly Thr Leu Val Thr Val
                405               410               415

Ser Ser Ala

<210> SEQ ID NO 101
<211> LENGTH: 419
<212> TYPE: PRT
<213> ORGANISM: Artificial Sequence
<220> FEATURE:
<223> OTHER INFORMATION: CDR Sequence

<400> SEQUENCE: 101

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Leu Val Thr Val
            115                 120                 125

Ser Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Lys Val Val
                165                 170                 175

Gln Pro Gly Gly Ser Leu Arg Leu Ser Cys Ser Ala Ser Gly Arg Thr
            180                 185                 190

Phe Ser Phe Ser Thr Ser Thr Met Gly Trp Phe Arg Gln Ala Pro Gly
        195                 200                 205
```

```
Lys Glu Leu Glu Phe Val Ala Ala Ile Asp Trp Ser Asp Phe Asn Thr
    210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
                245                 250                 255

Thr Ala Leu Tyr Tyr Cys Ala Ala His Ser Glu Thr Arg Gly Gly Thr
            260                 265                 270

Arg Tyr Phe Asp Arg Pro Ser Leu Tyr Asn Tyr Trp Gly Gln Gly Thr
        275                 280                 285

Leu Val Thr Val Ser Ser Gly Gly Gly Ser Gly Gly Gly Ser Glu
    290                 295                 300

Val Gln Leu Val Glu Ser Gly Gly Val Val Gln Pro Gly Asn Ser
305                 310                 315                 320

Leu Arg Leu Ser Cys Ala Ala Ser Gly Phe Thr Phe Ser Ser Phe Gly
                325                 330                 335

Met Ser Trp Val Arg Gln Ala Pro Gly Lys Gly Leu Glu Trp Val Ser
            340                 345                 350

Ser Ile Ser Gly Ser Gly Ser Asp Thr Leu Tyr Ala Asp Ser Val Lys
        355                 360                 365

Gly Arg Phe Thr Ile Ser Arg Asp Asn Ala Lys Thr Thr Leu Tyr Leu
    370                 375                 380

Gln Met Asn Ser Leu Arg Pro Glu Asp Thr Ala Leu Tyr Tyr Cys Thr
385                 390                 395                 400

Ile Gly Gly Ser Leu Ser Arg Ser Ser Gln Gly Thr Leu Val Lys Val
                405                 410                 415

Ser Ser Ala

<210> SEQ ID NO 102
<211> LENGTH: 419
<212> TYPE: PRT
<213> ORGANISM: Artificial Sequence
<220> FEATURE:
<223> OTHER INFORMATION: CDR Sequence

<400> SEQUENCE: 102

Asp Val Gln Leu Val Glu Ser Gly Gly Lys Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Gly Gly Gly Gly Ser Gly Gly Gly Gly Ser Gly Gly Gly Gly
    130                 135                 140
```

Ser Gly Gly Gly Gly Ser Gly Gly Gly Ser Gly Gly Gly Ser
145                 150                 155                 160

Gly Gly Gly Gly Glu Val Gln Leu Val Glu Ser Gly Gly Lys Val Val
                165                 170                 175

Gln Pro Gly Gly Ser Leu Arg Leu Ser Cys Ser Ala Ser Gly Arg Thr
            180                 185                 190

Phe Ser Phe Ser Thr Ser Thr Met Gly Trp Phe Arg Gln Ala Pro Gly
        195                 200                 205

Lys Glu Leu Glu Phe Val Ala Ala Ile Asp Trp Ser Asp Phe Asn Thr
    210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
                245                 250                 255

Thr Ala Leu Tyr Tyr Cys Ala Ala His Ser Glu Thr Arg Gly Gly Thr
            260                 265                 270

Arg Tyr Phe Asp Arg Pro Ser Leu Tyr Asn Tyr Trp Gly Gln Gly Thr
        275                 280                 285

Leu Val Lys Val Ser Ser Gly Gly Gly Gly Ser Gly Gly Gly Ser Glu
    290                 295                 300

Val Gln Leu Val Glu Ser Gly Gly Leu Val Gln Pro Gly Asn Ser
305                 310                 315                 320

Leu Arg Leu Ser Cys Ala Ala Ser Gly Phe Thr Phe Ser Ser Phe Gly
                325                 330                 335

Met Ser Trp Val Arg Gln Ala Pro Gly Lys Gly Leu Glu Trp Val Ser
            340                 345                 350

Ser Ile Ser Gly Ser Gly Ser Asp Thr Leu Tyr Ala Asp Ser Val Lys
        355                 360                 365

Gly Arg Phe Thr Ile Ser Arg Asp Asn Ala Lys Thr Thr Leu Tyr Leu
    370                 375                 380

Gln Met Asn Ser Leu Arg Pro Glu Asp Thr Ala Val Tyr Tyr Cys Thr
385                 390                 395                 400

Ile Gly Gly Ser Leu Ser Arg Ser Ser Gln Gly Thr Leu Val Thr Val
                405                 410                 415

Ser Ser Ala

<210> SEQ ID NO 103
<211> LENGTH: 419
<212> TYPE: PRT
<213> ORGANISM: Artificial Sequence
<220> FEATURE:
<223> OTHER INFORMATION: CDR Sequence

<400> SEQUENCE: 103

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr

```
                    85                  90                  95
Tyr Cys Ala Ala His Ser Glu Thr Arg Gly Gly Thr Arg Tyr Phe Asp
                100                 105                 110
Arg Pro Ser Leu Tyr Asn Tyr Trp Gly Gln Gly Thr Leu Val Lys Val
                115                 120                 125
Ser Ser Gly Gly Gly Gly Ser Gly Gly Gly Gly Ser Gly Gly Gly Gly
145                 150                 155                 160
Ser Gly Gly Gly Ser Gly Gly Gly Gly Ser Gly Gly Gly Ser
145                 150                 155                 160
Gly Gly Gly Gly Glu Val Gln Leu Val Glu Ser Gly Gly Lys Val Val
                165                 170                 175
Gln Pro Gly Gly Ser Leu Arg Leu Ser Cys Ser Ala Ser Gly Arg Thr
                180                 185                 190
Phe Ser Phe Ser Thr Ser Thr Met Gly Trp Phe Arg Gln Ala Pro Gly
                195                 200                 205
Lys Glu Leu Glu Phe Val Ala Ala Ile Asp Trp Ser Asp Phe Asn Thr
                210                 215                 220
Tyr Tyr Ala Asp Ser Val Lys Gly Arg Phe Thr Ile Ser Arg His Asn
225                 230                 235                 240
Pro Arg Asn Ser Val Tyr Leu Gln Leu Asn Ser Leu Lys Pro Glu Asp
                245                 250                 255
Thr Ala Leu Tyr Tyr Cys Ala Ala His Ser Glu Thr Arg Gly Gly Thr
                260                 265                 270
Arg Tyr Phe Asp Arg Pro Ser Leu Tyr Asn Tyr Trp Gly Gln Gly Thr
                275                 280                 285
Leu Val Lys Val Ser Ser Gly Gly Gly Gly Ser Gly Gly Gly Ser Glu
                290                 295                 300
Val Gln Leu Val Glu Ser Gly Gly Val Val Gln Pro Gly Asn Ser
305                 310                 315                 320
Leu Arg Leu Ser Cys Ala Ala Ser Gly Phe Thr Phe Ser Ser Phe Gly
                325                 330                 335
Met Ser Trp Val Arg Gln Ala Pro Gly Lys Gly Leu Glu Trp Val Ser
                340                 345                 350
Ser Ile Ser Gly Ser Gly Ser Asp Thr Leu Tyr Ala Asp Ser Val Lys
                355                 360                 365
Gly Arg Phe Thr Ile Ser Arg Asp Asn Ala Lys Thr Thr Leu Tyr Leu
                370                 375                 380
Gln Met Asn Ser Leu Arg Pro Glu Asp Thr Ala Leu Tyr Tyr Cys Thr
385                 390                 395                 400
Ile Gly Gly Ser Leu Ser Arg Ser Ser Gln Gly Thr Leu Val Thr Val
                405                 410                 415
Ser Ser Ala

<210> SEQ ID NO 104
<211> LENGTH: 419
<212> TYPE: PRT
<213> ORGANISM: Artificial Sequence
<220> FEATURE:
<223> OTHER INFORMATION: CDR Sequence

<400> SEQUENCE: 104

Asp Val Gln Leu Val Glu Ser Gly Gly Lys Val Val Gln Pro Gly Gly
1               5                   10                  15
Ser Leu Arg Leu Ser Cys Ser Ala Ser Gly Arg Thr Phe Ser Phe Ser
                20                  25                  30
```

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Lys Val Val
                165                 170                 175

Gln Pro Gly Gly Ser Leu Arg Leu Ser Cys Ser Ala Ser Gly Arg Thr
        180                 185                 190

Phe Ser Phe Ser Thr Ser Thr Met Gly Trp Phe Arg Gln Ala Pro Gly
    195                 200                 205

Lys Glu Leu Glu Phe Val Ala Ala Ile Asp Trp Ser Asp Phe Asn Thr
        210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
                245                 250                 255

Thr Ala Leu Tyr Tyr Cys Ala Ala His Ser Glu Thr Arg Gly Gly Thr
        260                 265                 270

Arg Tyr Phe Asp Arg Pro Ser Leu Tyr Asn Tyr Trp Gly Gln Gly Thr
    275                 280                 285

Leu Val Lys Val Ser Ser Gly Gly Gly Ser Gly Gly Gly Ser Glu
        290                 295                 300

Val Gln Leu Val Glu Ser Gly Gly Val Val Gln Pro Gly Asn Ser
305                 310                 315                 320

Leu Arg Leu Ser Cys Ala Ala Ser Gly Phe Thr Phe Ser Ser Phe Gly
                325                 330                 335

Met Ser Trp Val Arg Gln Ala Pro Gly Lys Gly Leu Glu Trp Val Ser
        340                 345                 350

Ser Ile Ser Gly Ser Gly Ser Asp Thr Leu Tyr Ala Asp Ser Val Lys
    355                 360                 365

Gly Arg Phe Thr Ile Ser Arg Asp Asn Ala Lys Thr Thr Leu Tyr Leu
370                 375                 380

Gln Met Asn Ser Leu Arg Pro Glu Asp Thr Ala Leu Tyr Tyr Cys Thr
385                 390                 395                 400

Ile Gly Gly Ser Leu Ser Arg Ser Ser Gln Gly Thr Leu Val Lys Val
                405                 410                 415

Ser Ser Ala

<210> SEQ ID NO 105
<211> LENGTH: 418
<212> TYPE: PRT

<213> ORGANISM: Artificial Sequence
<220> FEATURE:
<223> OTHER INFORMATION: CDR Sequence

<400> SEQUENCE: 105

```
Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
    210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
        275                 280                 285

Val Thr Val Ser Ser Gly Gly Gly Gly Ser Gly Gly Gly Ser Glu Val
    290                 295                 300

Gln Leu Val Glu Ser Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Val Tyr Tyr Cys Thr Ile
```

```
                385                 390                 395                 400
Gly Gly Ser Leu Ser Arg Ser Ser Gln Gly Thr Leu Thr Val Ser
                    405                 410                 415

Ser Ala

<210> SEQ ID NO 106
<211> LENGTH: 418
<212> TYPE: PRT
<213> ORGANISM: Artificial Sequence
<220> FEATURE:
<223> OTHER INFORMATION: CDR Sequence

<400> SEQUENCE: 106

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
    210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
        275                 280                 285

Val Thr Val Ser Ser Gly Gly Gly Gly Ser Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335
```

-continued

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Gln Gly Thr Leu Val Thr Val Ser
                405                 410                 415

Ser Ala

<210> SEQ ID NO 107
<211> LENGTH: 418
<212> TYPE: PRT
<213> ORGANISM: Artificial Sequence
<220> FEATURE:
<223> OTHER INFORMATION: CDR Sequence

<400> SEQUENCE: 107

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Glu Val Gln Leu Val Glu Ser Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
    210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

```
Tyr Phe Asp Arg Pro Ser Leu Tyr Asn Tyr Trp Gly Gln Gly Thr Leu
            275                 280                 285

Val Thr Val Ser Ser Gly Gly Gly Ser Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415

Ser Ala

<210> SEQ ID NO 108
<211> LENGTH: 418
<212> TYPE: PRT
<213> ORGANISM: Artificial Sequence
<220> FEATURE:
<223> OTHER INFORMATION: CDR Sequence

<400> SEQUENCE: 108

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
```

```
                 210                 215                 220
Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
                260                 265                 270

Tyr Phe Asp Arg Pro Ser Leu Tyr Asn Tyr Trp Gly Gln Gly Thr Leu
            275                 280                 285

Val Lys Val Ser Ser Gly Gly Gly Ser Gly Gly Gly Ser Glu Val
        290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
        370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 109
<211> LENGTH: 418
<212> TYPE: PRT
<213> ORGANISM: Artificial Sequence
<220> FEATURE:
<223> OTHER INFORMATION: CDR Sequence

<400> SEQUENCE: 109

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160
```

Gly Gly Gly Glu Val Gln Leu Val Glu Ser Gly Gly Lys Val Val Gln
            165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
            195                 200                 205

Glu Leu Glu Phe Val Ala Ala Ile Asp Trp Ser Asp Phe Asn Thr Tyr
            210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
            275                 280                 285

Val Lys Val Ser Ser Gly Gly Gly Gly Ser Gly Gly Gly Ser Glu Val
            290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
            325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
            370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
            405                 410                 415

Ser Ala

<210> SEQ ID NO 110
<211> LENGTH: 418
<212> TYPE: PRT
<213> ORGANISM: Artificial Sequence
<220> FEATURE:
<223> OTHER INFORMATION: CDR Sequence

<400> SEQUENCE: 110

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
            50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
    210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
        275                 280                 285

Val Lys Val Ser Ser Gly Gly Gly Gly Ser Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415

Ser Ala

<210> SEQ ID NO 111
<211> LENGTH: 418
<212> TYPE: PRT
<213> ORGANISM: Artificial Sequence
<220> FEATURE:
<223> OTHER INFORMATION: CDR Sequence

<400> SEQUENCE: 111

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val

```
            35                  40                  45
Ala Ala Ile Ser Ser Tyr Gly Ser Thr Asp Tyr Gly Asp Ser Val Lys
 50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Leu Tyr Tyr Cys Ala
                 85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Lys Val Ser
                115                 120                 125

Ser Gly Gly Gly Gly Ser Gly Gly Gly Ser Gly Gly Gly Gly Gly Ser
130                 135                 140

Gly Gly Gly Gly Ser Gly Gly Gly Ser Gly Gly Gly Gly Ser Gly Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
                180                 185                 190

Ser Phe Ser Thr Ser Thr Met Gly Trp Phe Arg Gln Ala Pro Gly Lys
                195                 200                 205

Glu Leu Glu Phe Val Ala Ala Ile Asp Trp Ser Asp Phe Asn Thr Tyr
210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
                260                 265                 270

Tyr Phe Asp Arg Pro Ser Leu Tyr Asn Tyr Trp Gly Gln Gly Thr Leu
                275                 280                 285

Val Thr Val Ser Ser Gly Gly Gly Gly Ser Gly Gly Gly Ser Glu Val
290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 112
<211> LENGTH: 418
<212> TYPE: PRT
<213> ORGANISM: Artificial Sequence
<220> FEATURE:
```

<223> OTHER INFORMATION: CDR Sequence

<400> SEQUENCE: 112

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
            85                  90                  95

Ala Ala Asp Glu Thr Leu Gly Ala Val Pro Asn Phe Arg Leu His Glu
        100                 105                 110

Lys Tyr Glu Tyr Glu Tyr Trp Gly Gln Gly Thr Leu Val Lys Val Ser
    115                 120                 125

Ser Gly Gly Gly Ser Gly Gly Gly Ser Gly Gly Gly Ser
130                 135                 140

Gly Gly Gly Gly Ser Gly Gly Gly Ser Gly Gly Gly Ser Gly
145                 150                 155                 160

Gly Gly Gly Glu Val Gln Leu Val Glu Ser Gly Gly Lys Val Val Gln
            165                 170                 175

Pro Gly Gly Ser Leu Arg Leu Ser Cys Ser Ala Ser Gly Arg Thr Phe
        180                 185                 190

Ser Phe Ser Thr Ser Thr Met Gly Trp Phe Arg Gln Ala Pro Gly Lys
            195                 200                 205

Glu Leu Glu Phe Val Ala Ala Ile Asp Trp Ser Asp Phe Asn Thr Tyr
    210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
            245                 250                 255

Ala Leu Tyr Tyr Cys Ala Ala His Ser Glu Thr Arg Gly Gly Thr Arg
        260                 265                 270

Tyr Phe Asp Arg Pro Ser Leu Tyr Asn Tyr Trp Gly Gln Gly Thr Leu
    275                 280                 285

Val Thr Val Ser Ser Gly Gly Gly Ser Gly Gly Gly Ser Glu Val
290                 295                 300

Gln Leu Val Glu Ser Gly Gly Gly Val Val Gln Pro Gly Asn Ser Leu
305                 310                 315                 320

Arg Leu Ser Cys Ala Ala Ser Gly Phe Thr Phe Ser Ser Phe Gly Met
            325                 330                 335

Ser Trp Val Arg Gln Ala Pro Gly Lys Gly Leu Glu Trp Val Ser Ser
        340                 345                 350

Ile Ser Gly Ser Gly Ser Asp Thr Leu Tyr Ala Asp Ser Val Lys Gly
    355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

```
Gly Gly Ser Leu Ser Arg Ser Gln Gly Thr Leu Val Thr Val Ser
            405                 410                 415

Ser Ala

<210> SEQ ID NO 113
<211> LENGTH: 418
<212> TYPE: PRT
<213> ORGANISM: Artificial Sequence
<220> FEATURE:
<223> OTHER INFORMATION: CDR Sequence

<400> SEQUENCE: 113

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Ser Gly Gly Gly Ser Gly
145                 150                 155                 160

Gly Gly Gly Glu Val Gln Leu Val Glu Ser Gly Gly Lys Val Val Gln
                165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
        210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
        275                 280                 285

Val Thr Val Ser Ser Gly Gly Gly Gly Ser Gly Gly Gly Ser Glu Val
        290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
```

```
                    340                 345                 350
Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
        370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
            405                 410                 415

Ser Ala

<210> SEQ ID NO 114
<211> LENGTH: 418
<212> TYPE: PRT
<213> ORGANISM: Artificial Sequence
<220> FEATURE:
<223> OTHER INFORMATION: CDR Sequence

<400> SEQUENCE: 114

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
            85                  90                  95

Ala Ala Asp Glu Thr Leu Gly Ala Val Pro Asn Phe Arg Leu His Glu
        100                 105                 110

Lys Tyr Glu Tyr Glu Tyr Trp Gly Gln Gly Thr Leu Val Lys Val Ser
    115                 120                 125

Ser Gly Gly Gly Gly Ser Gly Gly Gly Ser Gly Gly Gly Gly Ser
130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Lys Val Val Gln
            165                 170                 175

Pro Gly Gly Ser Leu Arg Leu Ser Cys Ser Ala Ser Gly Arg Thr Phe
        180                 185                 190

Ser Phe Ser Thr Ser Thr Met Gly Trp Phe Arg Gln Ala Pro Gly Lys
    195                 200                 205

Glu Leu Glu Phe Val Ala Ala Ile Asp Trp Ser Asp Phe Asn Thr Tyr
210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
            245                 250                 255

Ala Leu Tyr Tyr Cys Ala Ala His Ser Glu Thr Arg Gly Gly Thr Arg
        260                 265                 270

Tyr Phe Asp Arg Pro Ser Leu Tyr Asn Tyr Trp Gly Gln Gly Thr Leu
    275                 280                 285
```

Val Lys Val Ser Ser Gly Gly Gly Ser Gly Gly Ser Glu Val
            290                 295                 300

Gln Leu Val Glu Ser Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 115
<211> LENGTH: 418
<212> TYPE: PRT
<213> ORGANISM: Artificial Sequence
<220> FEATURE:
<223> OTHER INFORMATION: CDR Sequence

<400> SEQUENCE: 115

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Glu Val Gln Leu Val Glu Ser Gly Lys Val Val Gln
            165                 170                 175

Pro Gly Gly Ser Leu Arg Leu Ser Cys Ser Ala Ser Gly Arg Thr Phe
            180                 185                 190

Ser Phe Ser Thr Ser Thr Met Gly Trp Phe Arg Gln Ala Pro Gly Lys
        195                 200                 205

Glu Leu Glu Phe Val Ala Ala Ile Asp Trp Ser Asp Phe Asn Thr Tyr
    210                 215                 220

```
Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
            260                 265                 270

Tyr Phe Asp Arg Pro Ser Leu Tyr Asn Tyr Trp Gly Gln Gly Thr Leu
        275                 280                 285

Val Lys Val Ser Ser Gly Gly Gly Ser Gly Gly Gly Ser Glu Val
290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 116
<211> LENGTH: 418
<212> TYPE: PRT
<213> ORGANISM: Artificial Sequence
<220> FEATURE:
<223> OTHER INFORMATION: CDR Sequence

<400> SEQUENCE: 116

Asp Val Gln Leu Val Glu Ser Gly Gly Val Val Gln Pro Gly Gly
1               5                   10                  15

Ser Leu Arg Leu Ser Cys Ala Ala Ser Gly Arg Thr Phe Arg His Tyr
                20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Leu Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Lys Val Ser
        115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Gly Gly Gly Gly Ser Gly
145                 150                 155                 160

Gly Gly Gly Glu Val Gln Leu Val Glu Ser Gly Gly Lys Val Val Gln
```

```
                    165                 170                 175
Pro Gly Gly Ser Leu Arg Leu Ser Cys Ser Ala Ser Gly Arg Thr Phe
                180                 185                 190

Ser Phe Ser Thr Ser Thr Met Gly Trp Phe Arg Gln Ala Pro Gly Lys
            195                 200                 205

Glu Leu Glu Phe Val Ala Ala Ile Asp Trp Ser Asp Phe Asn Thr Tyr
        210                 215                 220

Tyr Ala Asp Ser Val Lys Gly Arg Phe Thr Ile Ser Arg His Asn Pro
225                 230                 235                 240

Arg Asn Ser Val Tyr Leu Gln Leu Asn Ser Leu Lys Pro Glu Asp Thr
                245                 250                 255

Ala Leu Tyr Tyr Cys Ala Ala His Ser Glu Thr Arg Gly Gly Thr Arg
                260                 265                 270

Tyr Phe Asp Arg Pro Ser Leu Tyr Asn Tyr Trp Gly Gln Gly Thr Leu
            275                 280                 285

Val Lys Val Ser Ser Gly Gly Gly Gly Ser Gly Gly Gly Ser Glu Val
        290                 295                 300

Gln Leu Val Glu Ser Gly Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
        370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415

Ser Ala

<210> SEQ ID NO 117
<211> LENGTH: 418
<212> TYPE: PRT
<213> ORGANISM: Artificial Sequence
<220> FEATURE:
<223> OTHER INFORMATION: CDR Sequence

<400> SEQUENCE: 117

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
                20                  25                  30

Thr Ser Thr Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
        50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110
```

```
Arg Pro Ser Leu Tyr Asn Tyr Trp Gly Gln Gly Thr Leu Val Thr Val
            115                 120                 125

Ser Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
            195                 200                 205

Arg Glu Phe Val Ala Ala Ile Ser Ser Tyr Gly Ser Thr Asp Tyr Gly
            210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
            275                 280                 285

Val Thr Val Ser Ser Gly Gly Gly Ser Gly Gly Gly Ser Glu Val
            290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
            370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 118
<211> LENGTH: 418
<212> TYPE: PRT
<213> ORGANISM: Artificial Sequence
<220> FEATURE:
<223> OTHER INFORMATION: CDR Sequence

<400> SEQUENCE: 118

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
                20                  25                  30

Thr Ser Thr Met Gly Trp Phe Arg Gln Ala Pro Gly Lys Glu Leu Glu
            35                  40                  45
```

```
Phe Val Ala Ala Ile Asp Trp Ser Asp Phe Asn Thr Tyr Tyr Ala Asp
     50                  55                  60

Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Thr Val
                115                 120                 125

Ser Ser Gly Gly Gly Ser Gly Gly Gly Ser Gly Gly Gly
130                 135                 140

Ser Gly Gly Gly Ser Gly Gly Gly Ser Gly Gly Gly Ser
145                 150                 155                 160

Gly Gly Gly Gly Glu Val Gln Leu Val Glu Ser Gly Gly Val Val
                165                 170                 175

Gln Pro Gly Gly Ser Leu Arg Leu Ser Cys Ala Ala Ser Gly Arg Thr
                180                 185                 190

Phe Arg His Tyr Ala Met Gly Trp Phe Arg Gln Ala Pro Gly Lys Glu
                195                 200                 205

Arg Glu Phe Val Ala Ala Ile Ser Ser Tyr Gly Ser Thr Asp Tyr Gly
210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
                260                 265                 270

Arg Leu His Glu Lys Tyr Glu Tyr Glu Tyr Trp Gly Gln Gly Thr Leu
                275                 280                 285

Val Thr Val Ser Ser Gly Gly Gly Ser Gly Gly Gly Ser Glu Val
                290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 119
<211> LENGTH: 418
<212> TYPE: PRT
<213> ORGANISM: Artificial Sequence
<220> FEATURE:
<223> OTHER INFORMATION: CDR Sequence
```

<400> SEQUENCE: 119

```
Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
        115                 120                 125

Ser Ser Gly Gly Gly Gly Ser Gly Gly Gly Gly Ser Gly Gly Gly Gly
130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
        195                 200                 205

Arg Glu Phe Val Ala Ala Ile Ser Ser Tyr Gly Ser Thr Asp Tyr Gly
    210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
        275                 280                 285

Val Thr Val Ser Ser Gly Gly Gly Gly Ser Gly Gly Gly Ser Glu Val
    290                 295                 300

Gln Leu Val Glu Ser Gly Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415
```

Ser Ala

<210> SEQ ID NO 120
<211> LENGTH: 418
<212> TYPE: PRT
<213> ORGANISM: Artificial Sequence
<220> FEATURE:
<223> OTHER INFORMATION: CDR Sequence

<400> SEQUENCE: 120

```
Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Gly Gly Gly Gly Ser Gly Gly Gly Gly Ser Gly Gly Gly Gly
130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
        195                 200                 205

Arg Glu Phe Val Ala Ala Ile Ser Ser Tyr Gly Ser Thr Asp Tyr Gly
    210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
        275                 280                 285

Val Thr Val Ser Ser Gly Gly Gly Gly Ser Gly Gly Gly Ser Glu Val
    290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350
```

```
Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 121
<211> LENGTH: 418
<212> TYPE: PRT
<213> ORGANISM: Artificial Sequence
<220> FEATURE:
<223> OTHER INFORMATION: CDR Sequence

<400> SEQUENCE: 121

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Leu Val Lys Val
            115                 120                 125

Ser Ser Gly Gly Gly Gly Ser Gly Gly Gly Ser Gly Gly Gly Gly
        130                 135                 140

Ser Gly Gly Gly Gly Ser Gly Gly Gly Ser Gly Gly Gly Gly Ser
145                 150                 155                 160

Gly Gly Gly Gly Glu Val Gln Leu Val Glu Ser Gly Gly Val Val
                165                 170                 175

Gln Pro Gly Gly Ser Leu Arg Leu Ser Cys Ala Ala Ser Gly Arg Thr
        180                 185                 190

Phe Arg His Tyr Ala Met Gly Trp Phe Arg Gln Ala Pro Gly Lys Glu
    195                 200                 205

Arg Glu Phe Val Ala Ala Ile Ser Ser Tyr Gly Ser Thr Asp Tyr Gly
210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
        275                 280                 285

Val Thr Val Ser Ser Gly Gly Gly Gly Ser Gly Gly Gly Ser Glu Val
```

```
                    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 122
<211> LENGTH: 418
<212> TYPE: PRT
<213> ORGANISM: Artificial Sequence
<220> FEATURE:
<223> OTHER INFORMATION: CDR Sequence

<400> SEQUENCE: 122

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
                20                  25                  30

Thr Ser Thr Met Gly Trp Phe Arg Gln Ala Pro Gly Lys Glu Leu Glu
                35                  40                  45

Phe Val Ala Ala Ile Asp Trp Ser Asp Phe Asn Thr Tyr Tyr Ala Asp
                50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Lys Val
                115                 120                 125

Ser Ser Gly Gly Gly Gly Ser Gly Gly Gly Gly Ser Gly Gly Gly Gly
                130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Val Val
                165                 170                 175

Gln Pro Gly Gly Ser Leu Arg Leu Ser Cys Ala Ala Ser Gly Arg Thr
                180                 185                 190

Phe Arg His Tyr Ala Met Gly Trp Phe Arg Gln Ala Pro Gly Lys Glu
                195                 200                 205

Arg Glu Phe Val Ala Ala Ile Ser Ser Tyr Gly Ser Thr Asp Tyr Gly
                210                 215                 220

Asp Ser Val Lys Gly Arg Phe Thr Ile Ser Arg Asp Asp Ala Lys Asn
225                 230                 235                 240
```

```
Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
            260                 265                 270

Arg Leu His Glu Lys Tyr Glu Tyr Trp Gly Gln Gly Thr Leu
            275                 280                 285

Val Thr Val Ser Ser Gly Gly Gly Ser Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415

Ser Ala

<210> SEQ ID NO 123
<211> LENGTH: 418
<212> TYPE: PRT
<213> ORGANISM: Artificial Sequence
<220> FEATURE:
<223> OTHER INFORMATION: CDR Sequence

<400> SEQUENCE: 123

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
                20                  25                  30

Thr Ser Thr Met Gly Trp Phe Arg Gln Ala Pro Gly Lys Glu Leu Glu
                35                  40                  45

Phe Val Ala Ala Ile Asp Trp Ser Asp Phe Asn Thr Tyr Tyr Ala Asp
            50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
                115                 120                 125

Ser Ser Gly Gly Gly Gly Ser Gly Gly Gly Ser Gly Gly Gly Gly
    130                 135                 140

Ser Gly Gly Gly Gly Ser Gly Gly Gly Ser Gly Gly Gly Ser
145                 150                 155                 160

Gly Gly Gly Gly Glu Val Gln Leu Val Glu Ser Gly Gly Val Val
                165                 170                 175
```

```
Gln Pro Gly Gly Ser Leu Arg Leu Ser Cys Ala Ala Ser Gly Arg Thr
            180                 185                 190
Phe Arg His Tyr Ala Met Gly Trp Phe Arg Gln Ala Pro Gly Lys Glu
        195                 200                 205
Arg Glu Phe Val Ala Ala Ile Ser Ser Tyr Gly Ser Thr Asp Tyr Gly
    210                 215                 220
Asp Ser Val Lys Gly Arg Phe Thr Ile Ser Arg Asp Asp Ala Lys Asn
225                 230                 235                 240
Thr Val Pro Leu Gln Met Asn Ser Leu Lys Pro Glu Asp Thr Ala Leu
                245                 250                 255
Tyr Tyr Cys Ala Ala Ala Asp Glu Thr Leu Gly Ala Val Pro Asn Phe
            260                 265                 270
Arg Leu His Glu Lys Tyr Glu Tyr Glu Tyr Trp Gly Gln Gly Thr Leu
        275                 280                 285
Val Lys Val Ser Ser Gly Gly Gly Ser Gly Gly Gly Ser Glu Val
    290                 295                 300
Gln Leu Val Glu Ser Gly Gly Gly Leu Val Gln Pro Gly Asn Ser Leu
305                 310                 315                 320
Arg Leu Ser Cys Ala Ala Ser Gly Phe Thr Phe Ser Ser Phe Gly Met
                325                 330                 335
Ser Trp Val Arg Gln Ala Pro Gly Lys Gly Leu Glu Trp Val Ser Ser
            340                 345                 350
Ile Ser Gly Ser Gly Ser Asp Thr Leu Tyr Ala Asp Ser Val Lys Gly
        355                 360                 365
Arg Phe Thr Ile Ser Arg Asp Asn Ala Lys Thr Thr Leu Tyr Leu Gln
    370                 375                 380
Met Asn Ser Leu Arg Pro Glu Asp Thr Ala Val Tyr Tyr Cys Thr Ile
385                 390                 395                 400
Gly Gly Ser Leu Ser Arg Ser Ser Gln Gly Thr Leu Val Thr Val Ser
                405                 410                 415
Ser Ala

<210> SEQ ID NO 124
<211> LENGTH: 418
<212> TYPE: PRT
<213> ORGANISM: Artificial Sequence
<220> FEATURE:
<223> OTHER INFORMATION: CDR Sequence

<400> SEQUENCE: 124

Asp Val Gln Leu Val Glu Ser Gly Gly Lys Val Gln Pro Gly Gly
1               5                   10                  15
Ser Leu Arg Leu Ser Cys Ser Ala Ser Gly Arg Thr Phe Ser Phe Ser
            20                  25                  30
Thr Ser Thr Met Gly Trp Phe Arg Gln Ala Pro Gly Lys Glu Leu Glu
        35                  40                  45
Phe Val Ala Ala Ile Asp Trp Ser Asp Phe Asn Thr Tyr Tyr Ala Asp
    50                  55                  60
Ser Val Lys Gly Arg Phe Thr Ile Ser Arg His Asn Pro Arg Asn Ser
65                  70                  75                  80
Val Tyr Leu Gln Leu Asn Ser Leu Lys Pro Glu Asp Thr Ala Leu Tyr
                85                  90                  95
Tyr Cys Ala Ala His Ser Glu Thr Arg Gly Gly Thr Arg Tyr Phe Asp
            100                 105                 110
Arg Pro Ser Leu Tyr Asn Tyr Trp Gly Gln Gly Thr Leu Val Thr Val
```

```
              115                 120                 125
Ser Ser Gly Gly Gly Ser Gly Gly Gly Ser Gly Gly Gly
    130                 135                 140
Ser Gly Gly Gly Ser Gly Gly Gly Ser Gly Gly Gly Ser
145                 150                 155                 160
Gly Gly Gly Gly Glu Val Gln Leu Val Glu Ser Gly Gly Val Val
                165                 170                 175
Gln Pro Gly Gly Ser Leu Arg Leu Ser Cys Ala Ala Ser Gly Arg Thr
            180                 185                 190
Phe Arg His Tyr Ala Met Gly Trp Phe Arg Gln Ala Pro Gly Lys Glu
            195                 200                 205
Arg Glu Phe Val Ala Ala Ile Ser Ser Tyr Gly Ser Thr Asp Tyr Gly
            210                 215                 220
Asp Ser Val Lys Gly Arg Phe Thr Ile Ser Arg Asp Asp Ala Lys Asn
225                 230                 235                 240
Thr Val Pro Leu Gln Met Asn Ser Leu Lys Pro Glu Asp Thr Ala Leu
                245                 250                 255
Tyr Tyr Cys Ala Ala Ala Asp Glu Thr Leu Gly Ala Val Pro Asn Phe
            260                 265                 270
Arg Leu His Glu Lys Tyr Glu Tyr Glu Tyr Trp Gly Gln Gly Thr Leu
            275                 280                 285
Val Lys Val Ser Ser Gly Gly Gly Gly Ser Gly Gly Gly Ser Glu Val
            290                 295                 300
Gln Leu Val Glu Ser Gly Gly Val Val Gln Pro Gly Asn Ser Leu
305                 310                 315                 320
Arg Leu Ser Cys Ala Ala Ser Gly Phe Thr Phe Ser Ser Phe Gly Met
                325                 330                 335
Ser Trp Val Arg Gln Ala Pro Gly Lys Gly Leu Glu Trp Val Ser Ser
            340                 345                 350
Ile Ser Gly Ser Gly Ser Asp Thr Leu Tyr Ala Asp Ser Val Lys Gly
            355                 360                 365
Arg Phe Thr Ile Ser Arg Asp Asn Ala Lys Thr Thr Leu Tyr Leu Gln
            370                 375                 380
Met Asn Ser Leu Arg Pro Glu Asp Thr Ala Leu Tyr Tyr Cys Thr Ile
385                 390                 395                 400
Gly Gly Ser Leu Ser Arg Ser Ser Gln Gly Thr Leu Val Thr Val Ser
                405                 410                 415
Ser Ala

<210> SEQ ID NO 125
<211> LENGTH: 418
<212> TYPE: PRT
<213> ORGANISM: Artificial Sequence
<220> FEATURE:
<223> OTHER INFORMATION: CDR Sequence

<400> SEQUENCE: 125

Asp Val Gln Leu Val Glu Ser Gly Gly Lys Val Val Gln Pro Gly Gly
1               5                   10                  15
Ser Leu Arg Leu Ser Cys Ser Ala Ser Gly Arg Thr Phe Ser Phe Ser
                20                  25                  30
Thr Ser Thr Met Gly Trp Phe Arg Gln Ala Pro Gly Lys Glu Leu Glu
            35                  40                  45
Phe Val Ala Ala Ile Asp Trp Ser Asp Phe Asn Thr Tyr Tyr Ala Asp
        50                  55                  60
```

```
Ser Val Lys Gly Arg Phe Thr Ile Ser Arg His Asn Pro Arg Asn Ser
 65                  70                  75                  80

Val Tyr Leu Gln Leu Asn Ser Leu Lys Pro Glu Asp Thr Ala Leu Tyr
                 85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Thr Val
            115                 120                 125

Ser Ser Gly Gly Gly Gly Ser Gly Gly Gly Gly Ser Gly Gly Gly Gly
130                 135                 140

Ser Gly Gly Gly Gly Ser Gly Gly Gly Ser Gly Gly Gly Gly Ser
145                 150                 155                 160

Gly Gly Gly Gly Glu Val Gln Leu Val Glu Ser Gly Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
            195                 200                 205

Arg Glu Phe Val Ala Ala Ile Ser Ser Tyr Gly Ser Thr Asp Tyr Gly
210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
            245                 250                 255

Tyr Tyr Cys Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
            275                 280                 285

Val Lys Val Ser Ser Gly Gly Gly Ser Gly Gly Gly Ser Glu Val
290                 295                 300

Gln Leu Val Glu Ser Gly Gly Gly Val Val Gln Pro Gly Asn Ser Leu
305                 310                 315                 320

Arg Leu Ser Cys Ala Ala Ser Gly Phe Thr Phe Ser Ser Phe Gly Met
            325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
            370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
                405                 410                 415

Ser Ala

<210> SEQ ID NO 126
<211> LENGTH: 418
<212> TYPE: PRT
<213> ORGANISM: Artificial Sequence
<220> FEATURE:
<223> OTHER INFORMATION: CDR Sequence

<400> SEQUENCE: 126
```

```
Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
            115                 120                 125

Ser Ser Gly Gly Gly Gly Ser Gly Gly Gly Gly Ser Gly Gly Gly Gly
            130                 135                 140

Ser Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
            195                 200                 205

Arg Glu Phe Val Ala Ala Ile Ser Ser Tyr Gly Ser Thr Asp Tyr Gly
            210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
            245                 250                 255

Tyr Tyr Cys Ala Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
            275                 280                 285

Val Lys Val Ser Ser Gly Gly Gly Ser Gly Gly Gly Ser Glu Val
            290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
            325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
            370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
            405                 410                 415

Ser Ala
```

```
<210> SEQ ID NO 127
<211> LENGTH: 418
<212> TYPE: PRT
<213> ORGANISM: Artificial Sequence
<220> FEATURE:
<223> OTHER INFORMATION: CDR Sequence

<400> SEQUENCE: 127

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Leu Val Lys Val
            115                 120                 125

Ser Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
        195                 200                 205

Arg Glu Phe Val Ala Ala Ile Ser Ser Tyr Gly Ser Thr Asp Tyr Gly
    210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
        275                 280                 285

Val Lys Val Ser Ser Gly Gly Gly Gly Ser Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365
```

```
Arg Phe Thr Ile Ser Arg Asp Asn Ala Lys Thr Thr Leu Tyr Leu Gln
            370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Gln Gly Thr Leu Val Thr Val Ser
                405                 410                 415

Ser Ala

<210> SEQ ID NO 128
<211> LENGTH: 418
<212> TYPE: PRT
<213> ORGANISM: Artificial Sequence
<220> FEATURE:
<223> OTHER INFORMATION: CDR Sequence

<400> SEQUENCE: 128

Asp Val Gln Leu Val Glu Ser Gly Gly Lys Val Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Leu Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Leu Val Lys Val
        115                 120                 125

Ser Ser Gly Gly Gly Gly Ser Gly Gly Gly Gly Ser Gly Gly Gly Gly
130                 135                 140

Ser Gly Gly Gly Gly Ser Gly Gly Gly Gly Ser Gly Gly Gly Gly Ser
145                 150                 155                 160

Gly Gly Gly Gly Glu Val Gln Leu Val Glu Ser Gly Gly Gly Val Val
                165                 170                 175

Gln Pro Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
        195                 200                 205

Arg Glu Phe Val Ala Ala Ile Ser Ser Tyr Gly Ser Thr Asp Tyr Gly
210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Leu
                245                 250                 255

Tyr Tyr Cys Ala Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
        275                 280                 285

Val Lys Val Ser Ser Gly Gly Gly Gly Ser Gly Gly Gly Ser Glu Val
290                 295                 300
```

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Phe Gly Met
            325                 330                 335

Ser Trp Val Arg Gln Ala Pro Gly Lys Gly Leu Glu Trp Val Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Leu Tyr Leu Gln
        370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Lys Val Ser
            405                 410                 415

Ser Ala

<210> SEQ ID NO 129
<211> LENGTH: 130
<212> TYPE: PRT
<213> ORGANISM: Artificial Sequence
<220> FEATURE:
<223> OTHER INFORMATION: CDR Sequence

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 130
<211> LENGTH: 130
<212> TYPE: PRT
<213> ORGANISM: Artificial Sequence
<220> FEATURE:
<223> OTHER INFORMATION: CDR Sequence

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

```
Phe Val Ala Ala Ile Asp Trp Ser Asp Phe Asn Thr Tyr Tyr Ala Asp
         50                  55                  60

Ser Val Lys Gly Arg Phe Thr Ile Ser Arg His Asn Pro Arg Asn Ser
 65                  70                  75                  80

Val Tyr Leu Gln Met Asn Ser Leu Arg Pro Glu Asp Thr Ala Val Tyr
                 85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 131
<211> LENGTH: 130
<212> TYPE: PRT
<213> ORGANISM: Artificial Sequence
<220> FEATURE:
<223> OTHER INFORMATION: CDR Sequence

<400> SEQUENCE: 131

Glu Val Gln Leu Val Glu Ser Gly Gly Gly Leu Val Gln Pro Gly Gly
 1               5                  10                  15

Ser Leu Arg Leu Ser Cys Ser Ala Ser Gly Arg Thr Phe Ser Phe Ser
             20                  25                  30

Thr Ser Thr Met Gly Trp Phe Arg Gln Ala Pro Gly Lys Glu Leu Glu
         35                  40                  45

Phe Val Ala Ala Ile Asp Trp Ser Asp Phe Asn Thr Tyr Tyr Ala Asp
         50                  55                  60

Ser Val Lys Gly Arg Phe Thr Ile Ser Arg Asp Asn Pro Arg Asn Ser
 65                  70                  75                  80

Val Tyr Leu Gln Met Asn Ser Leu Arg Pro Glu Asp Thr Ala Val Tyr
                 85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 132
<211> LENGTH: 130
<212> TYPE: PRT
<213> ORGANISM: Artificial Sequence
<220> FEATURE:
<223> OTHER INFORMATION: CDR Sequence

<400> SEQUENCE: 132

Glu Val Gln Leu Val Glu Ser Gly Gly Gly Leu Val Gln Pro Gly Gly
 1               5                  10                  15

Ser Leu Arg Leu Ser Cys Ser Ala Ser Gly Arg Thr Phe Ser Phe Ser
             20                  25                  30

Thr Ser Thr Met Gly Trp Phe Arg Gln Ala Pro Gly Lys Glu Leu Glu
         35                  40                  45

Phe Val Ala Ala Ile Asp Trp Ser Asp Phe Asn Thr Tyr Tyr Ala Asp
         50                  55                  60

Ser Val Lys Gly Arg Phe Thr Ile Ser Arg His Asn Ser Arg Asn Ser
 65                  70                  75                  80
```

```
Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 133
<211> LENGTH: 130
<212> TYPE: PRT
<213> ORGANISM: Artificial Sequence
<220> FEATURE:
<223> OTHER INFORMATION: CDR Sequence

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Lys Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 134
<211> LENGTH: 130
<212> TYPE: PRT
<213> ORGANISM: Artificial Sequence
<220> FEATURE:
<223> OTHER INFORMATION: CDR Sequence

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
```

```
                 100                 105                 110
Arg Pro Ser Leu Tyr Asn Tyr Trp Gly Gln Gly Thr Gln Val Thr Val
            115                 120                 125

Ser Ser
    130

<210> SEQ ID NO 135
<211> LENGTH: 130
<212> TYPE: PRT
<213> ORGANISM: Artificial Sequence
<220> FEATURE:
<223> OTHER INFORMATION: CDR Sequence

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

Phe Val Ala Ala Ile Asp Trp Ser Asp Phe Asn Thr Tyr Tyr Ala Asp
50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser
    130

<210> SEQ ID NO 136
<211> LENGTH: 129
<212> TYPE: PRT
<213> ORGANISM: Artificial Sequence
<220> FEATURE:
<223> OTHER INFORMATION: CDR Sequence

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125
```

Ser

<210> SEQ ID NO 137
<211> LENGTH: 129
<212> TYPE: PRT
<213> ORGANISM: Artificial Sequence
<220> FEATURE:
<223> OTHER INFORMATION: CDR Sequence

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 138
<211> LENGTH: 129
<212> TYPE: PRT
<213> ORGANISM: Artificial Sequence
<220> FEATURE:
<223> OTHER INFORMATION: CDR Sequence

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asn Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 139
<211> LENGTH: 129
<212> TYPE: PRT
<213> ORGANISM: Artificial Sequence
<220> FEATURE:
<223> OTHER INFORMATION: CDR Sequence

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 140
<211> LENGTH: 129
<212> TYPE: PRT
<213> ORGANISM: Artificial Sequence
<220> FEATURE:
<223> OTHER INFORMATION: CDR Sequence

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asp Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 141
<211> LENGTH: 129
<212> TYPE: PRT
<213> ORGANISM: Artificial Sequence
<220> FEATURE:
<223> OTHER INFORMATION: CDR Sequence

<400> SEQUENCE: 141

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Ala Asp Ser Val Lys
50                      55                  60

Gly Arg Phe Thr Ile Ser Arg Asp Asn Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser
```

```
<210> SEQ ID NO 142
<211> LENGTH: 129
<212> TYPE: PRT
<213> ORGANISM: Artificial Sequence
<220> FEATURE:
<223> OTHER INFORMATION: CDR Sequence

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
50                      55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser
```

```
<210> SEQ ID NO 143
<211> LENGTH: 129
<212> TYPE: PRT
<213> ORGANISM: Artificial Sequence
<220> FEATURE:
<223> OTHER INFORMATION: CDR Sequence

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45
```

```
Ala Ala Ile Ser Ser Tyr Gly Ser Thr Asp Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser

<210> SEQ ID NO 144
<211> LENGTH: 418
<212> TYPE: PRT
<213> ORGANISM: Artificial Sequence
<220> FEATURE:
<223> OTHER INFORMATION: CDR Sequence

<400> SEQUENCE: 144

Asp Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Arg His Tyr
             20                  25                  30

Ala Met Gly Trp Phe Arg Gln Ala Pro Gly Lys Glu Arg Glu Phe Val
             35                  40                  45

Ala Ala Ile Ser Ser Tyr Gly Ser Thr Asp Tyr Gly Asp Ser Val Lys
 50                  55                  60

Gly Arg Phe Thr Ile Ser Arg Asp Asp Ala Lys Asn Thr Val Pro Leu
 65                  70                  75                  80

Gln Met Asn Ser Leu Lys Pro Glu Asp Thr Ala Val Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Gly Gly Gly Gly Ser Gly Gly Gly Gly Ser Gly Gly Gly Gly Ser
            130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Leu Val
            165                 170                 175

Gln Ala Gly Gly Ser Leu Arg Leu Ser Cys Ala Ala Ser Gly Arg Thr
            180                 185                 190

Phe Arg His Tyr Ala Met Gly Trp Phe Arg Gln Ala Pro Gly Lys Glu
            195                 200                 205

Arg Glu Phe Val Ala Ala Ile Ser Ser Tyr Gly Ser Thr Asp Tyr Gly
            210                 215                 220

Asp Ser Val Lys Gly Arg Phe Thr Ile Ser Arg Asp Asp Ala Lys Asn
225                 230                 235                 240

Thr Val Pro Leu Gln Met Asn Ser Leu Lys Pro Glu Asp Thr Ala Val
            245                 250                 255

Tyr Tyr Cys Ala Ala Ala Asp Glu Thr Leu Gly Ala Val Pro Asn Phe
            260                 265                 270

Arg Leu His Glu Lys Tyr Glu Tyr Glu Tyr Trp Gly Gln Gly Thr Leu
```

```
                275                 280                 285
Val Thr Val Ser Ser Gly Gly Gly Ser Gly Gly Ser Glu Val
        290                 295                 300

Gln Leu Val Glu Ser Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 145
<211> LENGTH: 420
<212> TYPE: PRT
<213> ORGANISM: Artificial Sequence
<220> FEATURE:
<223> OTHER INFORMATION: CDR Sequence

<400> SEQUENCE: 145

Asp Val Gln Leu Val Glu Ser Gly Gly Lys Leu Val Gln Ala Gly Gly
1               5                   10                  15

Ser Leu Arg Leu Ser Cys Ser Ala Ser Gly Arg Thr Phe Ser Phe Ser
                20                  25                  30

Thr Ser Thr Met Gly Trp Phe Arg Gln Ala Pro Gly Lys Glu Leu Glu
                35                  40                  45

Phe Val Ala Ala Ile Asp Trp Ser Asp Phe Asn Thr Tyr Tyr Ala Asp
        50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
                100                 105                 110

Arg Pro Ser Leu Tyr Asn Tyr Trp Gly Gln Gly Thr Leu Val Thr Val
                115                 120                 125

Ser Ser Gly Gly Gly Gly Ser Gly Gly Gly Gly Ser Gly Gly Gly Gly
                130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Lys Leu
                165                 170                 175

Val Gln Ala Gly Gly Ser Leu Arg Leu Ser Cys Ser Ala Ser Gly Arg
                180                 185                 190

Thr Phe Ser Phe Ser Thr Ser Thr Met Gly Trp Phe Arg Gln Ala Pro
                195                 200                 205

Gly Lys Glu Leu Glu Phe Val Ala Ala Ile Asp Trp Ser Asp Phe Asn
                210                 215                 220
```

Thr Tyr Tyr Ala Asp Ser Val Lys Gly Arg Phe Thr Ile Ser Arg His
225                 230                 235                 240

Asn Pro Arg Asn Ser Val Tyr Leu Gln Leu Asn Ser Leu Lys Pro Glu
            245                 250                 255

Asp Thr Ala Val Tyr Tyr Cys Ala Ala His Ser Glu Thr Arg Gly Gly
        260                 265                 270

Thr Arg Tyr Phe Asp Arg Pro Ser Leu Tyr Asn Tyr Trp Gly Gln Gly
    275                 280                 285

Thr Leu Val Thr Val Ser Ser Gly Gly Gly Ser Gly Gly Gly Ser
290                 295                 300

Glu Val Gln Leu Val Glu Ser Gly Gly Leu Val Gln Pro Gly Asn
305                 310                 315                 320

Ser Leu Arg Leu Ser Cys Ala Ala Ser Gly Phe Thr Phe Ser Ser Phe
            325                 330                 335

Gly Met Ser Trp Val Arg Gln Ala Pro Gly Lys Gly Leu Glu Trp Val
            340                 345                 350

Ser Ser Ile Ser Gly Ser Gly Ser Asp Thr Leu Tyr Ala Asp Ser Val
            355                 360                 365

Lys Gly Arg Phe Thr Ile Ser Arg Asp Asn Ala Lys Thr Thr Leu Tyr
370                 375                 380

Leu Gln Met Asn Ser Leu Arg Pro Glu Asp Thr Ala Val Tyr Tyr Cys
385                 390                 395                 400

Thr Ile Gly Gly Ser Leu Ser Arg Ser Ser Gln Gly Thr Leu Val Thr
            405                 410                 415

Val Ser Ser Ala
            420

<210> SEQ ID NO 146
<211> LENGTH: 419
<212> TYPE: PRT
<213> ORGANISM: Artificial Sequence
<220> FEATURE:
<223> OTHER INFORMATION: CDR Sequence

<400> SEQUENCE: 146

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Gly Asp Ser Val Lys
50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Lys Leu Val
                165                 170                 175

Gln Ala Gly Gly Ser Leu Arg Leu Ser Cys Ser Ala Ser Gly Arg Thr
            180                 185                 190

Phe Ser Phe Ser Thr Ser Thr Met Gly Trp Phe Arg Gln Ala Pro Gly
        195                 200                 205

Lys Glu Leu Glu Phe Val Ala Ala Ile Asp Trp Ser Asp Phe Asn Thr
    210                 215                 220

Tyr Tyr Ala Asp Ser Val Lys Gly Arg Phe Thr Ile Ser Arg His Asn
225                 230                 235                 240

Pro Arg Asn Ser Val Tyr Leu Gln Leu Asn Ser Leu Lys Pro Glu Asp
            245                 250                 255

Thr Ala Val Tyr Tyr Cys Ala Ala His Ser Glu Thr Arg Gly Gly Thr
        260                 265                 270

Arg Tyr Phe Asp Arg Pro Ser Leu Tyr Asn Tyr Trp Gly Gln Gly Thr
    275                 280                 285

Leu Val Thr Val Ser Ser Gly Gly Gly Gly Ser Gly Gly Gly Ser Glu
290                 295                 300

Val Gln Leu Val Glu Ser Gly Gly Leu Val Gln Pro Gly Asn Ser
305                 310                 315                 320

Leu Arg Leu Ser Cys Ala Ala Ser Gly Phe Thr Phe Ser Ser Phe Gly
            325                 330                 335

Met Ser Trp Val Arg Gln Ala Pro Gly Lys Gly Leu Glu Trp Val Ser
        340                 345                 350

Ser Ile Ser Gly Ser Gly Ser Asp Thr Leu Tyr Ala Asp Ser Val Lys
    355                 360                 365

Gly Arg Phe Thr Ile Ser Arg Asp Asn Ala Lys Thr Thr Leu Tyr Leu
    370                 375                 380

Gln Met Asn Ser Leu Arg Pro Glu Asp Thr Ala Val Tyr Tyr Cys Thr
385                 390                 395                 400

Ile Gly Gly Ser Leu Ser Arg Ser Ser Gln Gly Thr Leu Val Thr Val
            405                 410                 415

Ser Ser Ala

<210> SEQ ID NO 147
<211> LENGTH: 130
<212> TYPE: PRT
<213> ORGANISM: Artificial Sequence
<220> FEATURE:
<223> OTHER INFORMATION: CDR Sequence

<400> SEQUENCE: 147

Asp Val Gln Leu Val Glu Ser Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Met Asn Ser Leu Arg Pro Glu Asp Thr Ala Val Tyr
            85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser
    130

<210> SEQ ID NO 148
<211> LENGTH: 130
<212> TYPE: PRT
<213> ORGANISM: Artificial Sequence
<220> FEATURE:
<223> OTHER INFORMATION: CDR Sequence

<400> SEQUENCE: 148

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser
    130

<210> SEQ ID NO 149
<211> LENGTH: 130
<212> TYPE: PRT
<213> ORGANISM: Artificial Sequence
<220> FEATURE:
<223> OTHER INFORMATION: CDR Sequence

<400> SEQUENCE: 149

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg Asp Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser
    130

<210> SEQ ID NO 150
<211> LENGTH: 130
<212> TYPE: PRT
<213> ORGANISM: Artificial Sequence
<220> FEATURE:
<223> OTHER INFORMATION: CDR Sequence

<400> SEQUENCE: 150

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Ser Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 151
<211> LENGTH: 130
<212> TYPE: PRT
<213> ORGANISM: Artificial Sequence
<220> FEATURE:
<223> OTHER INFORMATION: CDR Sequence

<400> SEQUENCE: 151

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Lys Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130

<210> SEQ ID NO 152
<211> LENGTH: 130
<212> TYPE: PRT
<213> ORGANISM: Artificial Sequence
<220> FEATURE:
<223> OTHER INFORMATION: CDR Sequence

<400> SEQUENCE: 152

```
Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130
```

<210> SEQ ID NO 153
<211> LENGTH: 130
<212> TYPE: PRT
<213> ORGANISM: Artificial Sequence
<220> FEATURE:
<223> OTHER INFORMATION: CDR Sequence

<400> SEQUENCE: 153

```
Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser
    130
```

<210> SEQ ID NO 154
<211> LENGTH: 129
<212> TYPE: PRT
<213> ORGANISM: Artificial Sequence
<220> FEATURE:

<223> OTHER INFORMATION: CDR Sequence

<400> SEQUENCE: 154

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 155
<211> LENGTH: 129
<212> TYPE: PRT
<213> ORGANISM: Artificial Sequence
<220> FEATURE:
<223> OTHER INFORMATION: CDR Sequence

<400> SEQUENCE: 155

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 156
<211> LENGTH: 129
<212> TYPE: PRT
<213> ORGANISM: Artificial Sequence
<220> FEATURE:
<223> OTHER INFORMATION: CDR Sequence

<400> SEQUENCE: 156

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asn Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 157
<211> LENGTH: 129
<212> TYPE: PRT
<213> ORGANISM: Artificial Sequence
<220> FEATURE:
<223> OTHER INFORMATION: CDR Sequence

<400> SEQUENCE: 157

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 158
<211> LENGTH: 129
<212> TYPE: PRT
<213> ORGANISM: Artificial Sequence
<220> FEATURE:
<223> OTHER INFORMATION: CDR Sequence

<400> SEQUENCE: 158

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys

```
                 50                  55                  60
Gly Arg Phe Thr Ile Ser Arg Asp Asp Ser Lys Asn Thr Val Tyr Leu
 65                  70                  75                  80

Gln Met Asn Ser Leu Arg Pro Glu Asp Thr Ala Val Tyr Tyr Cys Ala
                     85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Thr Val Ser
                115                 120                 125

Ser

<210> SEQ ID NO 159
<211> LENGTH: 129
<212> TYPE: PRT
<213> ORGANISM: Artificial Sequence
<220> FEATURE:
<223> OTHER INFORMATION: CDR Sequence

<400> SEQUENCE: 159

Asp Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Arg His Tyr
                 20                  25                  30

Ala Met Gly Trp Phe Arg Gln Ala Pro Gly Lys Glu Arg Glu Phe Val
             35                  40                  45

Ala Ala Ile Ser Ser Tyr Gly Ser Thr Asp Tyr Ala Asp Ser Val Lys
         50                  55                  60

Gly Arg Phe Thr Ile Ser Arg Asp Asn Ser Lys Asn Thr Val Pro Leu
 65                  70                  75                  80

Gln Met Asn Ser Leu Arg Pro Glu Asp Thr Ala Val Tyr Tyr Cys Ala
                     85                  90                  95

Ala Ala Asp Glu Thr Leu Gly Ala Val Pro Asn Phe Arg Leu His Glu
                100                 105                 110

Lys Tyr Glu Tyr Glu Tyr Trp Gly Gln Gly Thr Leu Val Thr Val Ser
                115                 120                 125

Ser

<210> SEQ ID NO 160
<211> LENGTH: 129
<212> TYPE: PRT
<213> ORGANISM: Artificial Sequence
<220> FEATURE:
<223> OTHER INFORMATION: CDR Sequence

<400> SEQUENCE: 160

Asp Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Arg His Tyr
                 20                  25                  30

Ala Met Gly Trp Phe Arg Gln Ala Pro Gly Lys Glu Arg Glu Phe Val
             35                  40                  45

Ala Ala Ile Ser Ser Tyr Gly Ser Thr Asp Tyr Gly Asp Ser Val Lys
         50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                     85                  90                  95
```

```
Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 161
<211> LENGTH: 129
<212> TYPE: PRT
<213> ORGANISM: Artificial Sequence
<220> FEATURE:
<223> OTHER INFORMATION: CDR Sequence

<400> SEQUENCE: 161

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser

<210> SEQ ID NO 162
<211> LENGTH: 131
<212> TYPE: PRT
<213> ORGANISM: Artificial Sequence
<220> FEATURE:
<223> OTHER INFORMATION: CDR Sequence

<400> SEQUENCE: 162

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Gln Val Thr Val
        115                 120                 125
```

Ser Ser Ala
    130

<210> SEQ ID NO 163
<211> LENGTH: 131
<212> TYPE: PRT
<213> ORGANISM: Artificial Sequence
<220> FEATURE:
<223> OTHER INFORMATION: CDR Sequence

<400> SEQUENCE: 163

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser Ala
    130

<210> SEQ ID NO 164
<211> LENGTH: 131
<212> TYPE: PRT
<213> ORGANISM: Artificial Sequence
<220> FEATURE:
<223> OTHER INFORMATION: CDR Sequence

<400> SEQUENCE: 164

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg Asp Asn Pro Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser Ala
    130

<210> SEQ ID NO 165

<211> LENGTH: 131
<212> TYPE: PRT
<213> ORGANISM: Artificial Sequence
<220> FEATURE:
<223> OTHER INFORMATION: CDR Sequence

<400> SEQUENCE: 165

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
50                  55                  60

Ser Val Lys Gly Arg Phe Thr Ile Ser Arg His Asn Ser Arg Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser Ala
    130

<210> SEQ ID NO 166
<211> LENGTH: 131
<212> TYPE: PRT
<213> ORGANISM: Artificial Sequence
<220> FEATURE:
<223> OTHER INFORMATION: CDR Sequence

<400> SEQUENCE: 166

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
50                  55                  60

Ser Val Lys Gly Arg Phe Thr Ile Ser Arg His Asn Pro Lys Asn Ser
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser Ala
    130

<210> SEQ ID NO 167
<211> LENGTH: 131
<212> TYPE: PRT
<213> ORGANISM: Artificial Sequence
<220> FEATURE:
<223> OTHER INFORMATION: CDR Sequence

<400> SEQUENCE: 167

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser Ala
        130

<210> SEQ ID NO 168
<211> LENGTH: 131
<212> TYPE: PRT
<213> ORGANISM: Artificial Sequence
<220> FEATURE:
<223> OTHER INFORMATION: CDR Sequence

<400> SEQUENCE: 168

Asp Val Gln Leu Val Glu Ser Gly Gly Gly Leu Val Gln Pro Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Arg Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser Ala
        130

<210> SEQ ID NO 169
<211> LENGTH: 130
<212> TYPE: PRT
<213> ORGANISM: Artificial Sequence
<220> FEATURE:
<223> OTHER INFORMATION: CDR Sequence

<400> SEQUENCE: 169

Asp Val Gln Leu Val Glu Ser Gly Gly Gly Leu Val Gln Pro Gly Gly
1               5                   10                  15

```
Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Ala
    130

<210> SEQ ID NO 170
<211> LENGTH: 130
<212> TYPE: PRT
<213> ORGANISM: Artificial Sequence
<220> FEATURE:
<223> OTHER INFORMATION: CDR Sequence

<400> SEQUENCE: 170

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asp Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Ala
    130

<210> SEQ ID NO 171
<211> LENGTH: 130
<212> TYPE: PRT
<213> ORGANISM: Artificial Sequence
<220> FEATURE:
<223> OTHER INFORMATION: CDR Sequence

<400> SEQUENCE: 171

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
```

```
                35                  40                  45
Ala Ala Ile Ser Ser Tyr Gly Ser Thr Asp Tyr Gly Asp Ser Val Lys
        50                  55                  60

Gly Arg Phe Thr Ile Ser Arg Asp Asn Ser Lys Asn Thr Val Pro Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Ala
    130

<210> SEQ ID NO 172
<211> LENGTH: 130
<212> TYPE: PRT
<213> ORGANISM: Artificial Sequence
<220> FEATURE:
<223> OTHER INFORMATION: CDR Sequence

<400> SEQUENCE: 172

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
        50                  55                  60

Gly Arg Phe Thr Ile Ser Arg Asp Asp Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Ala
    130

<210> SEQ ID NO 173
<211> LENGTH: 130
<212> TYPE: PRT
<213> ORGANISM: Artificial Sequence
<220> FEATURE:
<223> OTHER INFORMATION: CDR Sequence

<400> SEQUENCE: 173

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Ala Asp Ser Val Lys
        50                  55                  60
```

```
Gly Arg Phe Thr Ile Ser Arg Asp Asp Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Ala
    130

<210> SEQ ID NO 174
<211> LENGTH: 130
<212> TYPE: PRT
<213> ORGANISM: Artificial Sequence
<220> FEATURE:
<223> OTHER INFORMATION: CDR Sequence

<400> SEQUENCE: 174

Asp Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Arg His Tyr
             20                  25                  30

Ala Met Gly Trp Phe Arg Gln Ala Pro Gly Lys Glu Arg Glu Phe Val
         35                  40                  45

Ala Ala Ile Ser Ser Tyr Gly Ser Thr Asp Tyr Ala Asp Ser Val Lys
 50                  55                  60

Gly Arg Phe Thr Ile Ser Arg Asp Asn Ser Lys Asn Thr Val Pro Leu
 65                  70                  75                  80

Gln Met Asn Ser Leu Arg Pro Glu Asp Thr Ala Val Tyr Tyr Cys Ala
                 85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
        115                 120                 125

Ser Ala
    130

<210> SEQ ID NO 175
<211> LENGTH: 130
<212> TYPE: PRT
<213> ORGANISM: Artificial Sequence
<220> FEATURE:
<223> OTHER INFORMATION: CDR Sequence

<400> SEQUENCE: 175

Asp Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Arg His Tyr
             20                  25                  30

Ala Met Gly Trp Phe Arg Gln Ala Pro Gly Lys Glu Arg Glu Phe Val
         35                  40                  45

Ala Ala Ile Ser Ser Tyr Gly Ser Thr Asp Tyr Gly Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95
```

```
Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Ala
    130

<210> SEQ ID NO 176
<211> LENGTH: 130
<212> TYPE: PRT
<213> ORGANISM: Artificial Sequence
<220> FEATURE:
<223> OTHER INFORMATION: CDR Sequence

<400> SEQUENCE: 176

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
            35                  40                  45

Ala Ala Ile Ser Ser Tyr Gly Ser Thr Asp Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Leu Val Thr Val Ser
            115                 120                 125

Ser Ala
    130

<210> SEQ ID NO 177
<211> LENGTH: 4
<212> TYPE: PRT
<213> ORGANISM: Artificial Sequence
<220> FEATURE:
<223> OTHER INFORMATION: C-Terminal tag

<400> SEQUENCE: 177

Gly Gly Gly Cys
1
```

UNITED STATES PATENT AND TRADEMARK OFFICE
CERTIFICATE OF CORRECTION

PATENT NO. : 10,875,918 B2
APPLICATION NO. : 15/775266
DATED : December 29, 2020
INVENTOR(S) : Marie-Ange Buyse et al.

Page 1 of 1

It is certified that error appears in the above-identified patent and that said Letters Patent is hereby corrected as shown below:

In the Claims

Delete Claim 1, beginning at Column 261, Line 54, and insert:
--1. An immunoglobulin single variable domain that binds to the P2X7 receptor comprising the structure of FR1-CDR1-FR2-CDR2-FR3-CDR3-FR4; wherein FR1 to FR4 refer to framework regions (FRs) 1 to 4 of the immunoglobulin single variable domain; wherein CDR1 to CDR3 refer to complementary determining regions (CDRs) l to 3 of the immunoglobulin single variable domain; and wherein the immunoglobulin single variable domain has:
    a CDR1 chosen from the group consisting of SEQ ID NO: 2 and amino acid sequences
        that have 1 amino acid difference with SEQ ID NO:2; and
    a CDR2 chosen from the group consisting of SEQ ID NO: 3 and amino acid sequences
        that have 1 or 2 amino acid differences with SEQ ID NO:3; and
    a CDR3 chosen from the group consisting of SEQ ID NO: 4 and amino acid sequences
        that have 1 or 2 amino acid differences with SEQ ID NO:4;
and has:
    FRs that cumulatively have a degree of sequence identity of at least 85% with the FRs
        of SEQ ID NO:1;
and/or has:
    FRs that cumulatively have no more than 11 amino acid differences with the FRs of
        SEQ ID NO:1.--

Signed and Sealed this
Fourth Day of May, 2021

Drew Hirshfeld
*Performing the Functions and Duties of the
Under Secretary of Commerce for Intellectual Property and
Director of the United States Patent and Trademark Office*